US009095586B2

(12) United States Patent
Hillis et al.

(10) Patent No.: US 9,095,586 B2
(45) Date of Patent: Aug. 4, 2015

(54) SYSTEM FOR OBFUSCATING IDENTITY

(75) Inventors: W. Daniel Hillis, Encino, CA (US); Nathan P. Myhrvold, Medina, WA (US); Richa Wilson, San Francisco, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 1470 days.

(21) Appl. No.: 11/510,753

(22) Filed: Aug. 24, 2006

(65) Prior Publication Data

US 2008/0047551 A1 Feb. 28, 2008

Related U.S. Application Data

(63) Continuation-in-part of application No. 11/510,754, filed on Aug. 24, 2006, now Pat. No. 7,684,930, and a continuation-in-part of application No. 11/510,756, filed on Aug. 24, 2006, now Pat. No. 8,073,628.

(51) Int. Cl.
| | |
|---|---|
| G01N 33/48 | (2006.01) |
| A61K 38/47 | (2006.01) |
| G06F 19/22 | (2011.01) |
| A61K 38/48 | (2006.01) |
| A61K 38/46 | (2006.01) |

(52) U.S. Cl.
CPC ............... *A61K 38/47* (2013.01); *A61K 38/465* (2013.01); *A61K 38/48* (2013.01); *G06F 19/22* (2013.01)

(58) Field of Classification Search
CPC ...................................................... G06F 19/22
USPC .......................................................... 702/19
See application file for complete search history.

(56) References Cited

U.S. PATENT DOCUMENTS

| | | | | | |
|---|---|---|---|---|---|
| 3,768,732 | A | * | 10/1973 | Curtis et al. | 239/70 |
| RE31,023 | E | * | 9/1982 | Hall, III | 405/37 |
| 4,662,900 | A | | 5/1987 | Ottengraf | |
| D313,098 | S | | 12/1990 | Boyd | |
| 5,877,390 | A | | 3/1999 | Kuriyama et al. | |
| 6,296,808 | B1 | | 10/2001 | Pearman | |
| 6,620,611 | B2 | | 9/2003 | Hince | |
| 6,656,898 | B1 | | 12/2003 | Foley et al. | |
| 6,787,104 | B1 | | 9/2004 | Mariella, Jr. | |
| 6,969,487 | B1 | * | 11/2005 | Sias et al. | 422/28 |
| 8,457,798 | B2 | * | 6/2013 | Hackett | 700/284 |
| 2003/0170877 | A1 | | 9/2003 | Yano et al. | |
| 2004/0054155 | A1 | | 3/2004 | Woolf et al. | |
| 2004/0163705 | A1 | * | 8/2004 | Uhler | 137/79 |
| 2006/0008379 | A1 | * | 1/2006 | Mielnik et al. | 422/32 |
| 2006/0051765 | A1 | | 3/2006 | Zhang et al. | |
| 2007/0044487 | A1 | | 3/2007 | Craig | |
| 2007/0221750 | A1 | * | 9/2007 | Roberts | 239/200 |
| 2008/0287318 | A1 | | 11/2008 | Kranewitter et al. | |

FOREIGN PATENT DOCUMENTS

WO WO 01/36676 A2 * 5/2001 ............... C12Q 1/68

OTHER PUBLICATIONS

Braasch et al. "Novel Antisense and Peptide Nucleic Acid Strategies for Controlling Gene Expression," Biochemistry (2002) vol. 41, No. 14, pp. 4503-4510.*
Hochstrasser, Mark "Ubiquitin, Proteasomes, and the Regulation of Intracellular Protein Degradation," Current Opinion in Cell Biology (1995) vol. 7, pp. 215-223.*
Kemp et al. "Use of Bleach to Elimiate Contaminating DNA from the Surfaces of Bones and Teeth," Forensic Science International (2005) vol. 154, pp. 53-61.*
"New Products"; Nature Biotechnology; Aug. 1999; p. 827; vol. 17; Nature America Inc.; located at http://biotech.nature.com/.
"Warming to the Task"; Nature; Nov. 2003; pp. 205-208; vol. 426; Nature Publishing Group; located at www.nature.com/nature/.
PCT International Search Report; International Application No. PCT /US2007/018790; Sep. 30, 2008; pp. 1-4.
U.S. Appl. No. 11/724,058, Hillis et al.
U.S. Appl. No. 11/724,051, Hillis et al.
U.S. Appl. No. 11/724,033, Hillis et al.
Pregibon, Daniel C.; Toner, Mehmet; Doyle, Patrick S.; "Multifunctional Encoded Particles for High-Throughput Biomolecule Analysis"; Science; Mar. 9, 2007; pp. 1393-1396; vol. 315; www.sciencemag.org.
"DNAZap: PCR DNA Degradation Solution"; Ambion; pp. 1-2.
Galbraith et al.; "Printing DNA Microarrays using the Biomek® 2000 Laboratory Automation Workstation"; Methods in Molecular Biology; 2001 (date provided by examiner); pp. 131-140; vol. 170: DNA Arrays: Methods and Protocols; Humana Press Inc.
Alessandrini, Federica, B.SC.; Turchi, Chiara, B.SC.; Onofri, Valerio, B.SC.; Buscemi, Loredana, M.D.; Pesaresi, Mauro, M.D.; Tagliabracci, Adriano, M.D.; "Multiplex PCR Development of Y-Chromosomal Biallelic Polymorphisms for Forensic Application"; Journal Forensic Science; Bearing a date of May 2005; pp. 1-7; vol. 50, No. 3; ASTM International; located at: www.astm.org.
Beebe, David J.; Mensing, Glennys A.; Walker, Glenn M.; "Physics and Applications of Microfluidics in Biology"; Annual Review of Biomedical Engineering; Bearing a date of 2002; pp. 261-286; vol. 4; Annual Reviews; located at: arjournals.annualreviews.org.
"Bio Breeze"; Deodorizer/Germistat/Fungistat; Bearing dates of 2001-2006; pp. 1-4; Peak Pure Air.net; located at: http://www.peakpureair.net/bio-breeze.htm.
Bríon, María; Sanchez, Juan J.; Balogh, Kinga; Thacker, Catherine; Blanco-Verea, Alejandro; Børsting, Claus; Stradmann-Bellinghausen, Beate; Bogus, Magdalena; Syndercombe-Court, Denise; Schneider, Peter M.; Carracedo, Angel; Morling, Niels; "Introduction of an Single Nucleodite Polymorphism-based "Major Y-Chromosome Haplogroup Typing Kit" Suitable for Predicting the Geographical Origin of Male Lineages"; Electrophoresis; Bearing a date of 2005; pp. 4411-4420; vol. 26; Wiley-VCH Verlag GmbH & Co. KGaA, Weinheim.

(Continued)

*Primary Examiner* — Jerry Lin

(57) ABSTRACT

Compositions, apparatus, systems, kits, and methods for obfuscating the nucleic acid and/or protein content of an environment.

47 Claims, 21 Drawing Sheets

(56) References Cited

OTHER PUBLICATIONS

Brion, M.; Sobrino, B.; Blanco-Verea, A.; Lareu, M.V.; Carracedo, A.; "Hierarchical Analysis of 30 Y-Chromosome SNPs in European Populations"; Int. Journal Legal Med.; Bearing a date of 2004; pp. 10-15; vol. 119; Springer-Verlag.

Burchard González, Esteban, M.D.; Ziv, Elad, M.D.; Coyle, Natasha, Ph.D.; Gomez, Scarlett Lin, Ph.D.; Tang, Hua, Ph.D.; Karter, Andrew J., Ph.D.; Mountain, Joanna L., Ph.D.; Pérez-Stable, Eliseo J., M.D.; Sheppard, Dean, M.D.; Risch, Neil, Ph.D.; "The Importance of Race and Ethnic Background in Biomedical Research and Clinical Practice"; The New England Journal of Medicine; Bearing a date of Mar. 20, 2003; pp. 1170-1175; vol. 348, No. 12; Massachusetts Medical Society.

"Deodorizers & Air Fresheners"; Namco: Manufacturers of Carpet Cleaning Equipment, Chemicals & Janitorial Supplies; Bearing dates of 2004-2006; pp. 1-6; Namco Manufacturing Inc.; located at: http://www.namcomfg.com/chemicals/chems_deodorizersairfresheners.htm.

Divne, Anna-Maria; Allen, Marie; "A DNA Microarray System for Forensic SNP Analysis"; Forensic Science International; Bearing a date of 2005; pp. 111-121; vol. 154, Issue 2; located at: http://www.elsevier.com/locate/forsciint.

Douglas, Janice G., M.D.; Thibonnier, Marc, M.D., MSC; Wright, Jackson T., Jr., M.D., Ph.D.; "Essential Hypertension: Racial/Ethical Differences in Pathophysiology"; Journal of the Association for Academic Minority Physicians; Bearing a date of Jan. 1996; pp. 16-21; vol. 7, Issue 1.

"Fabric and Household Care: Genencor Leading the Way"; Bioproducts; Bearing a date of 2002; pp. 1-2; Genencor International; located at: http://www.genencor.com/wt/gcor.clean.

Fernandéz, José R.; Shriver, Mark D.; Beasley, T. Mark; Rafla-Demetrious, Nashwa; Parra, Esteban; Albu, Jeanine; Nicklas, Barbara; Ryan, Alice S.; McKeigue, Paul M.; Hoggart, Clive L.; Weinsier, Roland L.; Allison, David B.; "Association of African Genetic Admixture With Resting Metabolic Rate and Obesity Among Women"; Obesity Research; Bearing a date of Jul. 2003; pp. 904-911; vol. 11, No. 7; NAASO.

Gower, Barbara A.; Fernández, José R.; Beasley, T. Mark; Shriver, Mark D.; Goran, Michael I.; "Using Genetic Admixture to Explain Racial Differences in Insulin-Related Phenotypes"; Diabetes; Bearing a date of Apr. 2003; pp. 1047-1051; vol. 52.

Kumar, C. Ganesh; Malik, R.K.; Tiwari, M.P.; "Novel Enzyme-Based Detergents: An Indian Perspective"; Bearing dates of Apr. 20, 1998 and Sep. 24, 1998; pp. 1-11; located at: http://www.iisc.ernet.in/currsci/dec25/articles14.htm.

Lessig, R.; Zoledziewska, M.; Fahr, K.; Edelmann, J.; Kostrzewa, M.; Dobosz, T.; Kleemann, W.J.; "Y-SNP-Genotyping—A New Approach in Forensic Analysis"; Forensic Science International; Bearing a date of 2005; pp. 128-136; vol. 154; Elsevier Ireland Ltd.; located at: www.elsevier.com/locate/forsciint.

McNevin, Dennis; Wilson-Wilde, Linzi; Robertson, James; Kyd, Jennelle; Lennard, Chris; "Short Tandem Repeat (STR) Genotyping of Keratinised Hair. Part 1. Review of Current Status and Knowledge Gasps"; Forensic Science International; Bearing a date of Oct. 29, 2005; pp. 237-246; vol. 153, Issue 2; located: www.elsevier.com/locate/forsciint.

McNevin, Dennis; Wilson-Wilde, Linzi; Robertson, James; Kyd, Jennelle; Lennard, Chris; "Short Tandem Repeat (STR) Genotyping of Keratinised Hair. Part 2. An Optimised Genomic DNA Extraction Procedure Reveals Donor Dependence of STR Profiles"; Forensic Science International; Bearing a date of Oct. 29, 2005; pp. 247-259; vol. 153, Issue 2; located: www.elsevier.com/locate/forsciintt.

Nemcova, Tereza; "Europe: Czech Scientists Hail Discovery to Neutralize Mustard Gas"; Bearing a date of Aug. 5, 2005; pp. 1-3; located at: http://www.rferl.org/featuresarticle/2005/08/fe1a6b05-095c-4a5d-9ea4-1bb175e0bf74.html.

Onofri, Valerio; Alessandrini, Federica; Turchi, Chiara; Pesaresi, Mauro; Buscemi, Loredana; Tagliabracci, Adriano; "Development of Multiplex PCRs for Evolutionary and Forensic Applications of 37 Human Y Chromosome SNPs"; Forensic Science International; Bearing a date of 2006; pp. 23-35; vol. 157; Elsevier Ireland Ltd.; located at: www.elsevier.com/locate/forsciint.

Petkovski, Elizabet, ING.; Keyser-Tracqui, Christine, Ph.D.; Hienne, Rémi, Ph.D.; Ludes, Bertrand, M.D., Ph.D.; "SNPs and MALDI-TOF MS: Tools for DNA Typing in Forensic Paternity Testing and Anthropology"; Journal Forensic Science; Bearing a date of May 2005; pp. 1-7; vol. 50, No. 3; ASTM International; located at: www.astm.org.

Pitman, Simon; "Breaking News on Cosmetics Formulation & Packaging—North America: Scientists Discover Small Molecules up Botox Efficacy"; Cosmetics Design; Bearing a date of Mar. 15, 2006; pp. 1-2; Decision News Media SAS; located at: http://www.cosmeticsdesign.com/news/ng.asp?id=66432-scripps-botox.

Platz, Elizabeth A.; Rimm, Eric B.; Willett, Walter C.; Kantoff, Philip W.; Giovannucci, Edward; "Racial Variation in Prostate Cancer Incidence and in Hormonal System Markers Among Male Health Professionals"; Journal of the National Cancer Institute: Articles; Bearing a date of Dec. 20, 2000; pp. 2009-2017; vol. 92, No. 24; Oxford University Press.

"RNase Free Productivity Improver"; Pathtech; Bearing a date of 2004; pp. 1-1; Pathtech; located at: http://www.pathtech.com.au/pathtech/home/consumer/catalogue/molecularbiology/02/0501.sok.

Sobrino, Beatriz; Bríon, María; Carracedo, Angel; "SNPs in Forensic Genetics: A Review on SNP Typing Methodologies"; Forensic Science International; Bearing a date of 2005; pp. 181-194; vol. 154; Elsevier Ireland Ltd.; located at: www.elsevier.com/locate/forsciint.

Spirin, Alexander S.; Baranov, Vladimir I.; Ryabova, Lubov A.; Ovodov, Sergey Yu.; Alakhov, Yuly B.; "AContinuous Cell-Free Translation System Capable of Producing Polypeptides in High Yield"; Science; bearing a date of 11/25/198; pp. 1162-1164; vol. 242, No. 4882; Institute of Protein Research, Academy of Sciences of the USSR.

Squires, Todd M.; Quake, Stephen R.; "Microfluidics: Fluid Physics at the Nanoliter Scale"; Reviews of Modern Physics; bearing dates of Oct. 6, 2005 and Jul. 2005; pp. 977-1026; vol. 77; The American Physical Society.

Staiti, N.; Di Martino, D.; Saravo, L.; "A Novel Approach in Personal Identification From Tissue Samples Undergone Different Processes Through STR Typing"; Forensic Science International; Bearing a date of 2004; pp. S171-S173; vol. 146S; Elsevier Ireland Ltd.; located at: www.elsevier.com/locate/forsciint.

Stone, H.A.; Stroock, A.D.; Ajdari, A.; "Engineering Flows in Small Devices: Microfluidics Toward a Lab-on-a-Chip"; Annual Review of Fluid Mechanics; bearing a date of 2004; pp. 381-411, C1-C4; vol. 36; Annual Reviews; located at: arjournals.annualreviews.org.

Tate, Sarah K.; Goldstein, David B.; "Perspective: Will Tomorrow's Medicines Work for Everyone?"; Nature Genetics Supplement; Bearing a date of Nov. 2004; pp. S34-S42; vol. 36, No. 11; Nature Publishing Group; located at: http://www.nature.com/naturegenetics.

"The Mechanisms of Protein Stabilisation"; Company Technology Services Products; Bearing dates of 2001 and Nov. 9, 2001; pp. 1-3; Applied Enzyme Technology Ltd; located at: http://www.aetltd.com/tech/main.html.

"The Use of Enzymes in Detergents"; London South Bank University; Bearing a date of Dec. 20, 2004; pp. 1-4; located at: http://www.lsbu.ac.uk/biology/enztech/detergent.html.

"The World's Best DNase: Improved Turbo DNA-free"; Ambion TechNotes; Bearing a date of 2006; pp. 1-4; vol. 11, No. 4; Ambion, Inc.; located at: http://www.ambion.com/techlib/tn/114/10.html.

Umetsu, Kazuo; Yuasa, Isao; "Review Article: Recent Progress in Mitochondrial DNA Analysis"; Legal Medicine; Bearing a date of 2005; pp. 259-262; vol. 7; Elsevier Ireland Ltd.; located at: www.elsevier.com/locate/legalmed.

"What Destroys DNA?"; Sciforums.com: Science: Biology & Genetics; Bearing dates of Mar. 5, 2005-Mar. 7, 2005; pp. 1-6; located at: http://sciforums.com/showthread.php?p=779123.

"Bedbugs: Vampires of the Insect World"; Natural Ginesis; pp. 1-10; located at: http://www.naturalginesis.com/remove_bed_bugs_the_nontoxic_way_.htm; printed on Mar. 21, 2011.

(56) References Cited

OTHER PUBLICATIONS

Bríon, María; "Y Chromosome SNP Analysis Using Single-Base Extension: A Hierarchical Multiplex Design"; Methods in Molecular Biology: Forensic DNA Typing Protocols; 2005; pp. 229-242 (plus cover sheet—2 pgs.); vol. 297, Chapter 16; Humana Press Inc.

"Chemical Products"; American Brand Products; pp. 1-13; located at: http://www.americanchemical.net/chemical.htm; printed on Mar. 21, 2011.

"Detergents"; Novozymes; pp. 1-2; located at: http://www.novozymes.com/en/MainStructure/ProductsAndSolutions/Detergents/Detergents.htm; printed on Mar. 21, 2011.

"Dif Gel"; Zinsser; pp. 1-2; located at: http://www.zinsser.com/product_detail.asp?ProductID=18; printed on Mar. 21, 2011.

"DNAZap™ Solutions: PCR DNA Degradation Solutions Part No. AM9890"; Applied Biosystems; Revision C; Revision Date: Dec. 19, 2008; pp. 1-4; Ambion, Inc.

"Enzyme 309 XL Treatment and Cleaner"; ArroChem, Incorporated: Specialty and Industrial Chemicals; pp. 1-2; located at: http://www.arrochem.com/products/enzyme309xl.html; printed on Mar. 21, 2011.

"Enzyme Magic"; Enzyme Solutions, Incorporated: Retail Products; pp. 1-3; located at: http://www.enzymesolutions.com/retail_products.html; printed on Mar. 21, 2011.

* cited by examiner

FIG. 9

```
┌─────────────────────────────────────────────────────────────────────┐
│ 71 Controller Unit                                                  │
│                                                                     │
│  ┌──────────────────────────────┐  ┌──────────────────────────────┐ │
│  │ 72 One or more controller    │  │ 73 One or more controller    │ │
│  │ units optionally operable to │  │ units optionally operable to │ │
│  │ control one or more          │  │ control one or more          │ │
│  │ activities and/or functions  │  │ activities and/or functions  │ │
│  │ of one or more dispensing    │  │ of one or more sourcing      │ │
│  │ units                        │  │ units                        │ │
│  └──────────────────────────────┘  └──────────────────────────────┘ │
│                                                                     │
│  ┌──────────────────────────────┐  ┌──────────────────────────────┐ │
│  │ 74 One or more controller    │  │ 75 One or more controller    │ │
│  │ units optionally operable to │  │ units optionally operable to │ │
│  │ control one or more          │  │ control one or more          │ │
│  │ activities and/or functions  │  │ activities and/or functions  │ │
│  │ of one or more monitoring    │  │ of one or more remote-       │ │
│  │ units                        │  │ control units                │ │
│  └──────────────────────────────┘  └──────────────────────────────┘ │
└─────────────────────────────────────────────────────────────────────┘
```

100 — Accessing the first possible dataset in response to the first input

210

2110 Accessing the first possible dataset as being associated with data representative of one or more of percent sequence similarity or percent sequence identity with one or more target nucleic acid sequences, based on one or more characterizations stored in association with one or more elements of the first possible dataset 2111 Receiving a first request associated with the first possible dataset 2112 Receiving a first request associated with the first possible dataset, the first request selecting data representative of the one or more target biological material identifiers 2113 Receiving a first request associated with the first possible dataset, the first request selecting data representative of one or more of percent sequence similarity or percent sequence identity with one or more target nucleic acid sequences and/or one or more target amino acid sequences 2114 Receiving a first request associated with the first possible dataset, the first request determining one or more of percent sequence similarity or percent sequence identity with one or more target nucleic acid sequences and/or one or more target amino acid sequences 2115 Receiving a first request from a graphical user interface 2116 Receiving a first request from at least one submission element of a graphical user interface 2117 Receiving a first request from at least one submission element of a graphical user interface, the first request at least partially identifying one or more elements of the first possible dataset 2118 Receiving a first request from at least one submission element of a graphical user interface, the first request selecting one or more elements of the first possible dataset 2119 Receiving a first request from at least one submission element of a graphical user interface, the first request providing instructions identifying data representative of one or more of the one or more target biological material identifiers 2120 Receiving a first request from at least one submission element of a graphical user interface, the first request providing instructions identifying data representative of one or more of percent sequence similarity or percent sequence identity with one or more target nucleic acid sequences and/or one or more target amino acid sequences 2121 Receiving a first request from at least one submission element of a graphical user interface, the first request providing instructions determining one or more of percent sequence similarity or percent sequence identity with one or more target nucleic acid sequences and/or one or more target amino acid sequences 2122 Accessing the first possible dataset in response to a first request, the first request specifying data representative of one or more of the one or more target biological material identifiers and at least one other instruction

FIG. 15

Generating the first possible dataset in response to the first input — 310

3100 Generating the first possible dataset in response to the first input, including data representative of one or more of one or more target biological material identifiers

3101 Generating the first possible dataset in response to the first input, the first input including data representative of one or more of percent sequence similarity or percent sequence identity with one or more target nucleic acid sequences and/or one or more target amino acid sequences

3102 Generating the first possible dataset by associating data representative of one or more of the one or more target biological material identifiers with one or more elements of the first possible dataset

3103 Generating the first possible dataset by associating data representative of one or more of percent sequence similarity or percent sequence identity with one or more target nucleic acid sequences with one or more elements of the first possible dataset

3104 Generating the first possible dataset using a database management system engine that is configured to query a first database to retrieve the first possible dataset therefrom

3105 Generating the first possible dataset by corresponding data representative of one or more of the one or more target biological material identifiers with one or more elements of the first possible dataset

3106 Generating the first possible dataset by corresponding data representative of one or more of percent sequence similarity or percent sequence identity with one or more target nucleic acid sequences with one or more elements of the first possible dataset

3107 Receiving a first request associated with the first possible dataset

3108 Receiving a first request associated with the first possible dataset, the first request selecting data representative of one or more of the one or more target biological material identifiers

3109 Receiving a first request associated with the first possible dataset, the first request selecting data representative of one or more of percent sequence similarity or percent sequence identity with one or more target nucleic acid sequences and/or one or more target amino acid sequences

100

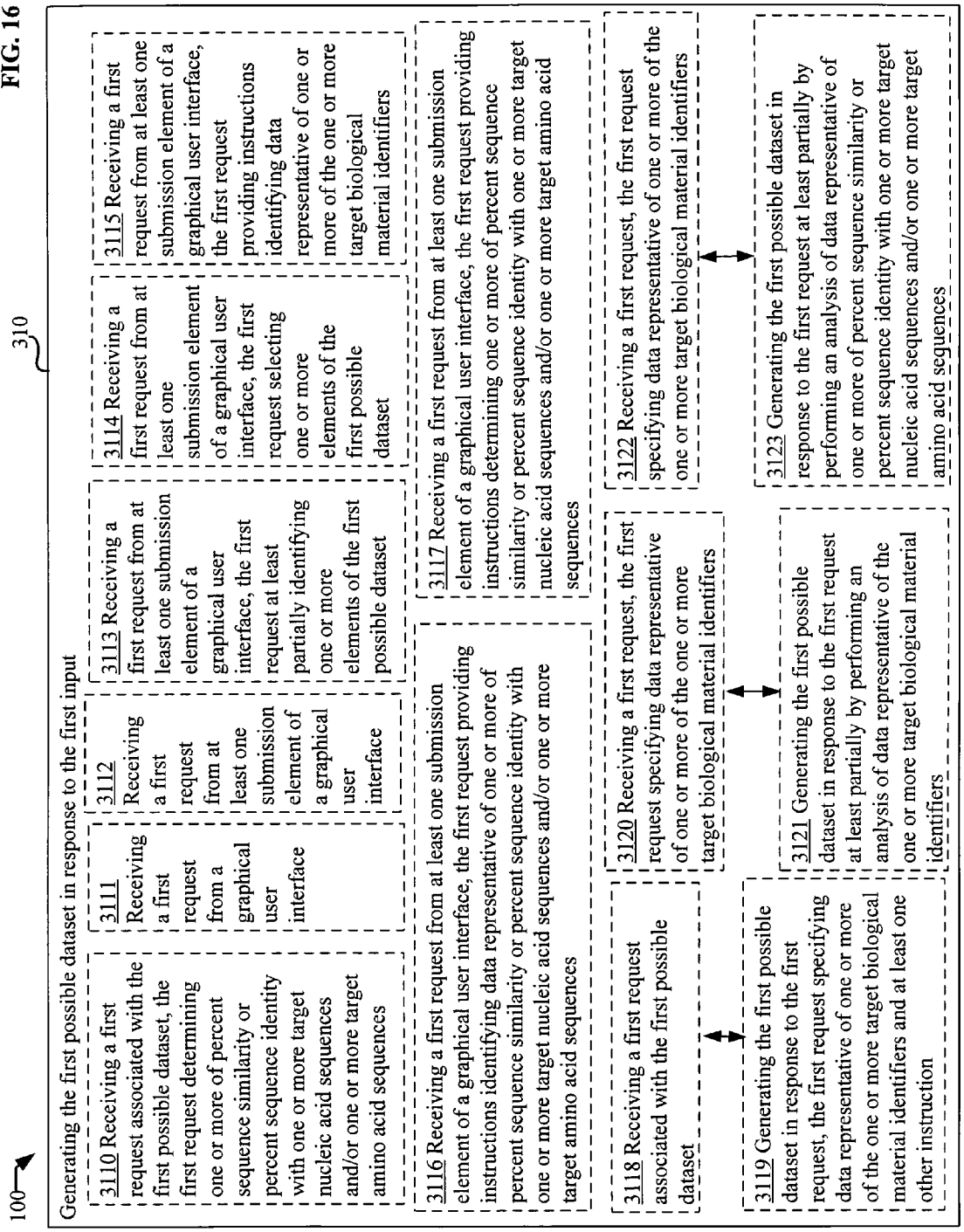

FIG. 21

DISEASES THAT DIFFER IN FREQUENCY BY RACE OR ETHNICITY
Halder (2003) Human Genomics 1:52-62

| Disease | High-risk groups | Low-risk groups |
|---|---|---|
| Obesity | African women, Native Americans South Asians, Pacific Islanders, Aboriginal Australians | Europeans |
| Non-insulin dependent diabetes | South Asians, West Africans, Peninsular Arabs, Pacific Islanders and Native Americans | Europeans |
| Hypertension | African Americans, West Africans | Europeans |
| Coronary heart disease | South Asians | West African men |
| End-stage renal disease | Native Americans and African populations | Europeans |
| Dementia | Europeans | African Americans, Hispanic Americans |
| Systemic lupus erythematosus | West Africans, Native Americans | Europeans |
| Skin cancer | Europeans | |
| Lung cancer | Africans, European Americans(Caucasians) | Chinese, Japanese |
| Prostate cancer | Africans and African Americans | |
| Multiple sclerosis | Europeans | Chinese, Japanese, African Americans, Turkmens, Uzbeks, Native Siberians, New Zealand Maoris |
| Osteoporosis | European Americans | African Americans |
| Atrial fibrillation | European-Americans | African-Americans |
| Carotid artery disease | European-Americans | African-Americans |
| Coronary artery disease | European-Americans | African-Americans |
| Dementia | African-Americans | European-Americans |
| End-stage renal disease | African-Americans | European-Americans |
| Focal segmental glomerulosclerosis | African-Americans | European-Americans |
| Hepatitis C clearance | European-Americans | African-Americans |
| HIV progression | African-Americans | European-Americans |
| HIV vertical transmission | European-Americans | African-Americans |
| Hypertensive heart disease | African-Americans | European-Americans |
| Hypertensive retinopathy | African-Americans | European-Americans |
| Intracranial haemorrhage | African-Americans | European-Americans |
| Lupus nephritis with systemic lupus erythematosus | African-Americans | European-Americans |
| Myeloma | African-Americans | European-Americans |
| Non-insulin dependent diabetes | African-Americans | European-Americans |
| Obesity/BMI | African-Americans | European-Americans |
| Pregnancy-related death | African-Americans | European-Americans |
| Stroke | African-Americans | European-Americans |
| Systemic lupus erythematosus | African-Americans | European-Americans |
| Systemic sclerosis | African-Americans | European-Americans |

SYSTEM FOR OBFUSCATING IDENTITY

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 11/510,754, entitled A SYSTEM FOR OBFUSCATING IDENTITY, naming W. Daniel Hillis, Nathan P. Myhrvold and Richa Wilson as inventors, filed 24 Aug. 2006 now U.S. Pat. No. 7,684,930, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/510,756 now U.S. Pat. No. 8,073,628, entitled A SYSTEM FOR OBFUSCATING IDENTITY, naming W. Daniel Hillis, Nathan P. Myhrvold and Richa Wilson as inventors, filed 24 Aug. 2006, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present applicant entity has provided above a specific reference to the application(s) from which priority is being claimed as recited by statute. Applicant entity understands that the statute is unambiguous in its specific reference language and does not require either a serial number or any characterization, such as "continuation" or "continuation-in-part," for claiming priority to U.S. patent applications. Notwithstanding the foregoing, applicant entity understands that the USPTO's computer programs have certain data entry requirements, and hence applicant entity is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

BRIEF DESCRIPTION OF THE FIGURES

FIG. 9 shows schematics of illustrative embodiments of the apparatus of FIG. 5, with illustrative examples of a controller unit.

FIG. 14 shows optional embodiments of the operational flow of FIG. 11.

FIG. 15 shows optional embodiments of the operational flow of FIG. 11.

FIG. 16 shows optional embodiments of the operational flow of FIG. 11.

FIG. 21 is a table describing diseases that differ in frequency by race or ethnicity.

DETAILED DESCRIPTION

Figure 1C:
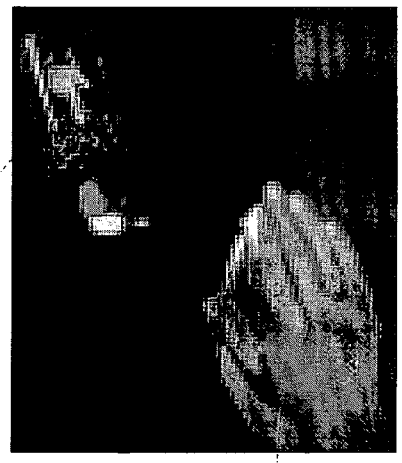
FIGS. 1A, 1B, and 1C show illustrative implementations of biological material identifiers obfuscating systems.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The present application relates, in general, to systems, apparatus, kits, devices, compositions, and methods of masking or degrading biological material identifiers. Those having skill in the art will appreciate that the specific systems, apparatus, kits, devices, compositions, and methods described herein are intended as merely illustrative of their more general counterparts.

The ability to mask and/or degrade biological material identifiers of individuals or groups is becoming increasingly desirable as cloning and DNA and protein-based methods of identification of individuals become commonplace. Identity theft no longer just involves credit cards, for example, but also theft of biological material, such as but not limited to, DNA and/or protein sequences that at least partially identify individuals and/or groups. Biological material identity theft could lead to non-permissive cloning of individuals and/or their tissues, or impact other privacy rights of individuals and groups relating to health care and disease, for example. Although the above-described examples are not intended to be (and should not be taken to be) in any way limiting, the present application describes systems, apparatus, kits, devices, compositions, and methods designed to address these and other related issues.

As used herein, the term "biological material identifier(s)" means any biological material of one or more biological entities, useful for identifying one or more of the one or more organisms. Biological material identifiers may include, but are not limited to, cells, skin, hair, fur, and/or secretions that optionally include, but are not limited to, saliva, semen, urine, blood, and feces, and optionally further include any biological materials of an organism containing one or more nucleic acids and/or one or more proteins. Biological material identifiers may also include, but are not limited to, one or more types of genetic information and/or genetic characteristics, including, but not limited to, single nucleotide polymorphisms, nucleic acid sequences, telomere length, alleles, genetic diseases, chromosomal duplications, deletions, inversions, and/or mitochondrial DNA, as well as other characteristics that reflect underlying genetic information, such as but not limited to, eye color, blood type, hair color and/or pattern, and optionally further including proteins and/or protein sequences that at least partially serve to identify an individual or population. Biological material identifiers may also include, but are not limited to, one or more of the ethnicity, race, demographic, population, geographic location and/or heritage and/or one or more other identifying characteristics.

As used herein, the term "biological entity" means one or more living entities including, but not limited to, plants, animals, microorganisms, prokaryotes, eukaryotes, protozoa, bacteria, mammals, yeast, *E. coli*, humans, reptile, bird, amphibian, and/or fish. The animals may include, but are not limited to, domesticated, wild, research, zoo, sports, pet, primate, marine, and/or farm animals. Animals include, but are not limited to, bovine, porcine, swine, ovine, murine, canine, avian, feline, equine, and/or rodent animals. Domesticated and/or farm animals include, but are not limited to, chickens, horses, cattle, pigs, sheep, donkeys, mules, rabbits, goats, ducks, geese, chickens, and/or turkeys. Wild animals include, but are not limited to, non-human primates, bear, deer, elk, raccoons, squirrels, wolves, coyotes, opossums, foxes, skunks, and/or cougars. Research animals include, but are not limited to, rats, mice, hamsters, guinea pigs, rabbits, pigs, dogs, cats and/or non-human primates. Pets include, but are not limited to, dogs, cats, gerbils, hamsters, guinea pigs and/or rabbits. Reptiles include, but are not limited to, snakes, lizards, alligators, crocodiles, iguanas, and/or turtles. Avian animals include, but are not limited to, chickens, ducks, geese, owls, sea gulls, eagles, hawks, and/or falcons. Fish include, but are not limited to, farm-raised, wild, pelagic, coastal, sport, commercial, fresh water, salt water, and/or tropical. Marine animals include, but are not limited to, whales, sharks, seals, sea lions, walruses, penguins, dolphins, and/or fish.

As used herein, the term "obfuscating component(s)" means one or more molecules useful for hiding the identity of one or more target biological material identifiers. Obfuscating components include, but are not limited to nucleic acid depositing components, protein depositing components, nucleic acid degrading components and protein degrading components.

As used herein the term "nucleic acid depositing components" means one or more molecules, cells and/or tissues that include, but are not limited to, nucleic acid, nucleic acid sequences, compositions including nucleic acids and/or nucleic acid sequences, and nucleic acids and/or nucleic acid sequences in one or more carriers and/or carrier components, including but not limited to, natural carriers such as skin, hair, biological fluids, and/or biological excretions. Nucleic acids may include one or more nucleic acids from one or more biological entities.

As used herein the term "protein depositing components" means one or more molecules, cells and/or tissues that include, but are not limited to, protein, protein sequences, compositions including proteins and/or protein sequences, and proteins and/or protein sequences in one or more carriers and/or carrier components, including but not limited to, natural carriers such as skin, hair, biological fluids, and/or biological excretions.

As used herein, the term "nucleic acid degrading components" means one or more molecules useful to decrease the size and/or amount of nucleic acid molecules. Degrading components may be enzymatic and/or non-enzymatic. The term "degrading" includes a measurable reduction in length, size, or amount. The nucleic acid may be fragmented, and/or at least partially broken into individual nucleotides, for example. Methods for measuring nucleic acid degradation are known in the art.

As used herein, the term "protein degrading components" means one or more molecules useful to decrease the size and/or amount of protein molecules. Degrading components may be enzymatic and/or non-enzymatic. Proteins may be fragmented, and/or at least partially broken into amino acids, or other substituent molecules. In some embodiments, protein degrading components include components with cell lysis and/or membrane lysis activity. Methods for measuring protein degradation are known in the art.

As used herein, the term "nucleic acid, nucleic acids, nucleic acid sequence, and/or nucleic acid sequences" means one or more complex, high-molecular-weight biochemical macromolecules composed of nucleotide chains. Nucleic acids include, but are not limited to, one or more forms of deoxyribonucleic acid (DNA), ribonucleic acid (RNA; includes messenger RNA (mRNA)), and complementary DNA (cDNA; DNA synthesized from an mRNA template). Nucleic acids may be optionally natural or non-natural. Nucleic acids may be optionally recombinant, purified, and/or isolated. Nucleic acid sequence(s) also refers the order of the nucleotides along one or more nucleic acid strands. Methods of determining nucleic acid sequences and synthesizing nucleic acids with target nucleic acid sequences are known in the art. In some embodiments, one or more nucleic acid sequences include, but are not limited to, those that encode one or more proteins, are transcribed into one or more RNA (including, but not limited to, rRNA, tRNA and/or siRNA), are regulatory sequences or repeating sequences, and/or have an at least partially undefined/unknown role. In some embodiments, one or more nucleic acid sequences include, but are not limited to, introns, exons, junk DNA, telomeres and centromeres, pseudogenes and/or hot-spots for duplication of short DNA regions.

As used herein, the term "peptide, peptides, protein, proteins" means polypeptide molecules formed from linking various amino acids in a defined order or amino acid sequence and include protein fragments. The link between one amino acid residue and the next forms a bond, including but not limited to an amide or peptide bond, or any other bond that can be used to join amino acids. The peptides/proteins may include any polypeptides of two or more linked amino acid residues. The peptides/proteins may include any polypeptides including, but not limited to, ribosomal peptides and non-ribosomal peptides. The peptides/proteins may include natural and unnatural amino acid residues. The proteins may be recombinant molecules or produced using recombinant methodology. Proteins and/or protein depositing components may include one or more proteins from one or more biological entities. Proteins may be glycosylated and/or phosphorylated. Proteins may include, but are not limited to, receptors, ligands, antibodies, cytokines, structural, regulatory, secreted, transmembrane, signal, mutated, variant, over-expressed, nuclear, cytoplastic, mitochondrial, viral, as well as other identifiable groupings.

As used herein, the term "natural" means something that may be found in nature. For example, natural nucleic acids would include nucleic acids as found in nature. Natural nucleic acids may include, but are not limited to, nucleic acids found in one or more biological materials and/or natural carriers. Natural proteins would include proteins as found in nature. Natural proteins may include, but are not limited to, proteins found in one or more biological materials and/or natural carriers.

As used herein, the term "natural carrier(s) or natural carrier components" mean something in which a biological material is found in nature. Natural carriers include, but are not limited to, cells, skin, hair, fur, and/or secretions that optionally include but are not limited to saliva, semen, urine, blood, and feces, and optionally further include any biological materials of an organism containing one or more nucleic acids and/or one or more proteins. Natural nucleic acids may be identified, selected and/or isolated, by identifying, selecting and/or isolating one or more biological material or natural carriers including the nucleic acids. Natural proteins may be identified, selected and/or isolated, by identifying, selecting and/or isolating one or more biological material or natural carriers including the proteins.

As used herein, the term "non-natural" means something that may not be found in nature. Non-natural nucleic acids would include, but are not limited to, at least partially recombinant, at least partially purified, and/or at least partially isolated nucleic acids. Non-natural nucleic acids may include, but are not limited to, nucleic acids found in one or more biological materials and/or natural carriers, and/or in one or more non-natural carriers. For example, recombinant nucleic acids may be introduced into one or more natural carriers such as, but not limited to, cells, by methods of transfection, transformation, or electroporation, for example, all of which are known to those of skill in the art. In another illustrative embodiment, recombinant, at least partially purified and/or at least partially isolated nucleic acids may be combined with one or more natural carriers, such as, but not limited to, biological secretions.

Non-natural proteins would include, but are not limited to, at least partially recombinant, at least partially purified, and/or at least partially isolated proteins. Non-natural proteins may include, but are not limited to, proteins found in one or more biological materials and/or natural carriers, and/or in one or more non-natural carriers. For example, recombinant proteins may be introduced into one or more natural carriers such as, but not limited to, cells, by methods of transfection, transformation, or electroporation of the encoding gene, for example, all of which are known to those of skill in the art. In another illustrative embodiment, recombinant, at least partially purified and/or at least partially isolated proteins may be combined with one or more natural carriers, such as, but not limited to, biological secretions.

As used herein, the term "non-natural carrier(s) or non-natural carrier component(s)" means a carrier that is not found in nature. In some embodiments, non-natural carriers may include, but are not limited to, buffers, powders, lotions, aerosol droplets, liposomes, gels, shampoos, beads, solutions, and other appropriate wet or dry carriers. One of skill in the art is able to determine appropriate non-natural carriers based on the teachings herein and in the art.

Some embodiments may include more than one carrier or carrier components (natural and/or non-natural). The one or more carriers or carrier components may be the same or different for different obfuscating components. The one or more carriers or carrier components may be designated "first", "second", "third", "fourth", "fifth", "sixth", "seventh", "eighth", "ninth", "tenth", and so on for clarity to indicate that the carrier may, or may not, be the same as other carriers. Labeling one or more carriers or carrier components with the same numeral may indicate the same or similar carrier unless context indicates otherwise.

As used herein, the term "recombinant" means a combination of molecules that are not found together in nature. Methods of recombination for biological molecules are known to one of skill in the art. Recombinant optionally refers to processes involving some element of human intervention to obtain a combination of molecules that are not found together in nature. The term recombinant may be used to describe nucleic acids, proteins, cells, tissues, or whole organisms, for example.

As used herein, the term "purified" means separated from non-selected materials. Materials may be partially or completely purified. Materials may be partially purified, such that there is a 10% to 100%, 10% to 95%, 10% to 90%, 10% to 85%, 10% to 75%, 10% to 60%, 10% to 50%, 10% to 40%, 10% to 25%, 20% to 100%, 20% to 95%, 20% to 90%, 20% to 75%, 20% to 50%, 40% to 100%, 40% to 95%, 40% to 75%, or 75% to 100% purification compared with the non-purified materials and/or the materials from which the material is to be purified. Materials may be partially purified, such that there is approximately a 5, 10, 20, 30, 40, 50, 60, 70, 80, 90, 95, 96, 97, 98, or 99 percent purification compared with the non-purified materials and/or the materials from which the material is to be purified. Purification may be determined by one or more methods known in the art for detecting the one or more materials present in a sample.

As used herein, the term "isolated" means separated from one or more non-selected materials. Materials may be partially or completely isolated. Materials may be partially isolated, such that there is a 10% to 100%, 10% to 95%, 10% to 90%, 10% to 85%, 10% to 75%, 10% to 60%, 10% to 50%, 10% to 40%, 10% to 25%, 20% to 100%, 20% to 95%, 20% to 90%, 20% to 75%, 20% to 50%, 40% to 100%, 40% to 95%, 40% to 75%, or 75% to 100% separation compared with the non-isolated materials and/or the materials from which the material is to be isolated. Materials may be partially isolated, such that there is approximately a 5, 10, 20, 30, 40, 50, 60, 70, 80, 90, 95, 96, 97, 98, or 99 percent separation compared with the non-purified materials and/or the materials from which the material is to be isolated. Selection or isolation may be determined by one or more methods known in the art, for detecting the one or more materials selected for and/or selected against.

As used herein, the term "sequence similarity" means a measure of the numbers of shared identical or similar nucleotides or amino acids among two or more nucleic acid sequences or protein sequences, respectively. A "percent sequence similarity" provides this comparison calculated as a percentage. For example, a target nucleotide sequence or target amino acid sequence may share 10% to 100%, 10% to 95%, 10% to 90%, 10% to 85%, 10% to 75%, 10% to 60%, 10% to 50%, 10% to 40%, 10% to 25%, 20% to 100%, 20% to 95%, 20% to 90%, 20% to 75%, 20% to 50%, 40% to 100%, 40% to 95%, 40% to 75%, or 75% to 100% percent similarity with one or more nucleotide sequences or amino acid sequences, respectively. A target nucleotide sequence or target amino acid sequence may share approximately a 5, 10, 20, 30, 40, 50, 60, 70, 80, 90, 95, 96, 97, 98, or 99 percent similarity with one or more nucleotide sequences or amino acid sequences, respectively.

As used herein, the term "sequence identity" means a measure of the numbers of shared identical nucleotides among two or more nucleic acid sequences or protein sequences, respectively. A "percent sequence identity" provides this comparison calculated as a percentage. For example, a target nucleotide sequence may share 10% to 100%, 10% to 95%, 10% to 90%, 10% to 85%, 10% to 75%, 10% to 60%, 10% to 50%, 10% to 40%, 10% to 25%, 20% to 100%, 20% to 95%, 20% to 90%, 20% to 75%, 20% to 50%, 40% to 100%, 40% to 95%, 40% to 75%, or 75% to 100% percent identity with one or more nucleotide sequences or amino acid sequences, respectively. A target nucleotide sequence or target amino acid sequence may share approximately a 5, 10, 20, 30, 40, 50, 60, 70, 80, 90, 95, 96, 97, 98, or 99 percent identity with one or more nucleotide sequences or amino acid sequences, respectively.

Methods of determining percent sequence similarity and/or percent sequence identity are known in the art. A sequence alignment in bioinformatics is a way of arranging DNA, RNA, or protein primary sequences to emphasize their regions of similarity. Sequences are typically written with their characters (generally amino acids or nucleotides) in aligned columns into which gaps are inserted so that successive columns contain identical or similar characters. Very short or very similar sequences can be aligned by hand; however, the alignment of lengthy, highly variable, or extremely numerous sequences is obtained using algorithms for producing high-quality sequence alignments. Computational approaches to sequence alignment include global alignments and local alignments. Calculating a global alignment is a form of global optimization that "forces" the alignment to span the entire length of all query sequences. By contrast, local alignments identify regions of similarity within long sequences that are often widely divergent overall. A variety of computational algorithms have been applied to the sequence alignment problem, including dynamic programming.

As used herein, the term "genome" means the whole hereditary information of an organism that is encoded in the DNA (or, for some viruses, RNA including both the genes and the non-coding sequences. The genome may be a complete DNA sequence of one set of chromosomes of an organism; for example, one of the two sets that a diploid individual carries in every somatic cell. In some embodiments, one or more genomes may include, but not be limited to, nuclear, organellar, chloroplast and/or mitochondrial. One or more genomes may refer to an individual, one or more individuals, a species, one or more species, a group of individuals within a species, one or more groups of individuals within a species, a class of individuals within a species, or one or more classes of individuals within a species.

As used herein, the term "proteome" means the complement of proteins in a given biological organism or system at a given time. The proteome also includes subsets, such as but not limited to, cellular proteomes, the collection of proteins found in a particular cell type under a particular set of environmental conditions, as well as mitochondrial or viral proteomes. Proteomes may also reflect alternative splicing of genes and post-translational modifications like glycosylation or phosphorylation.

As used herein, the term "chromosome(s)" means the nucleic acids that carry genetic information in cells packaged in the form of one or more large macromolecules. A chromosome is a very long, continuous piece of nucleic acid (DNA) that contains many genes, regulatory elements and other intervening nucleotide sequences. In the chromosomes of eukaryotes, the uncondensed DNA exists in a quasi-ordered structure inside the nucleus, where it wraps around histones, and where this composite material is called chromatin. Prokaryotes do not possess histones or nuclei. In its relaxed state, the DNA can be accessed for transcription, regulation, and replication.

As used herein, the term "ethnic group or ethnic groups" means a human population whose members identify with each other, optionally on the basis of a presumed common genealogy or ancestry. Ethnic groups may be united by common cultural, behavioral, linguistic, and/or religious practices. Ethnic groups may be endogamous populations when members of an ethnic group procreate primarily with other members of their ethnic group, something which is measurable in terms of characteristic average genetic frequencies. These differences, however, usually do not approach the magnitude of racial difference in that the genetic differences within an ethnic group are greater than the difference between any two ethnic groups.

As used herein, the term "racial group or racial groups" means one population of humans (or non-humans) that are distinguished from another. Human racial categories include, but are not limited to, visible traits (especially skin color and facial features), genes, and self-identification. Biomedicine in the U.S. frequently separates five races: black or African American, white, Asian, native Hawaiian or other Pacific Islander, and American Indian or Alaska native.

In an illustrative example, genetic research has shown that the greatest genetic differentiation among humans corresponds with continental groupings. In general, genetic clusters exist that correspond tightly to the census definition of race and to self-identified ancestry. In illustrative embodiments, one or more methods may include obfuscating one or more target biological material identifiers by providing one or more nucleic acid sequences to an environment, wherein the one or more nucleic acids are associated with the same or similar race, ancestry, and/or continental grouping, and/or associated with a different or unrelated race, ancestry, and/or continental grouping.

Race is associated with differential disease susceptibility and environmental responses. Many highly penetrant Mendelian diseases that are caused by mutations in a single gene are known to be found at higher frequencies in certain races. The HbS allele that causes haemochromatosis is found at higher frequencies in sub-Saharan Africans and Southern Europeans. Similarly, the ΔF508 allele of CFTR that causes cystic fibrosis is found in higher frequencies in Northern Europeans. In illustrative embodiments, one or more methods may include obfuscating one or more target biological material identifiers by providing one or more nucleic acid sequences to an environment, wherein the one or more nucleic acids contain, or do not contain, one or more mutations in one or more genes found at higher frequencies in certain races.

Race has also been found to be associated with susceptibility to complex, multifactorial and multigenic diseases. The incidence and death rate of prostate and breast cancers are significantly higher in African-Americans than European-Americans. Higher proportions of individual African ancestry are associated with increased susceptibility to both obesity and abnormal levels of insulin secretion. Likewise, Hispanic, American Indian, African American, Pacific Island, and South Asian ancestry is considered a risk factor for diabetes. Also, the incidence of heart disease and high blood pressure is higher in African-Americans than European-Americans.

Racial and ethnic groups can exhibit substantial average differences in disease incidence, disease severity, disease progression, and response to treatment. Differences in allele frequencies contribute to group differences in the incidence of some monogenic diseases, and they may contribute to differences in the incidence of some common diseases (Genome Biol. (2002) 3:comment2007; New England J. of Med. (2003) 348:1170-1175; Nature Genetics Suppl. (2004) 36:S34-S42). FIG. 21 is a table describing diseases that differ in frequency by race or ethnicity (Human Genomics (2003) 1:52-62).

For the monogenic diseases, the frequency of causative alleles usually correlates best with ancestry, whether familial (for example, Ellis-van Creveld syndrome among the Pennsylvania Amish), ethnic (Tay-Sachs disease among Ashkenazi Jewish populations), or geographical (hemoglobinopathies among people with ancestors who lived in malarial regions). Even with common diseases involving numerous genetic variants and environmental factors, investigators point to evidence suggesting the involvement of differentially distributed alleles with small to moderate effects. Frequently cited examples include hypertension (J. Assoc. Acad. Minor. Phys. (1996) 7:16-21), diabetes (Diabetes (2003) 52:1047-1051), obesity (Obes. Res. (2003) (11):904-911), and prostate cancer (J. National Cancer Inst. (2000) 92:2009-2017).

As used herein the term "demographic group or demographic groups" means a market segment. Market segments optionally include, but are not limited to, age bands, social class bands and/or gender. In illustrative embodiments, one or more methods may include obfuscating one or more target biological material identifiers by providing one or more nucleic acid sequences to an environment, wherein the one or more nucleic acids are associated with the same or similar age, social class, and/or gender, and/or associated with a different or unrelated age, social class, and/or gender. Nucleic acids associated with age would include for example, telomeres, which are known to decrease in length as humans age. Nucleic acids associated with gender would include, but not be limited to, a variety of genes on the X or Y chromosomes.

As used herein, the term "wide area dispensing apparatus" means any device capable of a generalized release of obfuscating components over a broad area. In some embodiments, the broad area is an environment. In some embodiments, a wide-area dispensing apparatus does not include a sprayer.

As used herein, the term "environment" means one or more identifiable locations, e.g. a position in space and time that can be determined. In some embodiments, one or more environments are discrete areas, amorphous areas, overlapping areas, particular locations, parts (or all) of rooms/hallways/entryways/porches/patios/garages and the like, parts (or all) of buildings/structures/planes/boats and the like, public, private, semi-public, partially public, enclosed, open, partially enclosed, and/or other appropriate environments. In some embodiments, one or more of the processes and/or elements of processes may occur at one or more identifiable locations or environments that may be the same or may be different. In some embodiments the terms, "first", "second", "third", "fourth", "fifth", "sixth", etc. may be used to indicate that the identifiable locations are optionally different identifiable locations or environments. Generally, identifiable locations or environments indicated by the same numeral are the same locations unless context indicates otherwise.

As used herein, the term "obfuscating" means one or more processes used to hide the presence of one or more biological material identifiers and/or to render the identity of the biological material identifiers very hard to read and understand. In an illustrative example, one or more target nucleic acid sequences are optionally obfuscated by providing one or more obfuscating nucleic acid sequences, one or more obfuscating protein sequences, one or more nucleic acid degrading components and/or one or more protein degrading components. In some embodiments, the one or more obfuscating nucleic acids, and/or one or more obfuscating protein sequences, may be deposited in an environment before, after, or concurrently with the one or more nucleic acid degrading components and/or the one or more protein degrading components. In some embodiments, the one or more nucleic acid degrading components and/or the one or more protein degrading components reduce the amount or percent of one or more nucleic acids sequences, and/or one or more protein sequences, present in an environment. In some embodiments, the nucleic acids, and/or proteins, are at least partially removed, reduced and/or eliminated from an environment.

As used herein, the term "depositing" means one or more process used to add one or more components to an environment. The term depositing may also include, but is not limited to, providing and/or releasing one or more components to an environment. In some illustrative embodiments, the method includes depositing one or more obfuscating components, optionally nucleic acids and/or proteins, in an environment.

As used herein, the term "providing" means one or more process resulting in one or more components being released. By "released" is meant extruded, propelled, spilled out, flowed, ejected, seeped, or other similar processes. Mechanisms for "providing" include, but are not limited to gravity-feed, aerosol, air pressure, detonation, fluid flow, fluid pressure, gas pressure, explosion, mechanical pressure, pump, and/or electrical pump, or other similar processes.

As used herein, the term "reducing" means one or more process used to at least partially decrease the amount of one or more components in an environment. Reducing may include, but is not limited to, removing, consuming and/or eliminating one or more components in an environment. The process may be a general one, or a specific one. In illustrative embodiments, one or more methods include at least partially removing nucleic acids, and/or proteins, in general from an environment. In illustrative embodiments, one or more methods include at least partially removing one or more specific nucleic acid sequences, and/or one or more specific protein sequences, from an environment. Methods for at least partially removing nucleic acids or nucleic acid sequences from an environment include, but are not limited to, providing one or more nucleic acid degrading components and/or providing one or more protein degrading components. Methods for at least partially removing proteins or protein sequences from an environment include, but are not limited to, providing one or more protein degrading components.

As used herein, the term "sequentially" when modifying processes, such as, the processes including, for example, providing, depositing, releasing, reducing, and/or eliminating, means any process that includes a temporal aspect such that the process acts upon one or more components at subsequent times. Sequentially may include, but is not limited to, any process that acts upon one or more components in a defined order. Sequentially may include, but is not limited to, any process that acts on one or more components one after another.

Generic processes useful for providing and/or depositing one or more obfuscating components to an environment, and including sequential processes, are known in the art and include, but are not limited to, one or more of automated methods, mechanical methods, computer and/or software-controlled methods, and fluid flow. Fluid flow includes, but is not limited to, nanofluidics and microfluidics. Nanofluidics and microfluidics include, but are not limited to, continuous flow microfluidics and digital microfluidics, and have been developed for use in biological systems (Annu. Rev. Fluid Mech. (2004) 36:381-411; Annu. Rev. Biomed. Eng. (2002) 4:261-86; Science (1988) 242:1162-1164, Rev. Mod. Phys. (2005) 77:977-1026).

As used herein, the term "identifying" means one or more process used to determine and/or select one or more "items" for use, wherein the one or more "items" optionally include, but are not limited to, one or more target components, one or more obfuscating components, one or more biological material identifiers, one or more nucleic acid sequences, one or more protein sequences, one or more populations, one or more genetic characteristics, etc. and/or other "items" that are appropriate when read in the context in which they occur in the description. Processes include, but are not limited to, user selected, user identified, user determined, software method analysis, algorithm-based, computer mediated, operations research, optimization, simulation, queuing theory, and/or game theory.

As used herein, the term "selecting" means one or more process used to identify for use one or more one or more "items", wherein the one or more "items" optionally include, but are not limited to, one or more target components, one or more obfuscating components, one or more biological material identifiers, one or more nucleic acid sequences, one or more protein sequences, one or more populations, one or more genetic characteristics, etc. and/or other "items" that are appropriate when read in the context in which they occur in the description. Processes include, but are not limited to, user selected, user identified, user determined, software method analysis, algorithm-based, computer mediated, operations research, optimization, simulation, queuing theory, and/or game theory.

As used herein, the term "co-localizing or providing or assembling" means any process resulting in one or more obfuscating components and/or one or more carrier components being in the same place at the same time. By "in the same place at the same time" is meant physical proximity such that the one or more components are capable of interaction and/or touching and/or mixing on a molecular level. Co-localizing may include, commingling, combining, mixing, assembling, aggregating, injecting, or other similar processes.

As used herein, the term "genotyping" means one or more process of determining the genotype of one or more individuals and/or groups with a biological assay. Methods of genotyping include, but are not limited to, PCR, DNA sequencing, and hybridization to DNA chips or beads. In illustrative embodiments, short tandem repeats, microsatellite DNA, mitochondrial DNA, and/or single nucleotide polymorphisms may be used for genotyping (Forensic Sci. Int. (2004) 146 suppl:S171-3; Forensic Sci. Int. (2005) 50:519-525; Forensic Sci. Int. (2005) 153:237-246; Forensic Sci. Int. (2005) 153:247-259; Forensic Sci. Int. (2005) 154:111-121; Forensic Sci. Int. (2005) 154:181-194; Forensic Sci. Int. (2005) 154:128-136; Forensic Sci. Int. (2006) 157:23-35; Int. J. Legal Med. (2005) 119:10-15; Methods Mol. Biol. (2005) 297:229-242; Electrophoresis (2005) 26:4411-4420; Leg. Med. (Tokyo) (2005) 7:259-262)

As used herein, the term "synchronizing" means any one or more processes coordinating one or more elements of one or more methods. The one or more elements of one or more methods may include, but are not limited to, one or more of two or more processes, or one or more processes and one or more target nucleic acid sequences. The one or more processes may include, but are not limited to, user defined, software-based, algorithm-based, computer mediated, operations research, optimization, simulation, queuing theory, and/or game theory.

As used herein, the term "identifiable time interval" means a discrete amount of time that is optionally knowable, determinable, and/or calculable. The term "one or more identifiable time intervals", is used herein to indicate time intervals for one or more processes. The one or more identifiable time intervals may be the same or different for different processes and/or elements of processes. The one or more identifiable time intervals may be the same or different for the release of one or more obfuscating components. One of skill in the art is able to determine appropriate one or more identifiable time intervals based on the teachings herein and in the art. The one or more identifiable time intervals may be designated "first", "second", "third", "fourth", "fifth", "sixth", "seventh", "eighth", "ninth", "tenth", and so on for clarity to indicate that the time interval may, or may not, be the same as other time intervals. Labeling one or more time intervals with the same numeral may indicate the same or similar time intervals unless context indicates otherwise.

The disclosure describes, inter alia, systems for obfuscating biological material identifiers. The obfuscating systems provide one or more obfuscating components, optionally selected from the group consisting of nucleic acid depositing components, protein depositing components, nucleic acid degrading components, and/or protein degrading components, to one or more environments. FIG. 1, FIG. 2, FIG. 3 and FIG. 4 show illustrative implementations of one or more systems for obfuscating biological material identifiers.

Figure 1B:
Figure 1A:
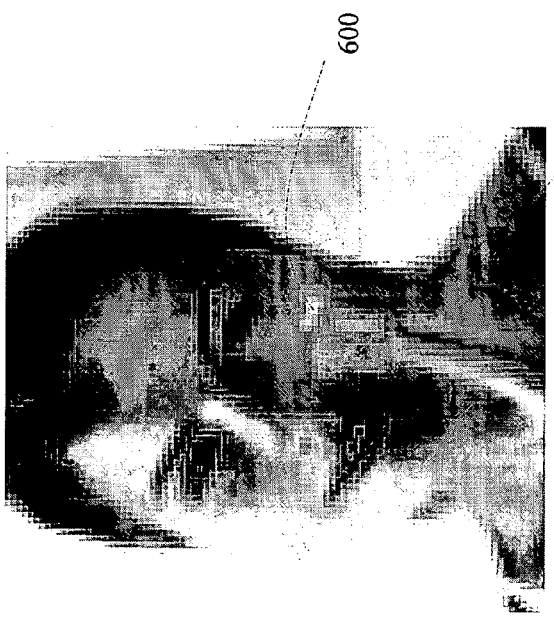

FIGS. 1A, 1B, and 1C show three illustrative implementations of one or more systems for obfuscating biological material identifiers using one or more compositions including one or more obfuscating components and optionally one or more carrier components. In some illustrative implementations, the one or more compositions are available as one or more topical applications 600, such as, but not limited to, a lotion, gel, crème, or shampoo, optionally from a focused area dispensing device 604. The user may apply the topical application on a body part 602, such as, but not limited to, skin and/or hair. In some illustrative embodiments, one or more compositions may be used to deposit one or more obfuscating components, such as one or more nucleic acid sequences, and/or one or more protein sequences, on one or more body parts. In some illustrative embodiments, one or more compositions may be used to deposit one or more obfuscating components, such as one or more nucleic acid degrading components and/or one or more protein degrading components on one or more body parts.

Figure 2:
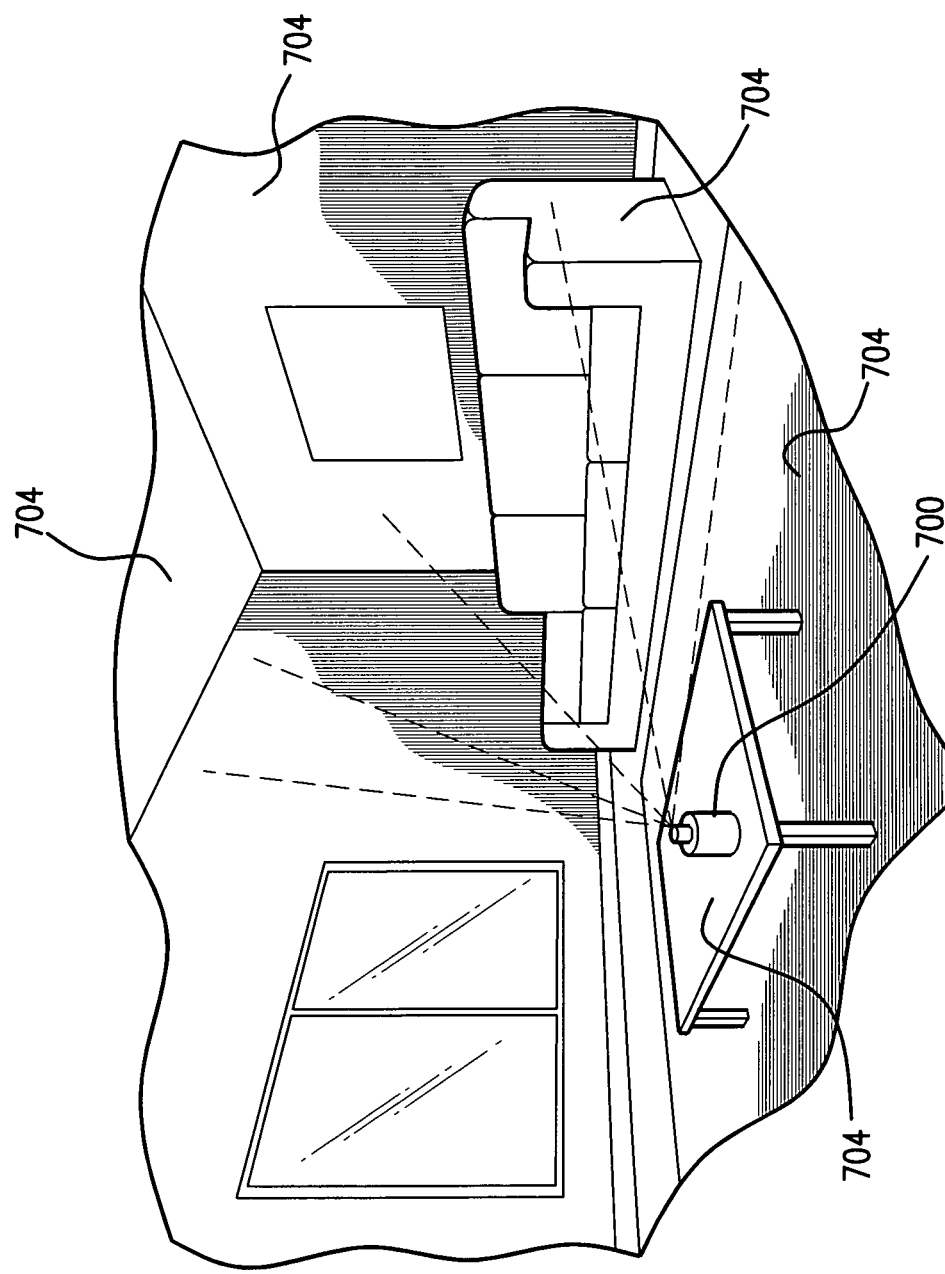
FIG. 2 shows an illustrative implementation of a biological material identifiers obfuscating system.
Figure 3:
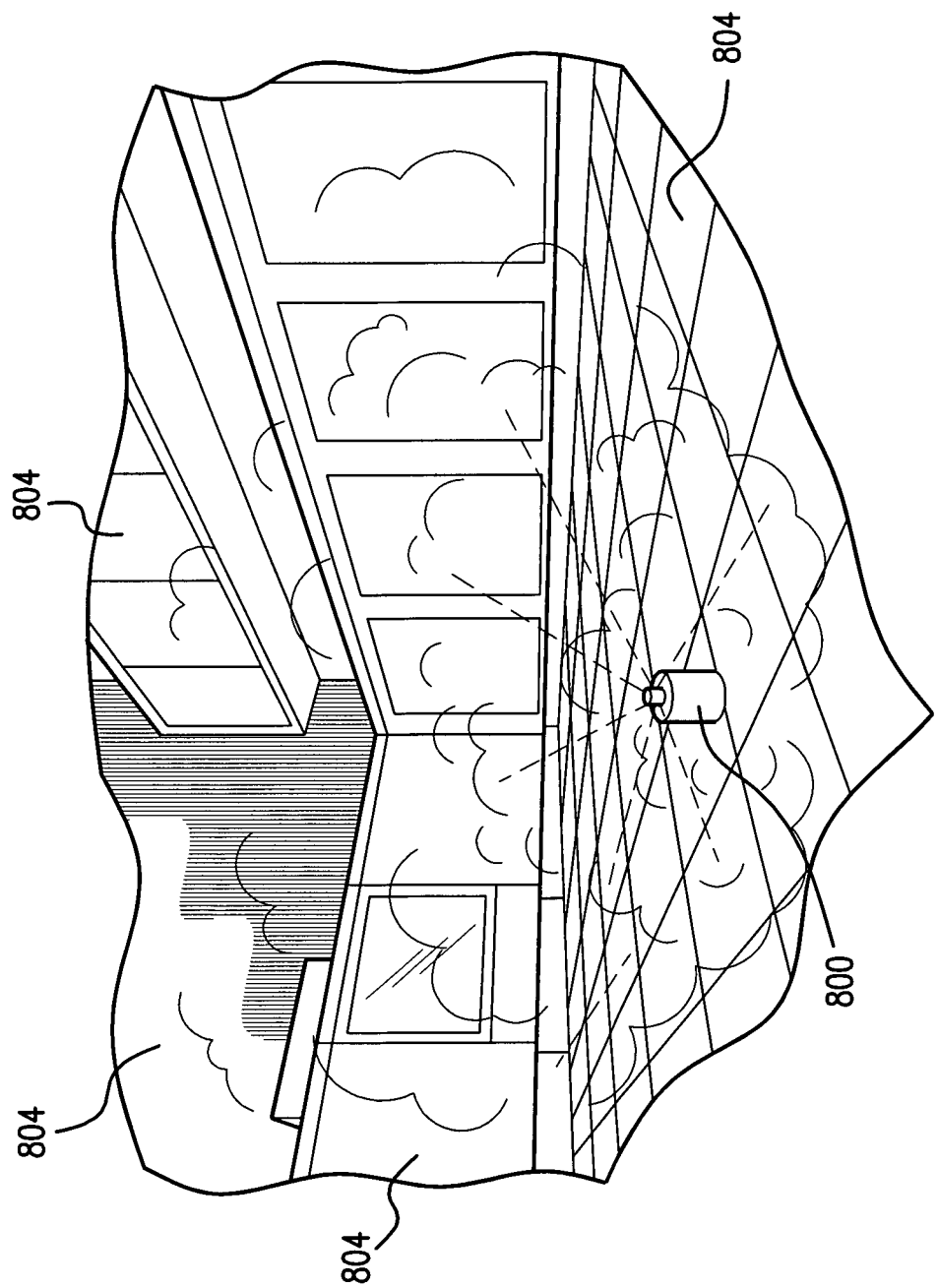
FIG. 3 shows an illustrative implementation of a biological material identifiers obfuscating system.
Figure 4:
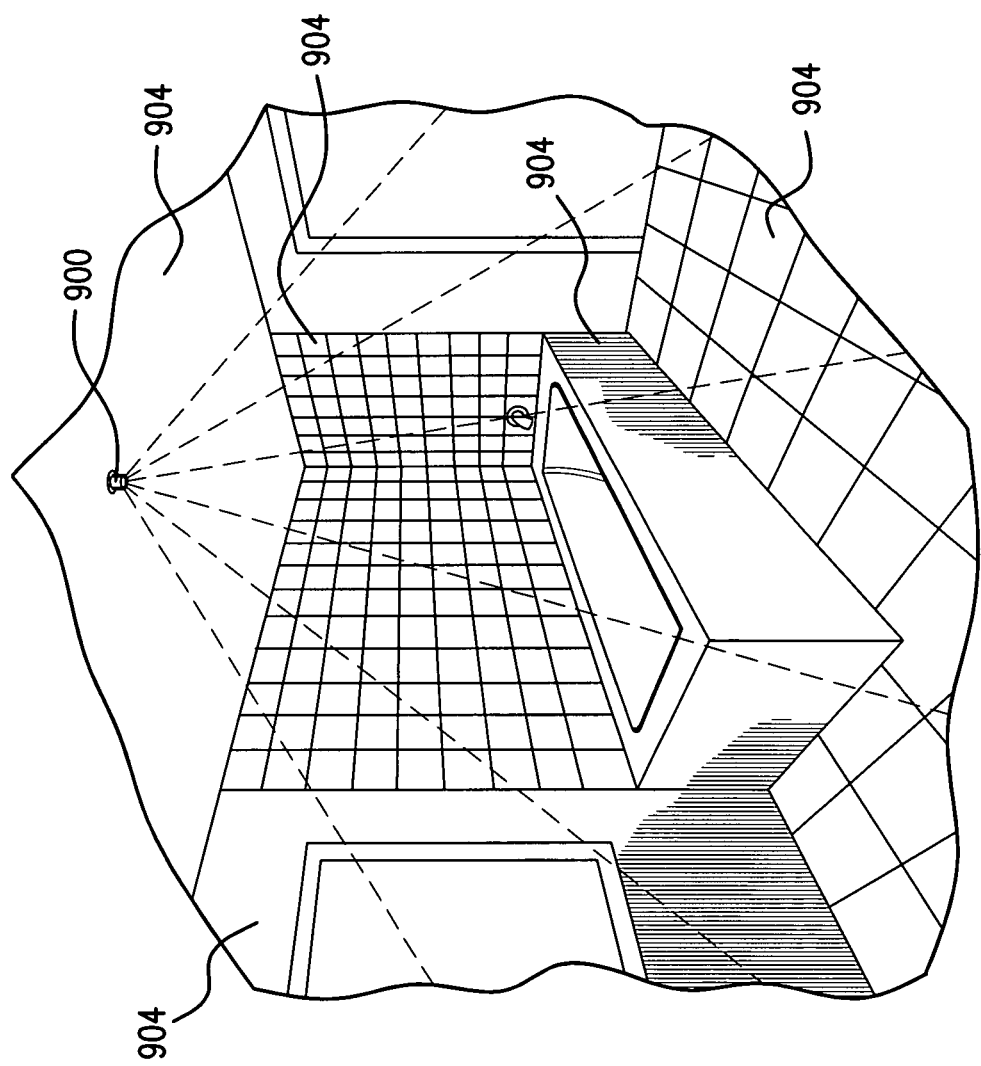
FIG. 4 shows an illustrative implementation of a biological material identifiers obfuscating system.

FIG. 2 shows an illustrative implementation of a system for obfuscating one or more biological material identifiers using one or more compositions including one or more obfuscating components and optionally one or more carrier components. In some illustrative implementations, the one or more compositions are available as one or more spray applications optionally for use in a focused area dispensing device 700. The one or more focused area dispensing device may be hand-held, and used to provide one or more obfuscating compositions to one or more specific areas including, but not limited to, one or more portions of rooms 704 such as, but not limited to, walls, flooring, carpets, ceilings, furniture and/or appliances.

FIG. 3 and FIG. 4 show illustrative implementations of a system for obfuscating one or more biological material identifiers using one or more compositions including one or more obfuscating components and optionally one or more carrier components. In some illustrative implementations, the one or more compositions are available as one or more misting, sprinkling, and/or fogging applications optionally for use in one or more wide-area dispensing devices 800 and/or 900. The one or more wide-area dispensing devices 800 and/or 900 may be stand-alone or mounted, single or multiple-use, and used to provide one or more obfuscating compositions to one or more environments. In some embodiments, the one more wide-area dispensing devices 800 and/or 900 are used to provide one or more obfuscating compositions to one or more rooms and their contents 804 and 904, including but not limited to, floors, ceilings, walls, counters, fixtures, and appliances. In some embodiments, the one more wide-area dispensing devices 800 and/or 900 have a 360 degree radius for providing one or more obfuscating compositions.

In one aspect, the disclosure is drawn to one or more compositions comprising one or more obfuscating components and optionally one or more carrier components. Methods for assembling and/or formulating one or more compositions in one or more forms optionally for cosmetic, pharmaceutical, nutraceutical, detergent, cleaning, and/or environmental uses are described herein and/or known in the art.

In some embodiments, the one or more obfuscating components include one or more nucleic acid depositing components, one or more protein depositing components, one or more nucleic acid degrading components and/or one or more protein degrading components. In some embodiments, the one or more carrier components include one or more first carriers for the one or more nucleic acid depositing components, one or more fourth carriers for the one or more protein depositing components, one or more second carrier components for the one or more nucleic acid degrading components, and/or one or more third carrier components for the one or more protein degrading components.

In some embodiments, the one or more first carrier components are the same as, or different from, the one or more fourth carrier components, the one or more second carrier components and/or the one or more third carrier components. In some embodiments, the one or more second carrier components are the same as, or different from, the one ore more first carrier components, the one or more fourth carrier components, and/or the one or more third carrier components. In some embodiments, the one or more third carrier components are the same as, or different from, the one or more first carrier components, the one or more fourth carrier components, and/or the one or more second carrier components. In some embodiments, the one or more fourth carrier components are the same as, or different from, the one or more first carrier components, the one or more second carrier components and/or the one or more third carrier components.

In some embodiments, the one or more compositions are formulated for focused dispensing, optionally using, but not limited to, one or more of a sprayer, an aerosol can, a bottle with plunger, and/or extrusion from a tube. In some embodiments, the one or more compositions are formulated for wide dispersion optionally using, but not limited to, one or more of a fogger, a bomb, a sprinkler, a grenade, or a mister.

In some embodiments, one or more compositions are optionally hypoallergenic, pharmaceutical grade, household grade, non reactive, or pet friendly. In some embodiments, one or more compositions may be topically applied, including but not limited to, as a lotion, a cream, a spray, or a shampoo. In some embodiments, one or more compositions and/or one or more obfuscating components may be applied to the environment as part of, for example, a floor cleaner, a rug cleaner, a device cleaner, a room spray, an upholstery cleaner or a laundry detergent. In some embodiments, the one or more compositions may have the consistency of, for example, a gel, cream, lotion, powder, aerosol, liquid, or a solid. In some embodiments, one or more compositions are formulated as pellets and/or grains which may optionally be scattered in the environment.

In some embodiments, one or more compositions include one or more surface tension reducing agents, and/or an emulsifier, such as, for example, a surfactant or a detergent. In some embodiments, one or more compositions may include a carrier for optimal suspension of the one or more obfuscating components. In some embodiments, the carrier may be of pharmaceutical grade, household grade, or cosmetic grade. Examples of acceptable carriers include, but are not limited to, PEG, starch, or polymers.

In some embodiments, the one or more compositions may include one or more obfuscating components and/or one or more carrier components that are optionally tagged such that they can be detected optionally by the addition of one or more additional components and or the use of one or more additional devices. In some embodiments, the one or more compositions may include one or more detectable dyes. The tagging or the inclusion of the dye is optionally useful to demarcate the presence of the one or more components and/or compositions, the quantity of the one or more obfuscating components, or the activity level of one or more of the enzymatic components. In some embodiments, the tagged components and/or dyed compositions are useful to optionally identify the presence or absence, quantity, and/or identity of one or more nucleic acid sequences and/or one or more target nucleic acid sequences. Methods of tagging one or more components and or dyes for detection are known in the art.

In some embodiments, one or more first compositions include one or more nucleic acid depositing components and one or more first carrier components. In some embodiments, one or more of the one or more first compositions are formulated for wide area dispersion, optionally from one or more of a fogger, a sprinkler, a grenade, or a mister. In some embodiments, one or more of the one or more first compositions are formulated for focused dispensing, optionally from one or more of a sprayer, an aerosol can, a bottle with plunger, and/or extrusion from a tube.

In some embodiments, one or more first compositions may include one or more components for maintaining the nucleic acid depositing components in a non-degraded form. The one or more components may include, but are not limited to, chemicals, chemical compounds, macromolecules, and/or agents that reduce the degradation of the nucleic acid depositing components, including but not limited to, one or more nucleic acid sequences, and/or one or more skin, hair, and/or biological fluid components.

In some embodiments, the one or more nucleic acid depositing components include one or more nucleic acid sequences that are optionally purified, isolated, and/or separated from non-nucleic acid biological material. In some embodiments, the one or more nucleic acid depositing components include one or more nucleic acid sequences in one or more biological materials, such as, but not limited to, hair, skin, and biological fluids, that have been at least partially purified, separated, isolated, and/or selected from non-selected biological materials. In some embodiments, the one or more first carriers are natural and/or non-natural.

In some embodiments, the one or more nucleic acid sequences share 5% to 99% sequence identity and/or similarity with one or more target nucleic acid sequences. In some embodiments, the one or more nucleic acid sequences are selected at least partially based on information associated with target biological material identifiers and/or target nucleic acid sequences, including but not limited to, ethnic, racial and/or demographic identity and/or one or more genetic characteristics and/or aberrations.

In some embodiments, one or more fourth compositions include one or more protein depositing components and one or more fourth carrier components. In some embodiments, one or more of the one or more fourth compositions are formulated for wide area dispersion, optionally from one or more of a fogger, a sprinkler, a grenade, or a mister. In some embodiments, one or more of the one or more fourth compositions are formulated for focused dispensing, optionally from one or more of a sprayer, an aerosol can, a bottle with plunger, and/or extrusion from a tube.

In some embodiments, one or more fourth compositions may include one or more components for maintaining the protein depositing components in a non-degraded form. The one or more components may include, but are not limited to, chemicals, chemical compounds, macromolecules, and/or agents that reduce the degradation of the protein depositing components, including but not limited to, one or more protein sequences, and/or one or more skin, hair, and/or biological fluid components.

In some embodiments, the one or more protein depositing components include one or more protein sequences that are optionally purified, isolated, and/or separated from non-protein biological material. In some embodiments, the one or more protein depositing components include one or more protein sequences in one or more biological materials, such as, but not limited to, hair, skin, and biological fluids, that have been at least partially purified, separated, isolated, and/or selected from non-selected biological materials. In some embodiments, the one or more fourth carriers are natural and/or non-natural.

In some embodiments, the one or more protein sequences share 5% to 99% sequence identity and/or similarity with one or more target protein sequences. In some embodiments, the one or more protein sequences are selected at least partially based on information associated with target biological material identifiers and/or target protein sequences and/or ethnic, racial and/or demographic identity and/or one or more genetic characteristics and/or aberrations.

In some embodiments, one or more second compositions comprise one or more nucleic acid degrading components and one or more second carrier components, the one or more second compositions formulated for wide area dispersion, optionally from one or more of a fogger, a sprinkler, a grenade, or a mister. In some embodiments, one or more of the one or more second compositions are formulated for focused dispensing, optionally from one or more of a sprayer, an aerosol can, a bottle with plunger, and/or extrusion from a tube. In some embodiments, the one or more first compositions and the one or more second compositions are the same composition.

In some embodiments, the nucleic acid degrading component and/or the nucleic acid hydrolyzing component may include, for example, one or more of a nucleic acid degrading component with substrate specificity, a nucleic acid degrading component with general specificity, sugar non specific nucleases, restriction endonucleases, deoxyribonucleases (DNAse), damage specific deoxyribonucleases, recombinant deoxyribonucleases, topoisomerases, or recombinases. In some embodiments, the nucleic acid degrading component may include, for example, an enzyme capable of exerting a nucleolytic attack, for example, an endonucleolytic or an endophilic attack, or an exonucleolytic or exophilic attack. In some embodiments, the nucleic acid degrading component hydrolyzes bonds including but not limited to, such as, for example, the inter nucleotide linkage in a nucleic acid molecule. In this example, the nucleic acid degrading component may include a phosphoesterase, phosphomonoesterase, or a phosphodiesterase.

In some embodiments, the nucleic acid degrading component or the protein hydrolyzing component may be a recombinant or engineered enzyme. In some embodiments, the source of the nucleic acid degrading component may be one or more biological entities including, but not limited to, human, animal, plant, or bacterial in origin. The type of nuclease used or engineered may be selected at least partially based on the environment. For example, a temperature stable nucleic acid degrading component may be useful in environments subject to higher temperatures or environments subject to lower temperatures. In another example, the nucleic acid degrading component may be engineered, for example, to have a longer half life, optimum activity over a wider range of temperature, a detectable tag, and/or an observable marker as the activity level of the enzyme changes.

In some embodiments, one or more nucleic acid degrading components and/or one or more protein degrading component may include one or more organisms that secrete and/or release one or more nucleases and/or proteases either in nature or due to recombination. In some embodiments, one or more of these organisms, optionally bacteria, may be provided to an environment before and/or after target nucleic acid sequences are present in the environment. Organisms capable of nuclease/protease secretion are known in the art.

In some embodiments, one or more compositions may include one or more components for promoting the enzymatic activity of one or more nucleic acid degrading components and/or one or more protein degrading components and/or for keeping the nucleic acid degrading component and/or the protein degrading component in an active form. The component, for example, may facilitate ambient temperature for enzymatic activity, increase the half life of one or more enzymes, decrease the content of degrading materials present in the environment, activate one or more enzymes, promote the availability of one or more enzymes, and/or enhance the accessibility of one or more enzymes. In some embodiments, the DNA obfuscating system includes an agent, for example, an activator for activating one or more enzymatic activities. Cations, such as, for example, $Mg^{2+}$ or $Ca^{2+}$ may be employed to activate the DNA obfuscating system. Examples of activators include, but are not limited to, chemicals, chemical compounds, cofactors, macromolecules, and/or proteins.

In some embodiments, compositions may include one or more components for maintaining the nucleic acid degrading component and/or the protein degrading component in an inactive form. The one or more components may include, but are not limited to, chemicals, chemical compounds, macromolecules, and/or agents that reduce the degradation of the nucleic acid degrading components and/or the protein degrading components.

In some embodiments, one or more third compositions comprise one or more protein degrading components and one or more third carrier components, the one or more third compositions formulated for wide area dispersion, optionally from one or more of a fogger, a sprinkler, a grenade, or a mister. In some embodiments, one or more of the one or more third compositions are formulated for focused dispensing, optionally from one or more of a sprayer, an aerosol can, a bottle with plunger, and/or extrusion from a tube. In some embodiments, the one or more first compositions and the one or more third compositions are the same composition and/or the one or more third compositions and the one or more second compositions are the same composition.

In some embodiments, one or more third composition may include, one or more of a protein degrading component and/or a recombinant protein degrading component, such as, for example, an exopeptidase, an endopeptidase, aspartic protease, metallo protease, acid protease, basic protease, cysteine protease, serine protease, oligopeptidase, omega peptidase, enzymes, chemical, or chemical compound. The protein degrading component and/or the recombinant protein degrading component may be engineered, for example, for optimum activity in a wide temperature range, to have a longer half life, for removal of intrinsic nuclease activity and/or for enhancement of its intrinsic nuclease activity. Additionally, an agent that activates the protease degrading component may be included in the one or more composition. Examples of such activators include, but are not limited to, cytochromes, cofactors, proteins, peptides, macromolecules, chemicals and/or chemical compounds.

In one aspect, the disclosure is drawn to one or more methods for assembling one or more compositions including one or more obfuscating components, wherein the one or more obfuscating components optionally include one or more nucleic acid depositing components, one or more protein depositing components, one or more nucleic acid degrading components, and/or one or more protein degrading components, and optionally further include one or more carrier components. One or more of these methods may be used to assemble and/or formulate one or more of the compositions described herein. Methods for making formulations are known in the art.

In some embodiments, one or more methods comprise formulating one or more compositions including one or more obfuscating components and one or more carrier components as a gel, a cream, a foam, an aerosol, a liquid, a powder, or a solid. In some embodiments, one or more methods include assembling one or more nucleic acid depositing components, one or more protein depositing components, one or more nucleic acid degrading components, and/or one or more protein degrading components into a composition, and optionally further including one or more carriers. In some embodiments, one or more methods include assembling one or more nucleic acid depositing components, one or more protein depositing components, one or more nucleic acid degrading components, and/or one or more protein degrading components into one or more separate compositions together with one or more carrier components. In some embodiments the one or more carrier compositions are formulated for wide-area dispersion.

In some embodiments, one or more methods comprise assembling a first composition including one or more nucleic acid depositing components and one or more first carrier components; and optionally providing the first composition to a dispensing apparatus, optionally a wide-area dispensing apparatus. In some embodiments, one or more methods comprise formulating a first composition including the one or more nucleic acid depositing components, and optionally one or more first carrier components as a gel, a cream, an aerosol, a liquid, a powder, and/or a solid.

In some embodiments, one or more methods comprise assembling a fourth composition including one or more protein depositing components and one or more fourth carrier components; and optionally providing the fourth composition to a dispensing apparatus, optionally a wide-area dispensing apparatus. In some embodiments, one or more methods comprise formulating a fourth composition including the one or more protein depositing components, and optionally one or more fourth carrier components as a gel, a cream, an aerosol, a liquid, a powder, and/or a solid.

In some embodiments, one or more methods comprise assembling a second composition including one or more nucleic acid degrading components and one or more second carrier components; and providing the second composition to a wide-area dispensing apparatus. In some embodiments, one or more methods comprise formulating a second composition including the one or more nucleic acid degrading components and the one or more second carrier components as a gel, a foam, a cream, an aerosol, a liquid, a powder, and/or a solid. In some embodiments, one or more nucleic acid degrading components are one or more enzymes and/or are at least partially purified, isolated or recombinant.

In some embodiments, one or more methods comprise assembling a third composition including one or more protein degrading components and one or more third carrier components; and providing the third composition to a wide-area dispensing apparatus. In some embodiments, one or more methods comprise formulating a third composition including the one or more protein degrading components and the one or more third carrier components as a gel, a cream, a foam, an aerosol, a liquid, a powder, and/or a solid. In some embodiments, one or more protein degrading components are one or more enzymes and/or are at least partially purified, isolated or recombinant.

In some embodiments, the wide-area dispersing apparatus is selected from the group consisting of a fogger, a mister, a grenade, and a sprinkler. In some embodiments, one or more methods further comprise pressurizing one or more compositions in the wide-area dispensing apparatus.

In one aspect, the disclosure describes one or more methods of obfuscating one or more target biological material identifiers using one or more obfuscating components and/or one or more compositions including one or more obfuscating components. One or more of the compositions described herein may be used in one or more of these methods.

In some embodiments, one or more methods include providing one or more nucleic acid sequences for obfuscating one or more target biological material identifiers to an environment, wherein the one or more nucleic acid sequences are at least partially purified and/or isolated. In some embodiments, one or more methods include providing one or more nucleic acid sequences for obfuscating one or more target biological material identifiers to an environment, wherein one or more of the one or more nucleic acid sequences are recombinant.

In some embodiments, one or methods include identifying one or more nucleic acid sequences for obfuscating one or more target biological material identifiers, and providing one or more of the one or more nucleic acid sequences to an environment. In some embodiments, one or more methods include selecting one or more nucleic acid sequences for obfuscating one or more target biological material identifiers, and providing the one or more nucleic acid sequences to an environment.

In some embodiments, one or more methods include providing one or more protein sequences for obfuscating one or more target biological material identifiers to an environment, wherein the one or more protein sequences are at least partially purified and/or isolated. In some embodiments, one or more methods include providing one or more protein sequences for obfuscating one or more target biological material identifiers to an environment, wherein one or more of the one or more protein sequences are recombinant.

In some embodiments, one or methods include identifying one or more protein sequences for obfuscating one or more target biological material identifiers, and providing one or more of the one or more protein sequences to an environment. In some embodiments, one or more methods include selecting one or more protein sequences for obfuscating one or more target biological material identifiers, and providing the one or more protein sequences to an environment.

In some embodiments, one or more methods include identifying one or more obfuscating components for obfuscating one or more target biological material identifiers at least partially based on information associated with the one or more target biological material identifiers. In some embodiments, the one or more target biological material identifiers identify one or more individuals and/or one or more populations.

In some embodiments, information associated with the one or more target biological material identifiers includes the identity of one or more target populations that are optionally one or more individuals. In some embodiments, the one or more target populations optionally include, but are not limited to, one or more ethnic groups, one or more demographic groups, one or more racial groups, one or more genders and/or share one or more genetic characteristics. In some embodiments, one or more genetic characteristics are optionally selected from the group consisting of gender, genetic disease, genetic abnormality, chromosomal aberration, determinants of physical characteristics, age, telomere length, and mitochondrial genome.

In some embodiments, one or more methods include identifying one or more obfuscating components for obfuscating one or more target biological material identifiers at least partially based on a percent sequence identity or a percent sequence similarity with one or more nucleic acid sequences and/or one or more protein sequences associated with the one or more target biological material identifiers. In some embodiments, the one or more obfuscating components are optionally one or more nucleic acid sequences and/or one or more protein sequences.

In some embodiments, one or more nucleic acid sequences or one or more protein sequences share approximately 10 percent to 99 percent sequence similarity or sequence identity with one or more target nucleic acid sequences or one or more target protein sequences, respectively. In some embodiments, the one or more nucleic acid sequences or one or more protein sequences share approximately 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, and/or 100% sequence identity and/or sequence similarity with one or more target nucleic acid sequences or one or more target protein sequences, respectively.

In some embodiments, one or more methods further comprise identifying and/or selecting one or more nucleic acid sequences or one or more protein sequences with approximately 10 percent to 99 percent similarity and/or identity to the one or more target nucleic acid sequences or one or more target protein sequences, respectively. In some embodiments, the one or more nucleic acid sequences or one or more protein sequences share approximately 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, and/or 100% sequence identity and/or sequence similarity with one or more target nucleic acid sequences or one or more target protein sequences, respectively.

In some embodiments, one or more methods further comprise determining the sequence of one or more target nucleic acid sequences and/or one or more target protein sequences. In some embodiments, one or more methods further comprise determining the sequence of one or more target nucleic acid sequences and/or one or more target protein sequences, and identifying and/or selecting one or more obfuscating components at least partially based on the sequence of the one or more target nucleic acid sequences and/or the one or more target protein sequences.

In some embodiments, the one or more obfuscating components are selected from the group consisting of one or more nucleic acid sequence depositing components, one or more protein sequence depositing components, one or more nucleic acid degrading components, and one or more protein degrading components.

In some embodiments, one or more methods include providing one or more obfuscating components to an environment in a sequence. In illustrative embodiments, one or more methods include providing and/or releasing the one or more obfuscating components in a sequence, such as, but not limited to, providing the one or more nucleic acid sequence depositing components, followed by the one or more protein sequence depositing components, followed by the one or more protein degrading components, followed by the one or more nucleic acid degrading components, and/or providing the one or more protein degrading components, followed by the one or more nucleic acid degrading components, followed by the one or more protein sequence depositing components, followed by the one or more nucleic acid sequence depositing components.

In some embodiments, one or more methods include providing the one or more obfuscating components to an environment separately. In illustrative embodiments, one or more methods include providing and/or releasing the one or more nucleic acid sequence depositing components, the one or more protein sequence depositing components, the one or more nucleic acid degrading components, and/or the one or more protein degrading components separately. In some embodiments, the one or more components are released separately as to location and/or separately as to time. In illustrative embodiments, one or more methods include providing and/or releasing the one or more nucleic acid sequence depositing components, the one or more protein sequence depositing components, the one or more nucleic acid degrading components, and/or the one or more protein degrading components at one or more time intervals. The time interval between the release of each component may be the same or different. The time interval between the release of each component may depend, for example, on the time required for a previously released component to function, for example to degrade DNA and/or protein and/or to activate or inactivate a component. Time intervals for activity of one or more components may be described herein and/or are known in the art.

In some embodiments, one or more methods include providing the one or more obfuscating components to an environment at one or more identifiable time intervals. In some embodiments, the one or more identifiable time intervals include, but are not limited to, fixed time intervals, periodic time intervals, programmable and/or programmed time intervals, triggered time intervals due to environmental changes such as light, motion, noise, or temperature, manually determined time intervals, automatic time intervals, remotely-controlled time intervals, time intervals based on readouts from one or more sensors and/or detectors, as well as other appropriate time intervals.

In some embodiments, one or more identifiable time intervals include, but are not limited to, time intervals of seconds to minutes to hours to days to weeks to months. In some embodiments, the one or more identifiable time intervals include 1 second, 5 seconds, 15 seconds, 30 seconds, 45 seconds or 60 seconds; 1 minute, 5 minutes, 15 minutes, 30 minutes, 60 minutes; 1 hour, 2 hours, 5 hours, 8 hours, 12 hours, 18 hours, 24 hours; 1 day, 2 days, 3 days, 7 days; 1 week, 2 weeks, 4 weeks; and/or 1 month, 2 months, 3 months, 4 months, 6 months, 8 months, 12 months.

In some embodiments, one or more methods include providing one or more obfuscating components to an environment using a wide area dispensing apparatus. In some embodiments, one or more wide area dispensing apparatus may include, but are not limited to, foggers, misters, sprinklers, bombs, and/or grenades. In some embodiments, one or more methods include wide-area dispersion of the one or more compositions to the one or more locations using one or more of one or more foggers, one or more sprinklers, or one or more misters. In some embodiments, one or more methods include manually-controlled, optionally wide-area, dispersion of one or more compositions to the one or more locations. In some embodiments, one or more methods include automatically-controlled, optionally wide-area, dispersion of one or more compositions to the one or more locations optionally at least partially based on readings from one or more sensors and/or detectors. In some embodiments, one or more methods include remote-controlled, optionally wide-area, dispersion of one or more compositions to the one or more locations, wherein the remote-controlled dispersion is optionally wireless remote-controlled, optionally wide-area, dispersion, and is optionally at least partially based on readings from one or more sensors and/or detectors.

In some embodiments, one or more methods further comprise co-localizing one or more nucleic acid sequences with one or more first carriers that are optionally one or more natural carriers and/or one or more non-natural carriers. In some embodiments, one or more methods further comprise co-localizing one or more protein sequences with one or more fourth carriers that are optionally one or more natural carriers and/or one or more non-natural carriers. In some embodiments, one or more natural carriers include one or more isolated, separated, and/or purified cells, skin, hair, fur, and/or biological secretions that optionally include, but are not limited to, saliva, semen, urine, blood, and feces, and optionally further include any biological materials of an organism containing one or more nucleic acids and/or one or more proteins. In some embodiments, one or more non-natural carriers include buffers, powders, lotions, aerosol droplets, liposomes, gels, shampoos, beads, solutions, and other appropriate wet or dry carriers.

In some embodiments, one or more methods further comprise providing a composition including one or more nucleic acid degrading components and one or more second carriers. In some embodiments, one or more methods further comprise providing a composition including one or more protein degrading components and one or more third carriers.

In some embodiments, one or more methods comprise wide-area dispersion of one or more compositions including one or more nucleic acid degrading components and one or more second carrier components to one or more locations. In some embodiments, one or more methods comprise providing automatically one or more compositions including one or more nucleic acid degrading components and one or more second carrier components to one or more environments. In some embodiments, one or more methods comprise providing remotely one or more compositions including one or more nucleic acid degrading components and one or more second carrier components to one or more environments.

In some embodiments, at least one of the one or more nucleic acid degrading components is one or more non-enzymatic nucleic acid degrading components and/or one or more enzymatic nucleic acid degrading components, and optionally includes one or more enzymatic and/or non-enzymatic activating components and/or one or more enzymatic and/or non-enzymatic inactivating components.

In some embodiments, one or more methods further comprise activating and/or inactivating one or more of the one or more nucleic acid degrading components.

In some embodiments, one or more methods further comprise wide-area dispersion of one or more compositions including one or more protein degrading components and one or more third carrier components to one or more locations. In some embodiments, at least one of the one or more protein degrading components is one or more non-enzymatic protein degrading components and/or one or more enzymatic protein degrading components. In some embodiments, the one or more third carrier components are the same as the one or more second carrier components. In some embodiments, wide-area dispersion of the one or more nucleic acid degrading components occurs separately from wide-area dispersion of the one or more protein degrading components. In some embodiments, wide-area dispersion of the one or more nucleic acid degrading components and wide-area dispersion of the one or more protein degrading components occurs sequentially. In some embodiments, wide-area dispersion of the one or more protein degrading components occurs before wide-area dispersion of the one or more nucleic acid degrading components.

In some embodiments, the methods further comprise activating and/or inactivating one or more of the one or more enzymatic and/or non-enzymatic protein degrading components.

In some embodiments, one or more methods includes providing one or more of the obfuscating components to an environment prior to possible deposition of one or more target biological material identifiers. In illustrative examples, one or more obfuscating components may be dispersed in an environment as a preventive measure in anticipation of the deposition of one or more target nucleic acids. For example, the dispersed one or more obfuscating components may be activated by the subsequent deposition of one or more target nucleic acids resulting in degradation of the one or more target nucleic acids and/or may be subsequently activated by dispersal of one or more activating agent following deposition of the one or more target nucleic acid sequences. For example, the dispersed one or more obfuscating components may include one or more nucleic acid sequences that share 50-100% sequence identity and/or sequences similarity with one or more target nucleic acid sequences.

In one aspect, the disclosure is drawn to one or more apparatus for identity obfuscation and/or biological material identifiers obfuscation. In some embodiments, any one of the methods described herein may be performed on one or more apparatus, and/or any one of the compositions described herein may be used in one or more apparatus.

Figure 5:
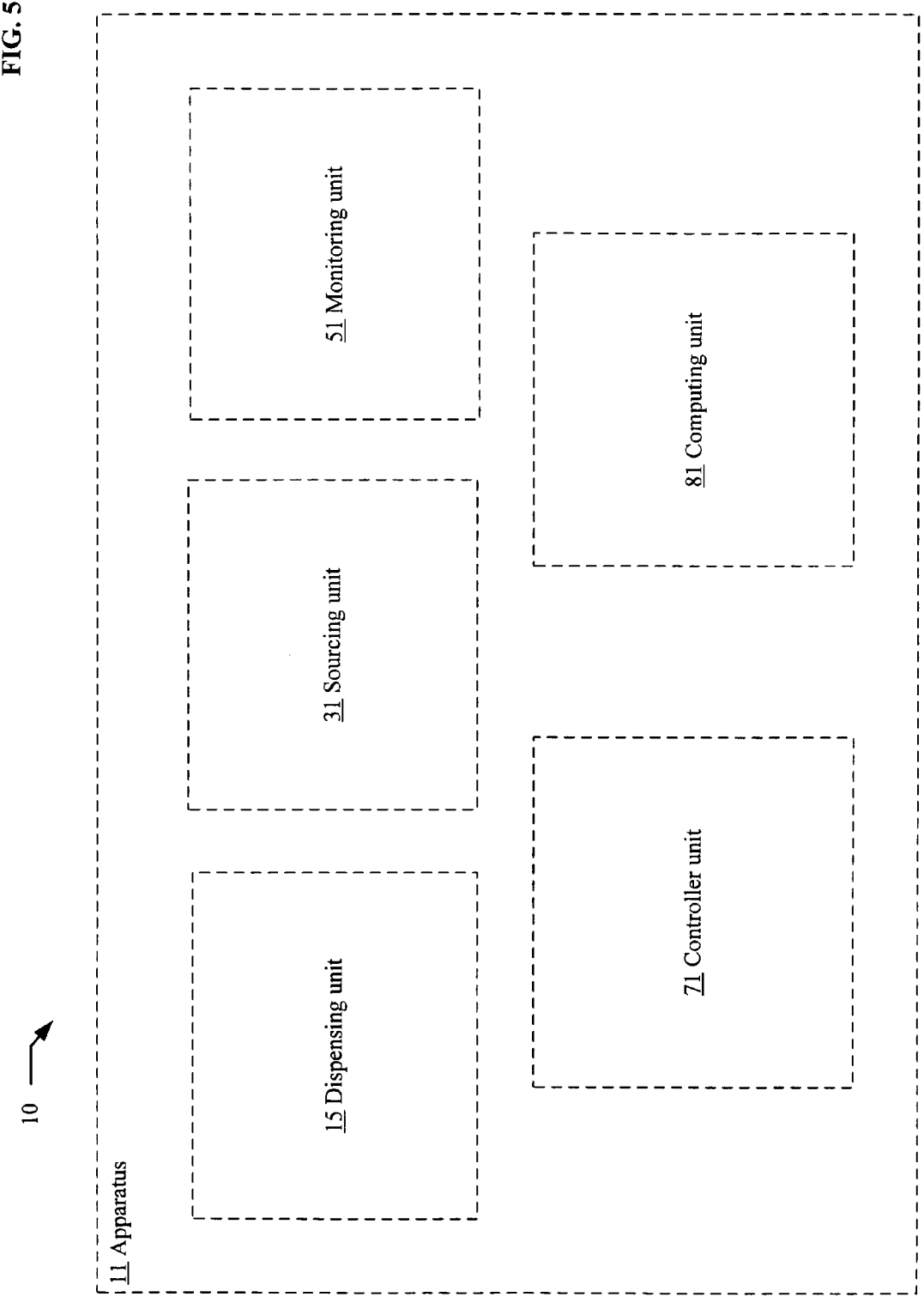
FIG. 5 shows a schematic of an illustrative apparatus in which embodiments may be implemented.
Figure 6:
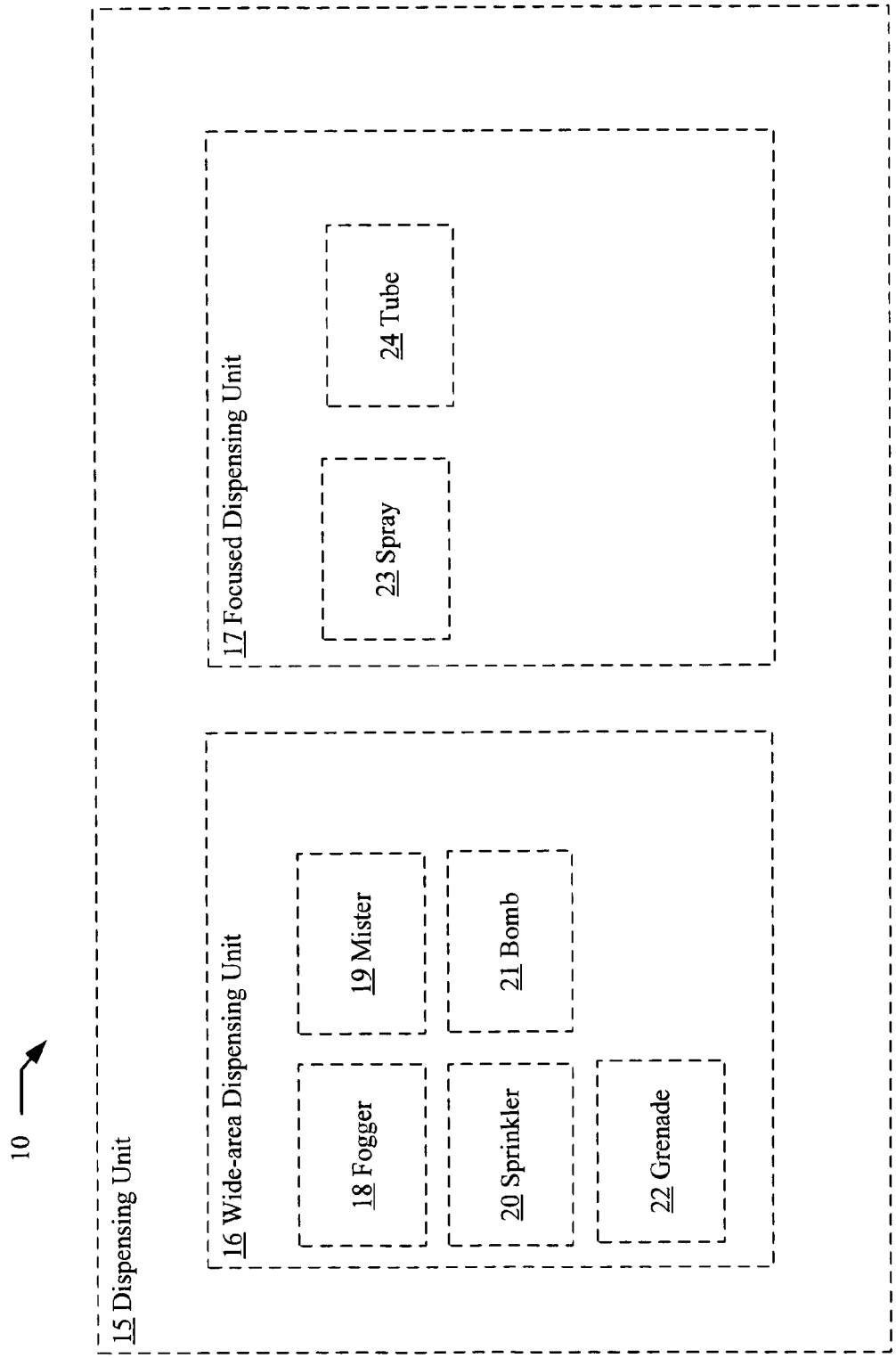
FIG. 6 shows schematics of illustrative embodiments of the apparatus of FIG. 5, with illustrative examples of a dispensing unit.

FIG. 5 shows a schematic 10 of an illustrative apparatus 11 for identity obfuscation and/or biological material identifiers obfuscation in which embodiments may be implemented. The apparatus 11 is optionally operable for obfuscating one or more biological material identifiers. The apparatus may optionally be, or include, one or more units including, but not limited to, one or more dispensing units 15, one or more sourcing units 31, one or more monitoring units 51, one or more controller units 71, and/or one or more computing units 81. In some embodiments, one or more of the units may be internal or external to the apparatus and still be considered part of the apparatus.

In some embodiments, one or more apparatus 11 further includes one or more fluid flows. In some embodiments, the one or more fluid flows connect and/or allow the transfer of one or more obfuscating components among one or more of the optional one or more units of the apparatus 11. In some embodiments, the one or more fluid flows are operable to provide, co-localize, release, dispense, and/or discharge, optionally sequentially and/or separately, one or more obfuscating components. In some embodiments, the one or more fluid flows are operable to provide, co-localize, release, dispense, and/or discharge, optionally sequentially and/or separately, one or more obfuscating components at one or more identifiable time intervals.

In some embodiments, one or more apparatus 11 further includes one or more pressurized units or parts of units. In some embodiments, the one or more pressurized units or parts of units connect and/or allow the transfer of one or more obfuscating components and or one or more carrier components and/or one or more compositions among one/or more of the optional one or more units of the apparatus 11. In some embodiments, the one or more pressurized units or parts of units are operable to provide, co-localize, release, dispense, and/or discharge, optionally sequentially and/or separately, one or more obfuscating components and/or one or more carrier components and/or one or more compositions. In some embodiments, the one or more pressurized units or parts of units are operable to provide, co-localize, release, dispense, and/or discharge, optionally sequentially and/or separately, one or more obfuscating components and/or one or more carrier components and/or one or more compositions at one or more identifiable time intervals.

In some embodiments, one or more apparatus includes one or more devices and/or dispensing units for providing one or more obfuscating components to an environment; and one or more obfuscating components. In some embodiments, one or more apparatus includes one or more devices and/or dispensing units for providing one or more nucleic acid sequences to an environment; and one or more nucleic acid sequences. In some embodiments, one or more apparatus includes one or more devices and/or dispensing units for providing one or more obfuscating components to an environment; and one or more obfuscating components, wherein at least one of the one or more obfuscating components is one or more nucleic acid sequences.

In some embodiments, one or more apparatus includes one or more devices and/or dispensing units for providing one or more protein sequences to an environment; and one or more protein sequences. In some embodiments, one or more apparatus includes one or more devices and/or dispensing units for providing one or more obfuscating components to an environment; and one or more obfuscating components, wherein at least one of the one or more obfuscating components is one or more protein sequences.

In some embodiments, one or more apparatus comprises a wide area dispersing device operable to provide one or more nucleic acid degrading components to an environment; one or more nucleic acid degrading components; and one or more carrier components. In some embodiments, one or more apparatus comprises a device operable to automatically provide one or more nucleic acid degrading components to an environment; and a composition including one or more nucleic acid degrading components and one or more second carrier components. In some embodiments, one or more apparatus comprises a device operable to remotely provide one or more nucleic acid degrading components to an environment; and a composition including one or more nucleic acid degrading components and one or more second carrier components.

In some embodiments, one or more apparatus comprises a wide area dispersing device operable to provide one or more protein degrading components to an environment; one or more protein degrading components; and one or more carrier components. In some embodiments, one or more apparatus comprises a device operable to automatically provide one or more protein degrading components to an environment; and a composition including one or more protein degrading components and one or more third carrier components. In some embodiments, one or more apparatus comprises a device operable to remotely provide one or more protein degrading components to an environment; and a composition including one or more protein degrading components and one or more third carrier components.

In some embodiments, one or more apparatus and/or one or more attachment to an apparatus is moveable, optionally manually, remotely, wirelessly, programmably, and/or automatically.

FIG. 6 shows a schematic 10 of illustrative embodiments of the optional apparatus 11 of FIG. 5, with specific illustrative embodiments of one or more dispensing units 15, including one or more optional wide-area dispensing units 16 and/or one or more optional focused dispensing units 17. In some embodiments, one or more optional wide-area dispensing units 16 include, but are not limited to one or more foggers 18, one or more misters 19, one or more sprinklers 20, one or more bombs 21, and/or one or more grenades 22. In some embodiments, one or more optional focused dispensing units 17 include, but are not limited to, one or more sprayers 23 and/or one or more squeeze tubes 24.

In some embodiments, one or more dispensing units 15 further include one or more fluid flows. In some embodiments, the one or more fluid flows connect and/or allow the transfer of one or more obfuscating components and/or one or more carrier components and/or one or more compositions among one or more of the optional one or more units of the apparatus 11, including but not limited to the one or more dispensing units 15 and the one or more sourcing units 31. In some embodiments, the one or more fluid flows are operable to provide, co-localize, release, dispense, and/or discharge, optionally sequentially and/or separately, one or more obfuscating components and/or one or more carrier components and/or one or more compositions. In some embodiments, the one or more fluid flows are operable to provide, co-localize, release, dispense, and/or discharge, optionally sequentially and/or separately, one or more obfuscating components and/or one or more carrier components and/or one or more compositions at one or more identifiable time intervals.

In some embodiments, one or more dispensing units 15 further include one or more pressurized units or parts of units. In some embodiments, the one or more pressurized units or parts of units connect and/or allow the transfer of one or more obfuscating components and/or one or more carrier components and/or one or more compositions among one or more of the optional one or more units of the apparatus 11, including but not limited to the one or more dispensing units 15 and the one or more sourcing units 31. In some embodiments, the one or more pressurized units or parts of units are operable to provide, co-localize, release, dispense, and/or discharge, optionally sequentially and/or separately, one or more obfuscating components and/or one or more carrier components and/or one or more compositions. In some embodiments, the one or more pressurized units or parts of units are operable to provide, co-localize, release, dispense, and/or discharge, optionally sequentially and/or separately, one or more obfuscating components and/or one or more carrier components and/or one or more compositions at one or more identifiable time intervals.

In some embodiments, one or more apparatus includes one or more devices and/or dispensing units for providing one or more obfuscating components to an environment; and one or more obfuscating components, wherein the one or more obfuscating components are selected from the group consisting of one or more nucleic acid depositing components, one or more protein depositing components, one or more nucleic acid degrading components, and one or more protein degrading components.

In some embodiments, one or more dispensing units may be in the form of a spray can or a squeeze tube, optionally for use in deploying small scale amounts of one or more compositions, for example when applying to the skin and/or hair. In some embodiments, the one or more dispensing units may include cylinders or larger containers for use in deploying larger scale amounts of one or more compositions. In some embodiments, one or more dispensing units may include attachments for reaching crevices or targeting an area of interest. In some embodiments, the one or more dispensing units may be strategically placed and remotely deployed as needed. In some embodiments, the one or more dispensing units may be moveable, optionally using remote control and/or optionally wireless, programmable or automatic.

In some embodiments, one or more apparatus includes one or more dispensing units, wherein at least one of the one or more obfuscating components is separate from one or more of the one or more obfuscating components. In some embodiments, one or more nucleic acid depositing components are separate from one or more nucleic acid degrading components. In some embodiments, one or more nucleic acid depositing components are separate from one or more protein depositing components. In some embodiments, one or more nucleic acid degrading components are separate from the one or more protein degrading components. In some embodiments, one or more protein depositing components are separate from the one or more protein degrading components. In some embodiments, a physical divider may sequester the nucleic acid depositing components, the protein depositing components, the nucleic acid degrading components and/or the protein degrading components. In some embodiments, a physical divider may sequester the nucleic acid depositing components, the protein depositing components, the nucleic acid degrading components and/or the protein degrading components from one or more components that activate the nucleic acid degrading component and/or the protein degrading component.

In some embodiments, one or more apparatus includes one or more dispensing units, wherein at least one of the one or more obfuscating components are released separately from one or more of the obfuscating components. In some embodiments, one or more nucleic acid depositing components are released separately from the one or more nucleic acid degrading components. In some embodiments, one or more nucleic acid degrading components are released separately from the one or more protein degrading components. In some embodiments, one or more nucleic acid depositing components are released separately from the one or more protein depositing components. In some embodiments, one or more protein depositing components are released separately from the one or more protein degrading components.

In some embodiments, one or more apparatus includes one or more dispensing units, wherein the one or more obfuscating components are released sequentially. In some embodiments, the one or more nucleic acid depositing components and the one or more nucleic acid degrading components are released sequentially from the dispersing device. In some embodiments, the one or more protein degrading components and the one or more nucleic acid degrading components are released sequentially from the dispersing device. In some embodiments, the one or more nucleic acid depositing components and the one or more protein depositing components are released sequentially from the dispersing device. In some embodiments, the one or more protein degrading components and the one or more protein depositing components are released sequentially from the dispersing device.

In some embodiments, one or more apparatus includes one or more dispersing device selected from the group consisting of a fogger, a sprinkler, a grenade, and a mister, optionally manually operable to provide the one or more compositions to the environment. In some embodiments, one or more, optionally wide-area, dispersing device is operable to automatically provide the one or more compositions to the environment. In some embodiments, one or more apparatus includes one or more, optionally wide-area, dispersing device operable to remotely provide the one or more compositions to the environment. In some embodiments, one or more apparatus includes one or more, optionally wide-area, dispersing device operable by wireless remote control to provide the one or more compositions to the environment. In some embodiments, one or more apparatus includes one or more, optionally wide-area, dispersing device remotely actuated to provide the one or more compositions to the environment. In some embodiments, one or more, optionally wide-area, dispersing device is operable to remotely provide the one or more compositions to the environment at least partially based on readings from one or more monitoring units, optionally one or more of one or more sensors or one or more detectors.

In some embodiments, one or more apparatus includes one or more, optionally wide-area, dispersing device including one or more attachments for providing the one or more compositions to the environment. In some embodiments, one or more apparatus includes wireless or robotic attachments optionally for positioning in crevices, nooks, or hard to reach areas. In some embodiments, the wireless or robotic attachments may be controlled from the exterior remotely. In some embodiments, control may be through human interaction or may be performed under control of software, hardware, or firmware.

In some embodiments, one or more apparatus comprises one or more, optionally wide-area, dispersing device operable to provide one or more compositions to an environment; and a first composition including one or more nucleic acid depositing components and one or more first carrier components. In some embodiments, one or more apparatus comprises a device configured to optionally widely disperse one or more compositions in an environment; and a first composition including one or more nucleic acid depositing components and one or more first carrier components.

In some embodiments, one or more apparatus comprises one or more, optionally wide-area, dispersing device operable to provide one or more compositions to an environment; and a fourth composition including one or more protein depositing components and one or more fourth carrier components. In some embodiments, one or more apparatus comprises a device configured to optionally widely disperse one or more compositions in an environment; and a fourth composition including one or more protein depositing components and one or more fourth carrier components.

In some embodiments, one or more apparatus comprises a wide-area dispersing device operable to provide one or more compositions to an environment; and a second composition including one or more nucleic acid degrading components and one or more second carrier components. In some embodiments, one or more apparatus comprises a device configured to widely disperse one or more compositions in an environment; and a second composition including one or more nucleic acid degrading components and one or more second carrier components.

In some embodiments, one or more apparatus comprises a wide-area dispersing device operable to provide one or more compositions to an environment; and a third composition including one or more protein degrading components and one or more third carrier components. In some embodiments, one or more apparatus comprises a device configured to widely disperse one or more compositions in an environment; and a third composition including one or more protein degrading components and one or more third carrier components.

In some embodiments, one or more apparatus comprises a device with an output port for automatically providing one or more compositions to an environment; and a first composition including one or more nucleic acid depositing components and one or more first carrier components. In some embodiments, one or more apparatus comprises a device with an output port operable to remotely provide one or more compositions to an environment; and a first composition including one or more nucleic acid depositing components and one or more first carrier components.

In some embodiments, one or more apparatus comprises a device with an output port for automatically providing one or more compositions to an environment; and a fourth composition including one or more protein depositing components and one or more fourth carrier components. In some embodiments, one or more apparatus comprises a device with an output port operable to remotely provide one or more compositions to an environment; and a fourth composition including one or more protein depositing components and one or more fourth carrier components.

In some embodiments, one or more apparatus comprises a device with an output port for automatically providing one or more compositions to an environment; and a second composition including one or more nucleic acid degrading components and one or more second carrier components. In some embodiments, one or more apparatus comprises a device with an output port operable to remotely provide one or more compositions to an environment; and a second composition including one or more nucleic acid degrading components and one or more second carrier components.

In some embodiments, one or more apparatus comprises a device with an output port for automatically providing one or more compositions to an environment; and a third composition including one or more protein degrading components and one or more third carrier components. In some embodiments, one or more apparatus comprises a device with an output port operable to remotely provide one or more compositions to an environment; and a third composition including one or more protein degrading components and one or more third carrier components.

Figure 7:
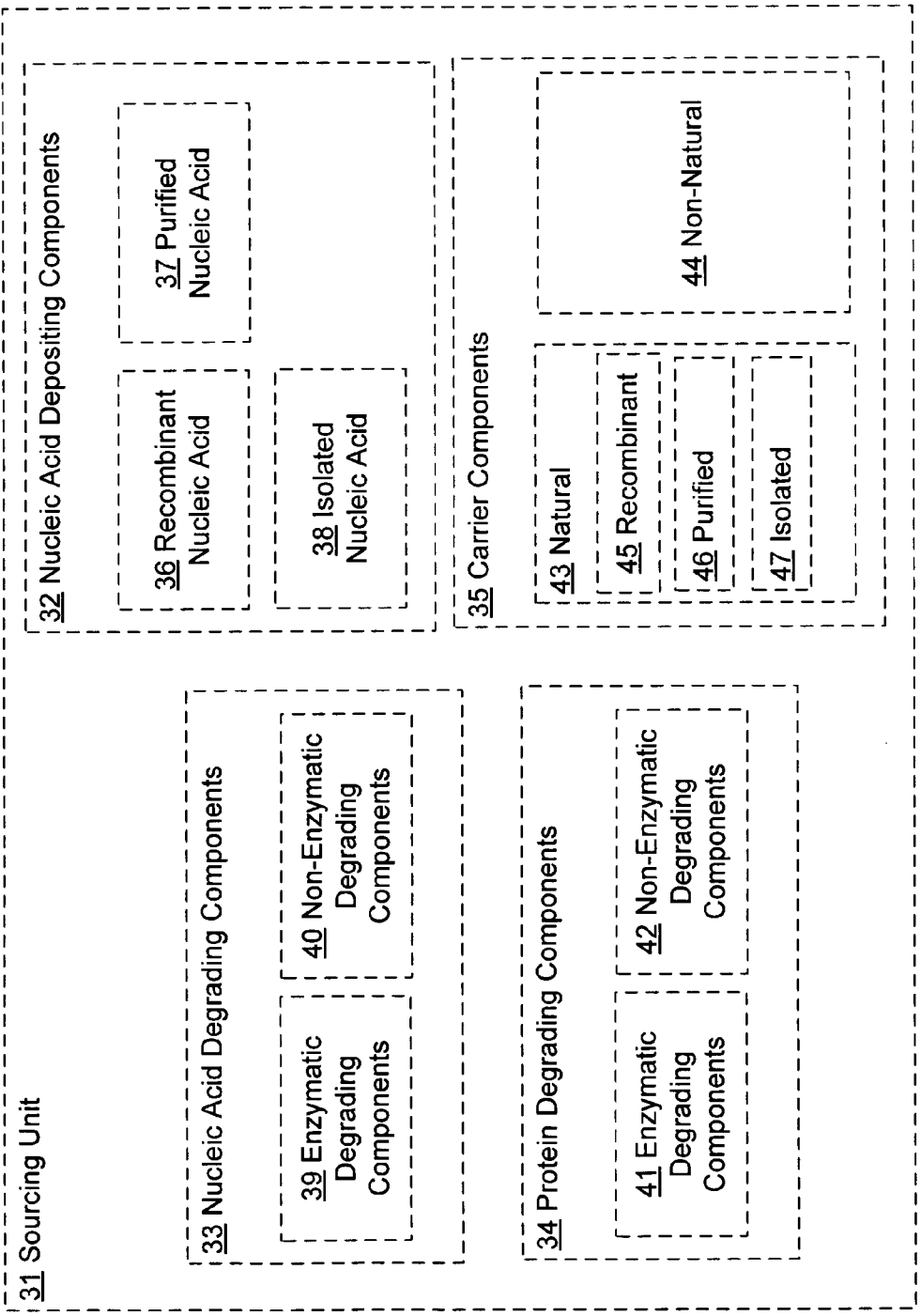
FIG. 7 shows schematics of illustrative embodiments of the apparatus of FIG. 5, with specific examples of a sourcing unit.

FIG. 7 shows a schematic 10 of illustrative embodiments of the apparatus 11 of FIG. 5, with specific illustrative embodiments of one or more sourcing units 31, including but not limited to sourcing units containing one or more obfuscating components and/or one or more compositions including one or more obfuscating components and one or more carriers. In some embodiments, one or more apparatus includes, but is not limited to, one or more dispensing units 15 and one or more sourcing units 31. In some embodiments, one or more of the one or more dispensing units 15 and one or more of the one or more sourcing units 31 are the same unit. In some embodiments, one or more sourcing units 31 are remotely located from one or more dispensing units 15.

In some embodiments, one or more sourcing units 31 include one or more fluid flows or are at least partially pressurized. In some embodiments, one or more sourcing units 31 are operable to provide, co-localize, release, and/or dispense, optionally separately and/or sequentially, one or more obfuscating components and/or one or more carrier components and/or one or more compositions to one or more identifiable locations at optionally one or more identifiable time intervals. In some embodiments, each one or more composition and/or obfuscating component, and/or carrier component may be localized in one or more separate sourcing units and/or in the same one or more sourcing units.

Sourcing units include, but are not limited to, optional sourcing units containing one or more sources of nucleic acid depositing components 32, optional sourcing units containing one or more sources of nucleic acid degrading components 33, optional sourcing units containing one or more sources of protein degrading components 34 and/or optional sourcing units containing one or more sources of one or more carrier components 35, as well as optional sourcing units containing one or more sources of one or more protein depositing components, and optional sourcing units containing one or more sources of one or more compositions.

Sourcing units for one or more nucleic acid depositing components may optionally include, but are not limited to, one or more optional sourcing units containing one or more sources of recombinant nucleic acids 36, one or more optional sourcing units containing one or more sources of one or more at least partially purified nucleic acids 37, and/or one or more optional sourcing units containing one or more sources of one or more at least partially isolated nucleic acids 38.

Sourcing units for one or more protein depositing components may optionally include, but are not limited to, one or more optional sourcing units containing one or more sources of recombinant proteins, one or more optional sourcing units containing one or more sources of one or more at least partially purified proteins, and/or one or more optional sourcing units containing one or more sources of one or more at least partially isolated proteins.

Sourcing units for one or more nucleic acid degrading components 33 may optionally include, but are not limited to, one or more optional sourcing units containing one or more sources of one or more enzymatic nucleic acid degrading components 39 and/or one or more optional sourcing units containing one or more sources of one or more non-enzymatic nucleic acid degrading components 40. In some embodiments, one or more apparatus further comprises one or more sourcing unit for each one or more nucleic acid degrading component, one or more second carrier component, and/or one or more activating and/or inactivating component.

Sourcing units for one or more protein degrading components 34 may optionally include, but are not limited to, one or more optional sourcing units containing one or more sources of one or more enzymatic protein degrading components 41 and/or one or more optional sourcing units containing one or more sources of one or more non-enzymatic protein degrading components 42. In some embodiments, one or more apparatus further comprises one or more sourcing unit for each one or more protein degrading component, one or more third carrier component, and/or one or more activating and/or inactivating component.

Sourcing units for one or more carrier components 35 may optionally include, but are not limited to, one or more optional sourcing units containing one or more sources of one or more natural carrier components 43 and/or one or more optional sourcing units containing one or more sources of one or more non-natural carrier components 44. One or more optional sourcing units for one or more natural carrier components 43 may optionally include, but are not limited to, one or more optional sourcing units containing one or more sources of one or more recombinant carrier components 45, one or more optional sourcing units containing one or more sources of one or more at least partially purified carrier components 46, and/or one or more optional sourcing units containing one or more sources of one or more at least partially isolated carrier components 47.

Sourcing units for one or more compositions may optionally include, but are not limited to, one or more optional sourcing units containing one or more sources of one or more first compositions, one or more optional sourcing units containing one or more sources of one or more second compositions, one or more optional sourcing units containing one or more sources of one or more third compositions, and/or one or more optional sourcing units containing one or more sources of one or more fourth compositions.

In some embodiments, one or more apparatus further comprises one or more sourcing units, each sourcing unit including one or more natural carrier components, wherein the one or more natural carrier components include, but are not limited to, skin, hair, biological fluids, and/or biological excretions. In some embodiments, one or more apparatus further comprises one or more sourcing units, each sourcing unit including one or more non-natural carrier components, wherein the one or more non-natural carrier components include, but are not limited to, buffers, PEG, emollients, surfactants, and/or dyes.

In some embodiments, one or more sourcing units are located at one or more dispensing locations. In some embodiments, one or more sourcing units are located at one or more locations remote from one or more of the one or more dispensing locations. In some embodiments, one or more apparatus includes one or more compositions maintained and/or located and/or sourced in one or more central locations.

In some embodiments, one or more apparatus optionally includes one or more sourcing units optionally including one or more first compositions including one or more nucleic acid depositing components and optionally including one or more first carrier components. In some embodiments, the one or more nucleic acid depositing components include one or more nucleic acid sequences, wherein the one or more nucleic acid sequences are optionally at least partially purified, isolated and/or recombinant. In some embodiments, the one or more first carriers are one or more natural carriers, optionally selected from the group consisting of skin, hair, and saliva. In some embodiments, the one or more nucleic acid sequences share 20% to 99% sequence identity and/or sequence similarity with one or more target nucleic acid sequences. In some embodiments, the one or more nucleic acid sequences share the same race, ethnicity, and or demographic as the target nucleic acid sequences. In some embodiments, the one or more nucleic acid sequences share the same genetic characteristics and/or chromosomal aberrations as the target nucleic acid sequences.

In some embodiments, one or more apparatus optionally includes one or more sourcing units optionally including one or more fourth compositions including one or more protein depositing components and optionally including one or more fourth carrier components. In some embodiments, the one or more protein depositing components include one or more protein sequences, wherein the one or more protein sequences are optionally at least partially purified, isolated and/or recombinant. In some embodiments, the one or more fourth carriers are one or more natural carriers, optionally selected from the group consisting of skin, hair, and saliva. In some embodiments, the one or more protein sequences share 20% to 99% sequence identity and/or sequence similarity with one or more target protein sequences. In some embodiments, the one or more protein sequences share the same race, ethnicity, and or demographic as the target protein sequences. In some embodiments, the one or more protein sequences share the same genetic characteristics and/or chromosomal aberrations as the target protein sequences.

In some embodiments, one or more apparatus optionally includes one or more sourcing units optionally including one or more nucleic acid degrading components, wherein at least one of the one or more nucleic acid degrading components is one or more enzymatic nucleic acid degrading components and/or at least one of the one or more nucleic acid degrading components is one or more non-enzymatic nucleic acid degrading components. In some embodiments, at least one of the one or more nucleic acid degrading components is one or more nucleases, and/or selected from the group consisting of one or more enzymes capable of exerting an endonucleolytic attack on one or more nucleic acids and one or more enzymes capable of exerting an exonucleolytic attack on one or more nucleic acids. In some embodiments, at least one of the one or more nucleic acid degrading components is selected from the group consisting of one or more substrate specific nucleic acid degrading components, one or more sugar non specific nucleases, one or more restriction endonucleases, one or more deoxyribonucleases, one or more ribonucleases, one or more damage specific deoxyribonucleases, one or more recombinant deoxyribonuclease, one or more topoisomerases, and one or more recombinases. In some embodiments, at least one of the one or more nucleic acid degrading components is one or more temperature stable enzymatic nucleic acid degrading components.

In some embodiments, one or more apparatus optionally includes one or more sourcing units optionally including one or more third compositions, optionally including one or more protein degrading components and one or more third carrier components. In some embodiments, the one or more third composition is included in the one or more second composition and/or the one or more first composition. In some embodiments, one or more apparatus includes one or more one or more protein degrading components, wherein at least one of the one or more protein degrading components is one or more enzymatic protein degrading components and/or one or more non-enzymatic protein degrading components.

In some embodiments, one or more apparatus optionally includes one or more sourcing units optionally including one or more carrier components, optionally including, but not limited to, one or more first carrier components, one or more fourth carrier components, one or more second carrier components, and/or one or more third carrier components. In some embodiments, one or more of the one or more first carrier components, one or more fourth carrier components, one or more second carrier components, and/or one or more third carrier components are the same.

In some embodiments, one or more of the one or more carrier components is selected from the group consisting of one or more surfactant, one or more detergent and one or more emulsifier. In some embodiments, one or more of the carrier components reduces surface tension of one or more of the one or more compositions. In some embodiments, one or more of the one or more carrier components is pharmaceutical grade, cosmetic grade, or house-hold grade. In some embodiments, one or more of the one or more compositions is in a form selected from the group consisting of a gel, a cream, an aerosol, a liquid, a powder, and a solid.

In some embodiments, one or more apparatus optionally includes one or more sourcing units optionally including one or more carrier components, wherein one or more of the one or more carrier components is separate from one or more of the one or more obfuscating components, optionally including one or more nucleic acid depositing components, one or more protein depositing components, one or more nucleic acid degrading components and/or one or more protein degrading components. In some embodiments, one or more of the one or more carrier components is co-localized with one or more of the one or more obfuscating components before providing the one or more obfuscating components to the environment. In some embodiments, one or more first carrier components is co-localized with one or more nucleic acid sequences, one or more fourth carrier components is co-localized with one or more protein sequences, one or more second carrier components is co-localized with one or more nucleic acid degrading components, and/or one or more third carrier components is co-localized with one or more protein degrading components prior to, or at the time of, release of the one or more components to the environments.

In some embodiments, one or more apparatus optionally includes one or more sourcing units optionally including one or more second and/or third carrier components, wherein one or more of the one or more second and/or third carrier components performs one or more functions selected from the group consisting of: maintains one or more of the one or more nucleic acid and/or protein degrading components in an active form; maintains one or more of the one or more nucleic acid and/or protein degrading components in an inactive form; activates the one or more nucleic acid and/or protein degrading components; reduces inactivation of the one or more nucleic acid and/or protein degrading components; reduces degradation of the one or more nucleic acid and/or protein degrading components; increases availability of the one or more nucleic acid and/or protein degrading components; and increases effectiveness of the one or more nucleic acid and/or protein degrading components. In some embodiments, one or more second and/or third carrier components activate the one or more nucleic acid and/or protein degrading components.

In some embodiments, one or more apparatus optionally includes one or more sourcing units optionally including one or more protein degrading components wherein at least one of the one or more protein degrading components is one or more enzymatic protein degrading components and/or one or more non-enzymatic protein degrading components. In some embodiments, at least one of the one or more protein degrading components is one or more exopeptidase and/or is selected from the group consisting of one or more endopeptidase, one or more aspartic protease, one or more metallo protease, one or more acid protease, one or more basic protease, one or more cysteine protease, one or more serine protease, one or more oligopeptidase, and one or more omega peptidase. In some embodiments, at least one of the one or more protein degrading components is one or more chemical compounds. In some embodiments, at least one of the one or more protein degrading components is one or more recombinant protein degrading components.

Figure 8:
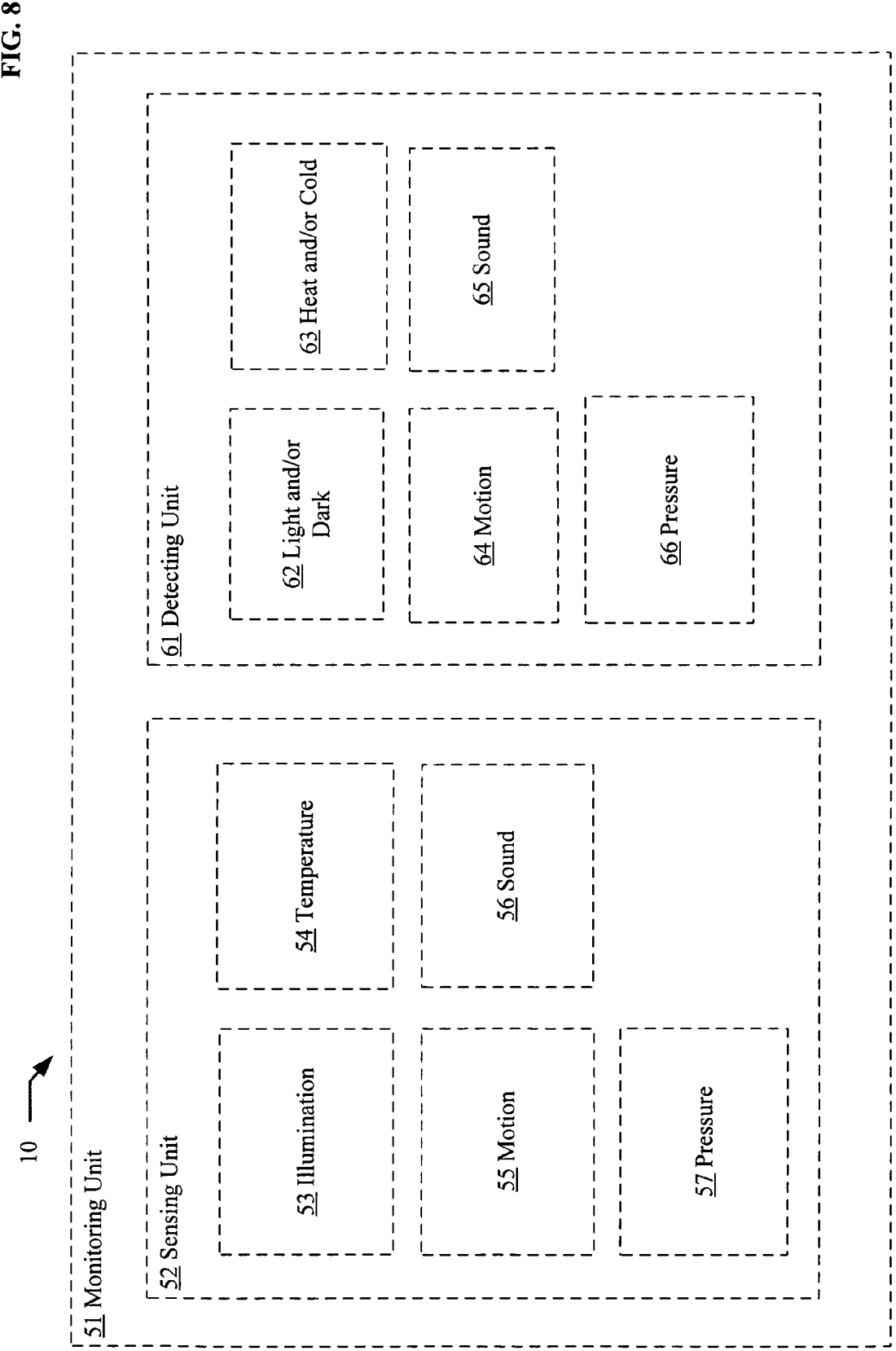
FIG. 8 shows schematics of illustrative embodiments of the apparatus of FIG. 5, with illustrative examples of a monitoring unit.
Figure 10:
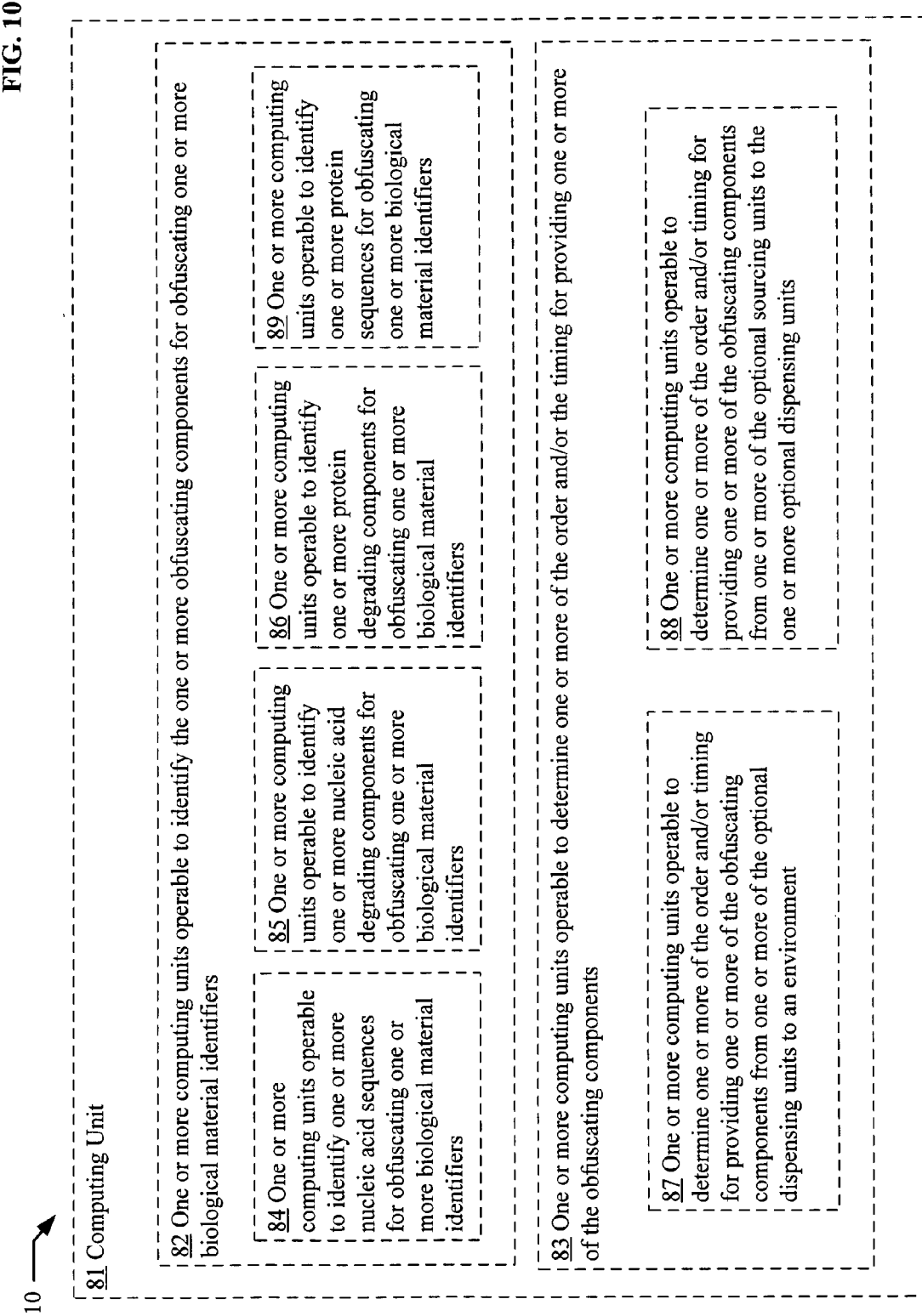
FIG. 10 shows schematics of illustrative embodiments of the apparatus of FIG. 5, with illustrative examples of a computing unit.

FIG. 8 shows a schematic 10 of illustrative embodiments of the apparatus 11 of FIG. 5, with specific illustrative embodiments of one or more monitoring units 51, operable to sense, measure and/or detect one or more changes in environmental conditions, including one or more optional sensing units 52 and/or one or more optional detecting units 61. In some embodiments, the one or more optional sensing units 52 and the one or more optional detecting units 61 are optionally the same unit. In some embodiments, one or more apparatus includes, but is not limited to, one or more dispensing units 15 and one or more monitoring units 51. In some embodiments, the one or more dispensing units 15 and the one or more monitoring units 51 are the same one or more units. In some embodiments, one or more apparatus includes, but is not limited to, one or more dispensing units 15, one or more sourcing units 31, and one or more monitoring units 51. In some embodiments, the one or more dispensing units 15, one or more sourcing units 31, and the one or more monitoring units 51 are the same unit.

On some embodiments, one or more sensing units 52 are optionally operable to sense one or more of levels of illumination, temperature, motion, pressure, and/or sound. Specific illustrative embodiments of the one or more sensing units 52 optionally include, but are not limited to, one or more optional illumination sensing units 53, one or more optional temperature sensing units 54, one or more optional motion sensing units 55, one or more optional pressure sensing units 57, and/or one or more optional sound level sensing units 56. In some embodiments, one or more of the sensing units 52 are the same unit.

One or more detecting units 61 are optionally operable to detect one or more of light and/or dark, heat and/or cold, motion, pressure, and/or sound. Specific illustrative embodiments of the one or more detecting units 61 optionally include, but are not limited to, one or more optional light and/or dark detecting units 62, one or more optional heat and/or cold detecting units 63, one or more optional motion detecting units 64, one or more optional pressure detecting units 66, and/or one or more optional sound detecting units 65. In some embodiments, one or more of the detecting units 61 are the same unit.

In some embodiments, one or more apparatus includes one or more monitoring units, optionally including one or more sensing units and/or one or more detecting units, wherein the one or more monitoring units are optionally operable to monitor one or more of presence or absence, amount, and/or identity of one or more nucleic acid sequences and/or target nucleic acid sequences. In illustrative embodiments, the one or more apparatus may includes one or more sensors, one or more dyes, and/or one or more enzymes for use in detecting, sensing, and/or monitoring the presence or absence, amount, and/or identity of one or more nucleic acid sequences and/or one or more target nucleic acid sequences.

In some embodiments, one or more apparatus includes one or more monitoring units, optionally including one or more sensing units and/or one or more detecting units, wherein the one or more monitoring units are optionally operable to monitor one or more of presence or absence, amount, and/or identity of one or more protein sequences and/or target protein sequences. In illustrative embodiments, the one or more apparatus may includes one or more sensors, one or more dyes, and/or one or more enzymes for use in detecting, sensing, and/or monitoring the presence or absence, amount, and/or identity of one or more protein sequences and/or one or more target protein sequences.

In some embodiments, one or more apparatus further includes one or more sensors optionally operable to sense light, noise, heat, pressure, and/or motion. In some embodiments, the one or more sensors are optionally selected from the group consisting of motion sensors, illumination sensors, sound sensors, pressure sensors and temperature sensors. In some embodiments, one or more apparatus further includes one or more detectors optionally operable to detect light, noise, heat, pressure and/or motion. In some embodiments, the one or more detectors are optionally selected from the group consisting of motion detectors, illumination detectors, noise detectors, pressure detectors, and temperature detectors.

In some embodiments, one or more monitoring units (optionally one or more sensing units and/or one or more detecting units) may activate one or more dispensing units to provide one or more obfuscating components to an environment based on one or more readings of movement, heat, pressure, light and/or other environmental or other factors indicating the presence, arrival or departure of a person and/or other animal and/or one or more target nucleic acid sequences and/or target protein sequences. Based on the sensed factors, the dispenser may be activated immediately or after some delay.

In some embodiments, one or more apparatus includes one or more, optionally wide-area, dispersing device operable to optionally automatically provide the one or more compositions to the environment at least partially based on readings from one or more monitoring units, optionally one or more sensors and/or one or more detectors. In some embodiments, one or more apparatus includes one or more, optionally wide-area, dispersing device operable to optionally automatically provide the one or more compositions to the environment at least partially based on changes in one or more environmental conditions, wherein the one or more environmental conditions are optionally selected from the group consisting of sound, light, pressure, motion and temperature.

FIG. 9 shows a schematic 10 of illustrative embodiments of the apparatus 11 of FIG. 5, with specific illustrative embodiments of one or more controller units 71, including one or more optional controller units operable to control one or more of the one or more functions and/or activities of the apparatus 11, including but not limited to, one or more of the one or more functions and/or activities of one or more optional dispensing units 15, one or more optional sourcing units 31, and/or one or more optional monitoring units 51.

Specific illustrative embodiments of the optional one or more controller units include, but are not limited to, one or more controller units optionally operable to control one or more activities and/or functions of one or more dispensing units 72, one or more controller units optionally operable to control one or more activities and/or functions of one or more sourcing units 73, one or more controller units optionally operable to control one or more activities and/or functions of one or more monitoring units 74, and/or one or more controller units optionally operable to control one or more activities and/or functions of one or more remote-control units 75. In some embodiments, one or more of the one or more controller units are the same unit, and are optionally the same as one or more computing units.

In some embodiments, one or more apparatus 11 includes, but is not limited to, one or more dispensing units 15 and one or more controller units 71. In some embodiments, the one or more dispensing units 15 and the one or more controller units 71 are the same one or more units. In some embodiments, one or more apparatus 11 includes, but is not limited to one or more dispensing units 15, one or more sourcing units 31, one or more controller units 71, and one or more monitoring units 51. In some embodiments, the one or more dispensing units 15, one or more sourcing units 31, the one or more controller units 71, and the one or more monitoring units 51 are the same unit.

In some embodiments, one or more apparatus further includes one or more controllers operable to control providing one or more obfuscating components to the environment. In some embodiments, one or more apparatus further includes one or more controllers operable to control the timing, the order, and/or the sequence for providing one or more obfuscating components to the environment. In some embodiments, the one or more controllers are operable to control optionally automatically providing the one or more compositions to the environment, optionally at least partially based on readings from one or more monitoring units, optionally one or more of one or more sensors or one or more detectors. Based on the readings from one or more monitoring units, the one or more controllers may activate the one or more dispensing units to provide one or more obfuscating components immediately, or after a delay.

In some embodiments, one or more apparatus comprises one or more devices for providing one or more obfuscating components to an environment; one or more obfuscating components; one or more controllers operable to control providing the one or more obfuscating components to the environment at least partially based on the readouts from one or more sensors; and the one or more sensors, wherein the one or more sensors are optionally operable to sense light, noise, heat, pressure or motion. In some embodiments, one or more apparatus comprises one or more devices for providing one or more obfuscating components to an environment; one or more obfuscating components; one or more controllers operable to control providing the one or more obfuscating components to the environment at least partially based on the readouts from one or more detectors; and the one or more detectors, wherein the one or more detectors are optionally operable to sense light, noise, heat, pressure and/or motion.

In some embodiments, one or more apparatus includes one or more one or more controllers, wherein the one or more controllers are optionally one or more non-electrical controllers, optionally selected from the group consisting of mechanical timers and thermal switches. In some embodiments, the one or more controllers are optionally one or more electrical controllers. In some embodiments, one or more apparatus may be activated to provide one or more obfuscating components at one or more fixed intervals or at one or more non-uniform intervals.

In some embodiments, one or more apparatus includes one or more, optionally wide-area, dispersing device operable to optionally automatically provide the one or more compositions to the environment at least partially based on one or more timers, wherein the one or more timers are optionally selected from the group consisting of one or more mechanical timers, one or more electrical timers, and one or more thermal switches.

In some embodiments, one or more apparatus includes one or more controllers, wherein the one or more controllers are operable to control co-localizing one or more of the one or more carrier components with one or more of the one or more obfuscating components before providing the one or more obfuscating components to the environment. In some embodiments, the one or more controllers are operable to control co-localizing one or more of the one or more first carrier components with one or more of the one or more nucleic acid depositing components to form one or more first compositions before providing the one or more nucleic acid depositing components to the environment. In some embodiments, the one or more controllers are operable to control co-localizing one or more of the one or more fourth carrier components with one or more of the one or more protein depositing components to form one or more fourth compositions before providing the one or more protein depositing components to the environment. In some embodiments, the one or more controllers are operable to control co-localizing one or more of the one or more second carrier components with one or more of the one or more nucleic acid degrading components to form one or more second compositions before providing the one or more nucleic acid degrading components to the environment. In some embodiments, the one or more controllers are operable to control co-localizing one or more of the one or more third carrier components with one or more of the one or more protein degrading components to form one or more third compositions before providing the one or more protein degrading components to the environment.

In some embodiments, one or more apparatus includes one or more controllers, wherein the one or more controllers are operable to control one or more of activation or inactivation of one or more of the one or more nucleic acid and/or one or more protein degrading components, optionally by co-localizing one or more activating or inactivating second and/or third carrier components with the one or more nucleic acid and/or one or more protein degrading components.

In some embodiments, one or more apparatus includes one or more controllers, wherein the one or more controllers are optionally operable to control the co-localization of one or more of the one or more first compositions, one or more fourth compositions, one or more second compositions, and/or one or more third compositions prior to release of the one or more compositions from the dispensing device. In some embodiments, the one or more controllers are operable to control the separate release of one or more of the one or more compositions. In some embodiments, the one or more controllers are optionally operable to control the sequential release one or more of the one or more compositions. In some embodiments, the one or more first compositions are released prior to the one or more second compositions. In some embodiments, the one or more third compositions are released prior to the one or more second compositions. In some embodiments, the one or more first compositions are released prior to the one or more fourth compositions. In some embodiments, the one or more fourth compositions are released prior to the one or more third compositions.

In some embodiments, one or more apparatus includes one or more controllers, wherein the one or more controllers are optionally operable to control one or more wireless or robotic attachments to the one or more apparatus optionally for positioning the one or more attachments in crevices, nooks, or hard to reach areas. In some embodiments, the one or more wireless or robotic attachments may be controlled from the exterior remotely, or may be controlled by software, hardware, or firmware, for example.

In some embodiments, one or more apparatus includes one or more controllers, wherein the one or more controllers are optionally operable to control the positioning of one or more moveable apparatus optionally for positioning the one or more apparatus for access to crevices, nooks, or hard to reach areas, and/or optionally for deployment prior to use and/or storage after use. In some embodiments, the one or more wireless or robotic attachments may be controlled from the exterior remotely, or may be controlled by software, hardware, or firmware, for example.

In some embodiments, one or more apparatus comprises one or more devices for providing one or more obfuscating components to an environment; one or more obfuscating components; and one or more controllers operable to control providing the one or more obfuscating components to the environment, and wherein the one or more controllers are optionally operable to control the timing, the order, and/or the sequence for providing the one or more obfuscating components to the environment.

In some embodiments, one or more apparatus comprises one or more devices for providing one or more obfuscating components to an environment; one or more obfuscating components; and one or more controllers operable to control providing the one or more obfuscating components to the environment, and wherein the one or more obfuscating components are selected from the group consisting of nucleic acid depositing components, protein depositing components, nucleic acid degrading components, and protein degrading components.

In some embodiments, one or more controller units include one or more remote control units. In some embodiments, the one or more remote control units are optionally operable to control one or more aspects of the one or more dispensing units, optional sourcing units, and/or optional monitoring units.

FIG. 10 shows a schematic 10 of illustrative embodiments of the apparatus 11 of FIG. 5, with specific illustrative embodiments of one or more computing units 81, including one or more computing units operable to identify the one or more obfuscating components for obfuscating one or more biological material identifiers 82, and/or one or more computing units operable to determine one or more of the order and/or the timing for providing one or more of the obfuscating components 83. In some embodiments, one or more of the computing units are optionally the same unit.

In some embodiments, one or more apparatus 11 include, but are not limited to, one or more dispensing units 15 and one or more computing units 81. In some embodiments, the one or more dispensing units 15 and the one or more computing units 81 are the same one or more units. In some embodiments, one or more apparatus 11 optionally includes, but is not limited to, one or more dispensing units 15, one or more controller units 71, one or more sourcing units 31, and one or more monitoring units 51 and one or more computing units 81. In some embodiments, the one or more dispensing units 15, the one or more sourcing units 31, the one or more controller units 71, the one or more computing units 81, and the one or more monitoring units 31 are the same unit. In some embodiments one or more of the one or more controller units are optionally the same as one or more of the one or more computing units.

Specific illustrative embodiments of the one or more computing units 82 include, but are not limited to, one or more computing units operable to identify one or more nucleic acid sequences for obfuscating one or more biological material identifiers 84, one or more protein sequences for obfuscating one or more biological material identifiers 89, one or more computing units operable to identify one or more nucleic acid degrading components for obfuscating one or more biological material identifiers 85, and/or one or more computing units operable to identify one or more protein degrading components for obfuscating one or more biological material identifiers 86. One or more of the one or more computing units is operable to perform one or more of the computing and/or determining methods described herein.

Specific illustrative embodiments of the one or more computing units 83 include, but are not limited to, one or more computing units operable to determine one or more of the order and/or the timing for providing one or more of the obfuscating components from one or more of the optional dispensing units to an environment 87, optionally at least partially based on information from one or more of the optional monitoring units; and/or one or more computing units operable to determine one or more of the order and/or the timing for providing one or more of the obfuscating components from one or more of the optional sourcing units to the one or more optional dispensing units 88, optionally at least partially based on information from one or more of the optional monitoring units.

In some embodiments, the one or more computing units is optionally operable to determine the timing and/or order for co-localizing one or more obfuscating components and/or one or more carrier components prior to dispensing the one or more compositions from the one or more dispensing units. In some embodiments, the one or more computing units is optionally operable to determine the timing and/or order for co-localizing one or more activating components and/or inactivating components with one or more obfuscating components and/or one or more carrier components prior to dispensing from the one or more dispensing units.

In one aspect, the disclosure is drawn to one or more kits, comprising one or more devices for providing one or more obfuscating components to an environment; one or more obfuscating components; and one or more instructions. One or more of the one or more kits are optionally operable to perform one or more of the methods described herein, and/or to include one or more of the apparatus described herein, and/or to include one or more of the compositions described herein.

In some embodiments, one or more kits include one or more dispensing devices designed to be installed in one or more fixed locations. In some embodiments, the one or more kits further comprise one or more attachments for providing the one or more obfuscating components to an environment, optionally in a wide area. In some embodiments, the one or more kits further comprise one or more installation components. In some embodiments, one or more kits further comprise one or more remote control units and/or one or more sensors and/or one or more detectors. In some embodiments, one or more kits further comprise one or more sourcing units, one or more controller units and/or one or more computing units. In some embodiments, one or more instructions include one or more instructions for use of the one or more dispersing devices, one or more instructions for assembly of the one or more dispersing devices, one or more instructions for installation of the one or more dispensing devices, and/or one or more warranties.

In some embodiments, one or more kits comprise one or more devices for providing one or more nucleic acid sequences to an environment; one or more nucleic acid sequences; and one or more instructions. In some embodiments, one or more kits for providing one or more nucleic acid sequences to an environment optionally include a focused dispersion device, such as, but not limited to, a squeeze tube or sprayer. In some embodiments, the one or more kits further comprise one or more nucleic acid and/or protein degrading components, and optionally one or more second and/or one or more third carrier components.

In some embodiments, one or more kits comprise one or more devices for providing one or more protein sequences to an environment; one or more protein sequences; and one or more instructions. In some embodiments, one or more kits for providing one or more protein sequences to an environment optionally include a focused dispersion device, such as, but not limited to, a squeeze tube or sprayer. In some embodiments, the one or more kits further comprise one or more nucleic acid and/or protein degrading components, and optionally one or more second and/or one or more third carrier components.

In some embodiments, one or more kits comprise one or more wide area dispersing devices; one or more nucleic acid degrading components; one or more second carriers; and one or more instructions. In some embodiments, one or more kits comprise one or more automatic dispersing device; one or more nucleic acid degrading components; one or more second carriers; and one or more instructions. In some embodiments, one or more kits comprise one or more remote-controlled dispersing device; one or more nucleic acid degrading components; one or more second carriers; and one or more instructions. In some embodiments, the one or more kits further comprise one or more protein degrading components, and optionally one or more third carriers.

In some embodiments, one or more kits comprise one or more wide area dispersing device; one or more protein degrading components; one or more third carriers; and one or more instructions. In some embodiments, one or more kits comprise one or more automatic dispersing device; one or more protein degrading components; one or more third carriers; and one or more instructions. In some embodiments, one or more kits comprise one or more remote-controlled dispersing device; one or more protein degrading components; one or more third carriers; and one or more instructions.

In some embodiments, the one or more wide area dispersing devices are in a form selected from the group consisting of a fogger, a grenade, a sprinkler, and a mister. In some embodiments, the one or more, optionally wide area, dispersing devices are manually controlled. In some embodiments, the one or more, optionally wide area, dispersing devices are automatically-controlled optionally at least partially based on readouts from one or more sensors. In some embodiments, the one or more, optionally wide area, dispersing devices are remotely-controlled, optionally at least partially based on readouts from one or more sensors. In some embodiments, the one or more, optionally wide area, dispersing devices are wirelessly remotely-controlled.

In one aspect, the disclosure is drawn to one or more methods comprising receiving a first input associated with a first possible dataset, the first possible dataset including data representative of one or more target biological material identifiers; and determining data representative of one or more obfuscating components for one or more of the one or more target biological material identifiers based on the first possible dataset. One or more of these methods may be used as part of one or more methods of identity obfuscation and/or implemented on one or more apparatus 410 for identity obfuscation.

Figure 11:
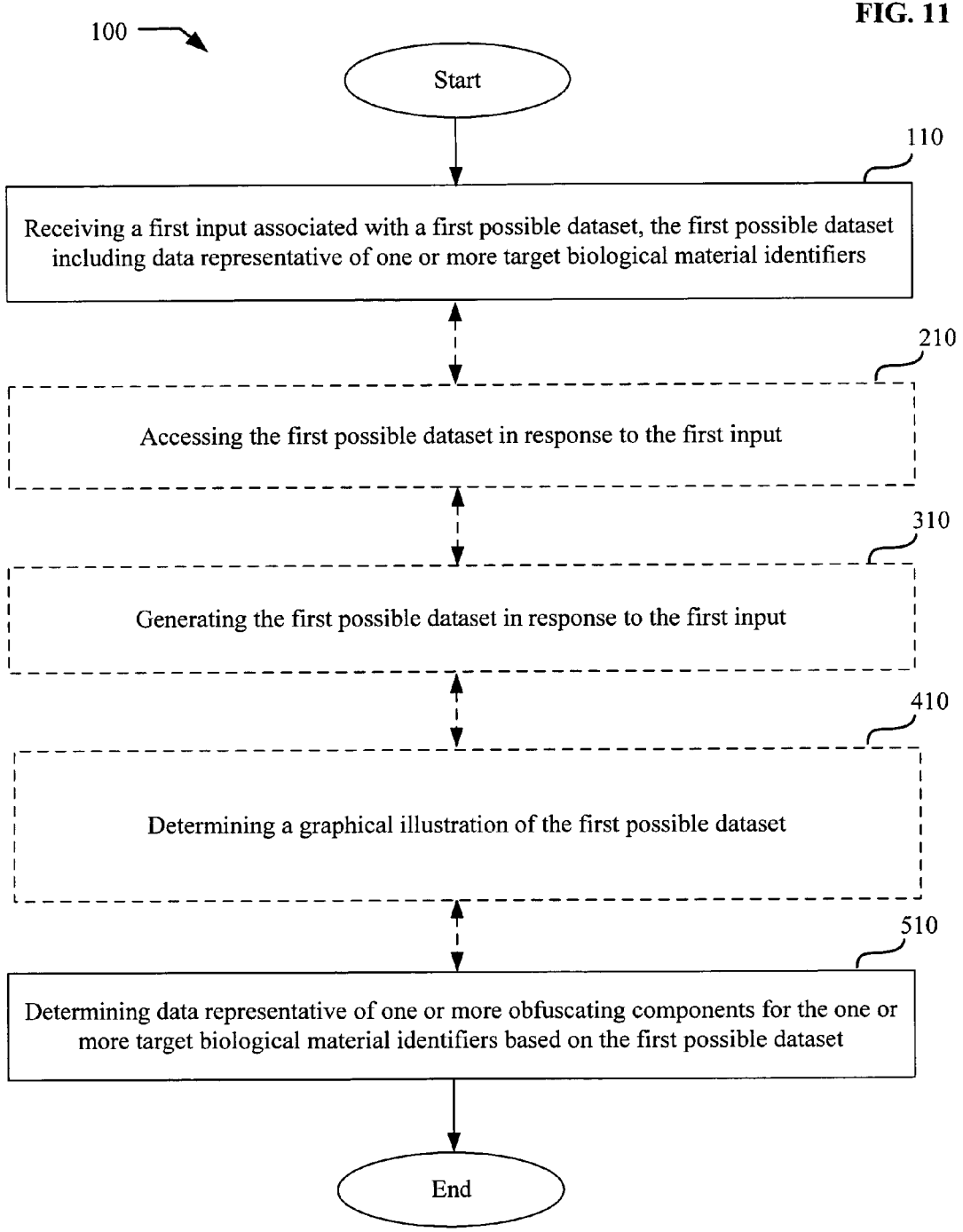
FIG. 11 shows an operational flow representing illustrative embodiments of operations related to determining data representative of one or more obfuscating components for obfuscating the one or more target biological material identifiers based on a first possible dataset.

FIG. 11 shows an operational flow 100 representing illustrative embodiments of operations related to determining data representative of one or more obfuscating components for the one or more target biological material identifiers based on a first possible dataset. In FIG. 11, and in the following figures that include various illustrative embodiments of operational flows, discussion and explanation may be provided with respect to apparatus and methods described herein, and/or with respect to other examples and contexts. The operational flows may also be executed in a variety of other contexts and environments, and or in modified versions of those described herein. In addition, although some of the operational flows are presented in sequence, the various operations may be performed in various repetitions, concurrently, and/or in other orders than those that are illustrated.

After a start operation, the operational flow 100 moves to a receiving operation 110 where receiving a first input associated with a first possible dataset, the first possible dataset including data representative of one or more target biological material identifiers. For example, a first input may include data representative of a target nucleic acid sequence, a target protein sequence, a target ethnic group, a target gender, a target population, a target geographic region, a target racial group, a target genetic background, a target genetic characteristic, and/or a target genetic abnormality, or other target identifying characteristics. A first input may also include data representative of the percent identity and/or percent similarity of nucleic acid sequences to one or more target nucleic acid sequences and/or protein sequences to one or more target protein sequences.

An optional accessing operation 210 accesses the first possible dataset in response to the first input. For example, data representative of one or more target biological material identifiers may be accessed. For example, data representative of a target nucleic acid sequence, a target protein sequence, a target ethnic group, a target gender, a target population, a target geographic region, a target racial group, a target genetic background, a target genetic characteristic, and/or a target genetic abnormality, or other target identifying characteristics may be accessed. Data representative of the percent identity and/or percent similarity of nucleic acid sequences to one or more target nucleic acid sequences and/or protein sequences to one or more target protein sequences may also be accessed.

An optional generating operation 310 generates the first possible dataset in response to the first input. For example, data representative of one or more target biological material identifiers may be generated. For example, data representative of a target nucleic acid sequence, a target protein sequence, a target ethnic group, a target gender, a target population, a target geographic region, a target racial group, a target genetic background, a target genetic characteristic, and/or a target genetic abnormality, or other target identifying characteristics may be generated. Data representative of the percent identity and/or percent similarity of nucleic acid sequences to one or more target nucleic acid sequences and/or protein sequences to one or more target protein sequences may also be generated.

An optional determining operation 410 determines a graphical illustration of the first possible dataset. For example, data representative of one or more target biological material identifiers may be graphically represented. For example, data representative of a target nucleic acid sequence, a target protein sequence, a target ethnic group, a target gender, a target population, a target geographic region, a target racial group, a target genetic background, a target genetic characteristic, and/or a target genetic abnormality, or other target identifying characteristics may be graphically represented. Data representative of the percent identity and/or percent similarity of nucleic acid sequences to one or more target nucleic acid sequences and/or protein sequences to one or more target protein sequences may also be graphically represented.

Then, a determining operation 510, determines data representative of one or more obfuscating components for obfuscating one or more target biological material identifiers based on a first possible dataset. For example, data representative of one or more obfuscating components for obfuscating one or more target biological material identifiers based on data representative of a target nucleic acid sequence, a target protein sequence, a target ethnic group, a target gender, a target population, a target geographic region, a target racial group, a target genetic background, a target genetic characteristic, and/or a target genetic abnormality, or other target identifying characteristics may be determined. Data representative of one or more obfuscating components for obfuscating one or more target biological material identifiers based on data representative of the percent identity and/or percent similarity of nucleic acid sequences to one or more target nucleic acid sequences and/or protein sequences to one or more target protein sequences may also be determined. One or more obfuscating components may include, but are not limited to, one or more nucleic acid degrading components, one or more protein degrading components, and/or one or more nucleic acid sequence depositing components.

Operations 110 to 510 may be performed with respect to a digital representation (e.g. digital data) of, for example, data representative of one or more target biological material identifiers, including but not limited to, a target nucleic acid sequence, a target protein sequence, a target ethnic group, a target gender, a target population, a target geographic region, a target racial group, a target genetic background, a target genetic characteristic, and/or a target genetic abnormality, or other target identifying characteristics, and/or data representative of the percent identity and/or percent similarity of nucleic acid sequences to one or more target nucleic acid sequences and/or protein sequences to one or more target protein sequences. The logic may accept a digital or analog (for conversion into digital) representation of an input and/or provide a digitally-encoded representation of a graphical illustration, where the input may be implemented and/or accessed locally or remotely.

Operations 110 to 510 may be performed related to either a local or a remote storage of the digital data, or to another type of transmission of the digital data. In addition to inputting, accessing querying, recalling, calculating, determining or otherwise obtaining the digital data, operations may be performed related to storing, assigning, associating, displaying or otherwise archiving the digital data to a memory, including for example, sending and/or receiving a transmission of the digital data from a remote memory. Accordingly, any such operations may involve elements including at least an operator (e.g. human or computer) directing the operation, a transmitting computer, and/or receiving computer, and should be understood to occur in the United States as long as at least one of these elements resides in the United States.

Figure 12:
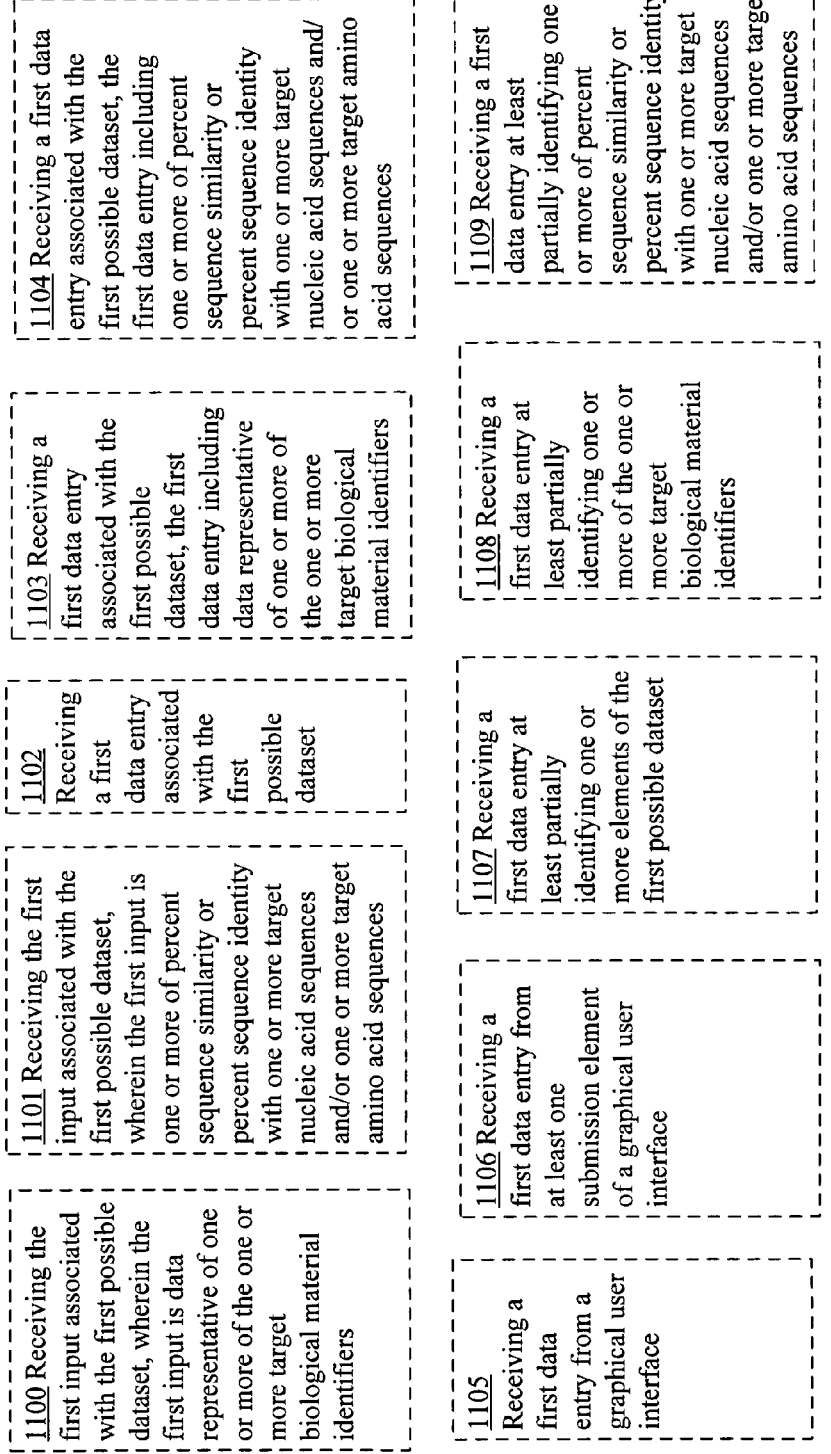
FIG. 12 shows optional embodiments of the operational flow of FIG. 11.

FIG. 12 illustrates optional embodiments of the operational flow 100 of FIG. 11. FIG. 12 shows illustrative embodiments of the receiving operation 110, receiving a first input associated with a first possible dataset, the first possible dataset including data representative of one or more target biological material identifiers, including operations receiving types of inputs and data entry and may include at least one additional operation. Receiving operations may optionally include, but are not limited to, operation 1100, operation 1101, operation 1102, operation 1103, operation 1104, operation 1105, operation 1106, operation 1107, operation 1108, and/or operation 1109.

At the optional operation 1100, receiving a first input associated with a first possible dataset comprises receiving the first input associated with the first possible dataset, wherein the first input is data representative of one or more of the one or more target biological material identifiers. In some embodiments, one or more of the one or more target biological material identifiers are selected from the group consisting of one or more genetic characteristics, one or more nucleic acid sequences, one or more protein sequences, one or more genomes, one or more demographic groups, one or more ethnic groups, one or more racial groups, one or more populations, one or more clades, one or more nationalities, one or more genders, and one or more geographic regions. In some embodiments, one or more of the one or more genetic characteristics are selected from the group consisting of age, telomere length, physical identifiers, mitochondrial nucleic acid sequences, genetic abnormalities, genetic diseases, and chromosomal abnormalities.

At the optional operation 1101, receiving a first input associated with a first possible dataset comprises receiving the first input associated with the first possible dataset, wherein the first input is one or more of one or more percent sequence similarity or one or more percent sequence identity with one or more target nucleic acid sequences and/or one or more target protein sequences. In some embodiments, the one or more percent sequence similarity and/or one or more percent sequence identity is one or more integer percent from 5% to 100%.

At the optional operation 1102 and/or 1103, receiving a first input associated with a first possible dataset comprises receiving a first data entry associated with the first possible dataset, the first data entry optionally including data representative of one or more of the one or more target biological material identifiers. In some embodiments, one or more of the one or more target biological material identifiers are selected from the group consisting of one or more genetic characteristics, one or more nucleic acid sequences, one or more protein sequences, one or more genomes, one or more demographic groups, one or more ethnic groups, one or more racial groups, one or more populations, one or more clades, one or more nationalities, one or more genders, and one or more geographic regions. In some embodiments, one or more of the one or more genetic characteristics are selected from the group consisting of age, telomere length, physical identifiers, mitochondrial nucleic acid sequences, genetic abnormalities, genetic diseases, and chromosomal abnormalities.

At the optional operation 1104, receiving a first input associated with a first possible dataset comprises receiving a first data entry associated with the first possible dataset, the first data entry including one or more of one or more percent sequence similarity or one or more percent sequence identity with one or more target nucleic acid sequences and/or target protein sequences. In some embodiments, the one or more percent sequence similarity and/or one or more percent sequence identity is one or more integer percent from 5% to 100%.

At the optional operation 1105 and/or 1106 and/or 1107, receiving a first input associated with a first possible dataset comprises receiving a first data entry from a graphical user interface, optionally from at least one submission element of a graphical user interface, and optionally at least partially identifying one or more elements of the first possible dataset. In some embodiments, the one or more elements include, but are not limited to, percent of obfuscation, method of obfuscation, and biological material identifiers for obfuscation. In some embodiments, the biological materials are partially or completely obfuscated. In some embodiments, the percent of obfuscation ranges from an integer percent from 5% to 100%. In some embodiments, the percent of obfuscation includes, but is not limited to, 10%, 15%, 20%, 25%, 30%, 35%, 40%, 45%, 50%, 55%, 60%, 65%, 70%, 75%, 80%, 85%, 90%, 95% and/or 100% and/or may be a range from 10% to 95%, 25% to 95%, 30% to 95%, 50% to 9%, 75% to 95%, 10% to 75%, 10% to 50%, 10% to 25%, 25% to 95%, 25% to 75, 25% to 50%, 50% to 95%, 50% to 75%, and/or 75% to 95%.

In some embodiments, the method of obfuscation includes, but is not limited to, one or more of nucleic acid sequence deposition, protein sequence deposition, nucleic acid sequence degradation, and/or protein degradation. In some embodiments, deposition of one or more nucleic acid sequences includes one or more first carriers, the one or more first carriers optionally including one or more natural carriers (one or more biological materials) and/or one or more non-natural carriers. In some embodiments, deposition of one or more protein sequences includes one or more fourth carriers, the one or more fourth carriers optionally including one or more natural carriers (one or more biological materials) and/ or one or more non-natural carriers. In some embodiments, the one or more natural carriers are selected from the group consisting of skin, hair, saliva, semen, urine and feces. In some embodiments, nucleic acid degradation is enzymatic and/or non-enzymatic. In some embodiments, protein degradation is enzymatic and/or non-enzymatic.

At the optional operation 1108, receiving a first input associated with a first possible dataset comprises receiving a first data entry at least partially identifying one or more of the one or more target biological material identifiers. In some embodiments, one or more of the one or more target biological material identifiers are selected from the group consisting of one or more genetic characteristics, one or more nucleic acid sequences, one or more protein sequences, one or more genomes, one or more demographic groups, one or more ethnic groups, one or more racial groups, one or more populations, one or more clades, one or more nationalities, one or more genders, and one or more geographic regions. In some embodiments, one or more of the one or more genetic characteristics are selected from the group consisting of age, telomere length, physical identifiers, mitochondrial nucleic acid sequences, genetic abnormalities, genetic diseases, and chromosomal abnormalities.

At the optional operation 1109, receiving a first input associated with a first possible dataset comprises receiving a first data entry at least partially identifying one or more of one or more percent sequence similarity or one or more percent sequence identity with one or more target nucleic acid sequences and/or one or more target protein sequences. In some embodiments, the one or more percent sequence similarity and/or one or more percent sequence identity is one or more integer percent from 5% to 100%.

Figure 13:
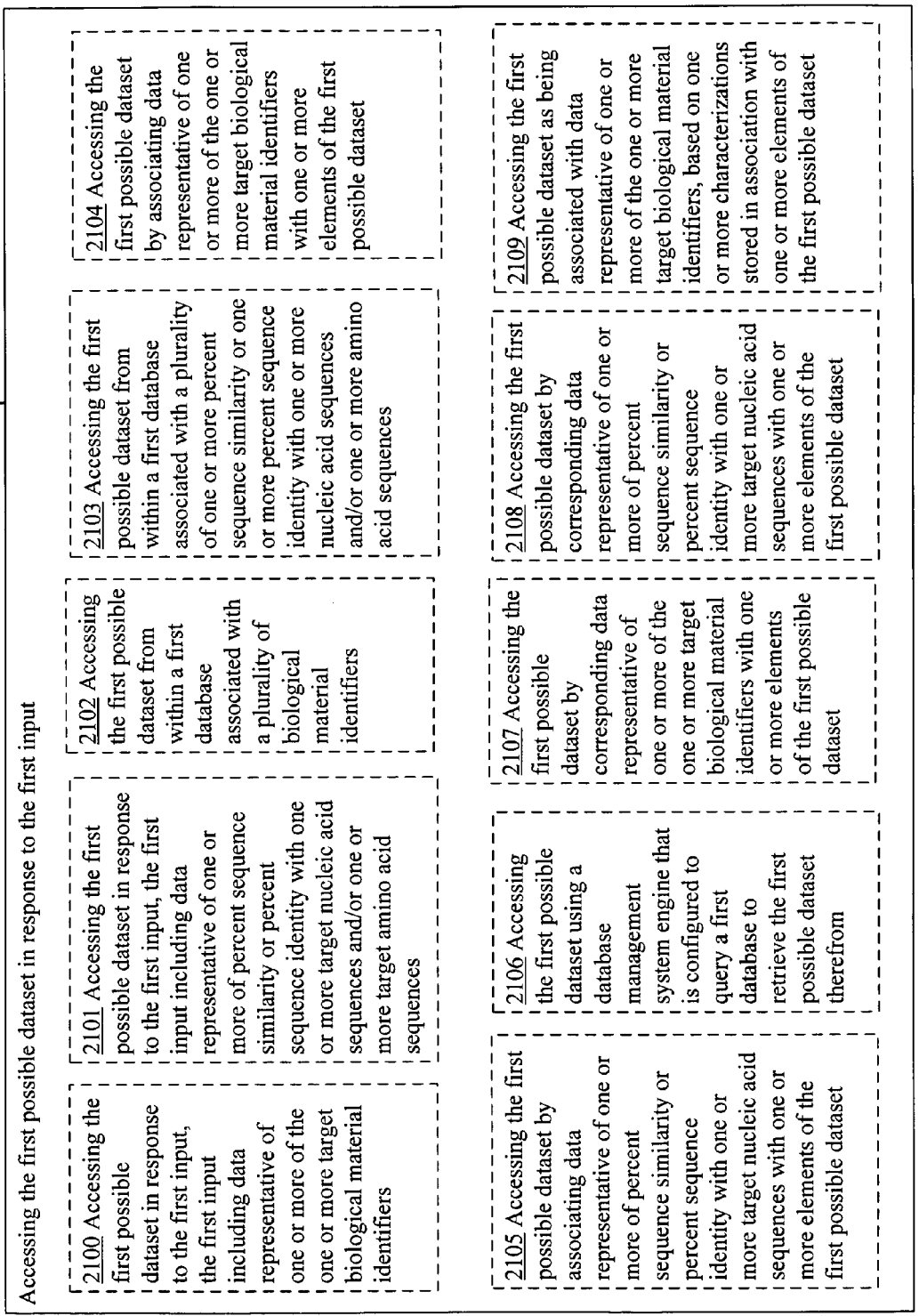
FIG. 13 shows optional embodiments of the operational flow of FIG. 11.

FIG. 13 and FIG. 14 illustrate optional embodiments of the operational flow 100 of FIG. 11. FIG. 13 and FIG. 14 show illustrative embodiments of the optional accessing operation 210, including operations accessing the first possible dataset in response to the first input, and may include at least one additional operation. Accessing operations may optionally include, but are not limited to, operation 2100, operation 2101, operation 2102, operation 2103, operation 2104, operation 2105, operation 2106, operation 2107, operation 2108, operation 2109, operation 2110, operation 2111, operation 2112, operation 2113, operation 2114, operation 2115, operation 2116, operation 2117, operation 2118, operation 2119, operation 2120, operation 2121, and/or operation 2122.

At the optional operation 2100, accessing the first possible dataset in response to the first input comprises accessing the first possible dataset in response to the first input, the first input including data representative of one or more of the one or more target biological material identifiers. In some embodiments, one or more of the one or more target biological material identifiers are selected from the group consisting of one or more genetic characteristics, one or more nucleic acid sequences, one or more protein sequences, one or more genomes, one or more demographic groups, one or more ethnic groups, one or more racial groups, one or more populations, one or more clades, one or more nationalities, one or more genders, and one or more geographic regions. In some embodiments, one or more of the one or more genetic characteristics are selected from the group consisting of age, telomere length, physical identifiers, mitochondrial nucleic acid sequences, genetic abnormalities, genetic diseases, and chromosomal abnormalities.

At the optional operation 2101, accessing the first possible dataset in response to the first input comprises accessing the first possible dataset in response to the first input, the first input including data representative of one or more of one or more percent sequence similarity or one or more percent sequence identity with one or more target nucleic acid sequences and/or target protein sequences. In some embodiments, the one or more percent sequence similarity and/or one or more percent sequence identity is one or more integer percent from 5% to 100%.

At the optional operation 2102, accessing the first possible dataset in response to the first input comprises accessing the first possible dataset from within a first database associated with a plurality of biological material identifiers. In some embodiments, one or more of the one or more biological material identifiers are selected from the group consisting of one or more genetic characteristics, one or more nucleic acid sequences, one or more protein sequences, one or more genomes, one or more demographic groups, one or more ethnic groups, one or more racial groups, one or more populations, one or more clades, one or more nationalities, one or more genders, and one or more geographic regions. In some embodiments, one or more of the one or more genetic characteristics are selected from the group consisting of age, telomere length, physical identifiers, mitochondrial nucleic acid sequences, genetic abnormalities, genetic diseases, and chromosomal abnormalities.

At the optional operation 2103, accessing the first possible dataset in response to the first input comprises accessing the first possible dataset from within a first database associated with a plurality of one or more percent sequence similarity or one or more percent sequence identity with one or more nucleic acid sequences and/or one or more protein sequences. In some embodiments, the one or more percent sequence similarity and/or one or more percent sequence identity is one or more integer percent from 5% to 100%.

At the optional operation 2104, accessing the first possible dataset in response to the first input comprises accessing the first possible dataset by associating data representative of one or more of the one or more target biological material identifiers with one or more elements of the first possible dataset. In some embodiments, one or more of the one or more target biological material identifiers are selected from the group consisting of one or more genetic characteristics, one or more nucleic acid sequences, one or more protein sequences, one or more genomes, one or more demographic groups, one or more ethnic groups, one or more racial groups, one or more populations, one or more clades, one or more nationalities, one or more genders, and one or more geographic regions. In some embodiments, one or more of the one or more genetic characteristics are selected from the group consisting of age, telomere length, physical identifiers, mitochondrial nucleic acid sequences, genetic abnormalities, genetic diseases, and chromosomal abnormalities.

In some embodiments, the one or more elements include, but are not limited to, percent of obfuscation, method of obfuscation, and biological material identifiers for obfuscation. In some embodiments, the biological materials are partially or completely obfuscated. In some embodiments, the percent of obfuscation ranges from an integer percent from 5% to 100%.

In some embodiments, the method of obfuscation includes, but is not limited to, one or more of nucleic acid sequence deposition, protein sequence deposition, nucleic acid sequence degradation, and/or protein degradation. In some embodiments, deposition of one or more nucleic acid sequences includes one or more first carriers, the one or more first carriers optionally including one or more natural carriers (one or more biological materials) and/or one or more non-natural carriers. In some embodiments, deposition of one or more protein sequences includes one or more fourth carriers, the one or more fourth carriers optionally including one or more natural carriers (one or more biological materials) and/or one or more non-natural carriers. In some embodiments, the one or more natural carriers are selected from the group consisting of skin, hair, saliva, semen, urine and feces. In some embodiments, nucleic acid degradation is enzymatic and/or non-enzymatic. In some embodiments, protein degradation is enzymatic and/or non-enzymatic.

At the optional operation 2105, accessing the first possible dataset in response to the first input comprises accessing the first possible dataset by associating data representative of one or more of one or more percent sequence similarity or one or more percent sequence identity with one or more target nucleic acid sequences and/or one or more target protein sequences with one or more elements of the first possible dataset. In some embodiments, the one or more percent sequence similarity and/or one or more percent sequence identity is one or more integer percent from 5% to 100%.

At the optional operation 2106, accessing the first possible dataset in response to the first input comprises accessing the first possible dataset using a database management system engine that is configured to query a first database to retrieve the first possible dataset therefrom.

At the optional operation 2107, accessing the first possible dataset in response to the first input comprises accessing the first possible dataset by corresponding data representative of one or more of the one or more target biological material identifiers with one or more elements of the first possible dataset. In some embodiments, one or more of the one or more target biological material identifiers are selected from the group consisting of one or more genetic characteristics, one or more nucleic acid sequences, one or more protein sequences, one or more genomes, one or more demographic groups, one or more ethnic groups, one or more racial groups, one or more populations, one or more clades, one or more nationalities, one or more genders, and one or more geographic regions. In some embodiments, one or more of the one or more genetic characteristics are selected from the group consisting of age, telomere length, physical identifiers, mitochondrial nucleic acid sequences, genetic abnormalities, genetic diseases, and chromosomal abnormalities.

In some embodiments, the one or more elements include, but are not limited to, percent of obfuscation, method of obfuscation, and biological material identifiers for obfuscation. In some embodiments, the biological materials are partially or completely obfuscated. In some embodiments, the percent of obfuscation ranges from an integer percent from 5% to 100%.

In some embodiments, the method of obfuscation includes, but is not limited to, one or more of nucleic acid sequence deposition, protein sequence deposition, nucleic acid sequence degradation, and/or protein degradation. In some embodiments, deposition of one or more nucleic acid sequences includes one or more first carriers, the one or more first carriers optionally including one or more natural carriers (one or more biological materials) and/or one or more non-natural carriers. In some embodiments, deposition of one or more protein sequences includes one or more fourth carriers, the one or more fourth carriers optionally including one or more natural carriers (one or more biological materials) and/or one or more non-natural carriers. In some embodiments, the one or more natural carriers are selected from the group consisting of skin, hair, saliva, semen, urine and feces. In some embodiments, nucleic acid degradation is enzymatic and/or non-enzymatic. In some embodiments, protein degradation is enzymatic and/or non-enzymatic.

At the optional operation 2108, accessing the first possible dataset in response to the first input comprises accessing the first possible dataset by corresponding data representative of one or more of one or more percent sequence similarity or one or more percent sequence identity with one or more target nucleic acid sequences and/or one or more target protein sequences with one or more elements of the first possible dataset. In some embodiments, the one or more percent sequence similarity and/or one or more percent sequence identity is one or more integer percent from 5% to 100%.

At the optional operation 2109, accessing the first possible dataset in response to the first input comprises accessing the first possible dataset as being associated with data representative of one or more of the one or more target biological material identifiers, based on one or more characterizations stored in association with one or more elements of the first possible dataset. In some embodiments, one or more of the one or more target biological material identifiers are selected from the group consisting of one or more genetic characteristics, one or more nucleic acid sequences, one or more protein sequences, one or more genomes, one or more demographic groups, one or more ethnic groups, one or more racial groups, one or more populations, one or more clades, one or more nationalities, one or more genders, and one or more geographic regions. In some embodiments, one or more of the one or more genetic characteristics are selected from the group consisting of age, telomere length, physical identifiers, mitochondrial nucleic acid sequences, genetic abnormalities, genetic diseases, and chromosomal abnormalities.

At the optional operation, 2110, accessing the first possible dataset in response to the first input comprises accessing the first possible dataset as being associated with data representative of one or more of one or more percent sequence similarity or one or more percent sequence identity with one or more target nucleic acid sequences and/or one or more target protein sequences, based on one or more characterizations stored in association with one or more elements of the first possible dataset. In some embodiments, the one or more percent sequence similarity and/or one or more percent sequence identity is one or more integer percent from 5% to 100%.

At the optional operation 2111 and/or 2112, receiving a first input associated with a first possible dataset comprises receiving a first request associated with the first possible dataset, the first request optionally selecting data representative of the one or more target biological material identifiers. In some embodiments, one or more of the one or more target biological material identifiers are selected from the group consisting of one or more genetic characteristics, one or more nucleic acid sequences, one or more protein sequences, one or more genomes, one or more demographic groups, one or more ethnic groups, one or more racial groups, one or more populations, one or more clades, one or more nationalities, one or more genders, and one or more geographic regions. In some embodiments, one or more of the one or more genetic characteristics are selected from the group consisting of age, telomere length, physical identifiers, mitochondrial nucleic acid sequences, genetic abnormalities, genetic diseases, and chromosomal abnormalities.

At the optional operation 2113, receiving a first input associated with a first possible dataset comprises receiving a first request associated with the first possible dataset, the first request selecting data representative of one or more of one or more percent sequence similarity or one or more percent sequence identity with one or more target nucleic acid sequences and/or one or more target protein sequences. In some embodiments, the one or more percent sequence similarity and/or one or more percent sequence identity is one or more integer percent from 5% to 100%.

At the optional operation 2114, receiving a first input associated with a first possible dataset comprises receiving a first request associated with the first possible dataset, the first request determining one or more of one or more percent sequence similarity or one or more percent sequence identity with one or more target nucleic acid sequences and/or one or more target protein sequences. In some embodiments, the one or more percent sequence similarity and/or one or more percent sequence identity is one or more integer percent from 5% to 100%.

At the optional operation 2115 and/or 2116 and/or 2117 and/or 2118, receiving a first input associated with a first possible dataset comprises receiving a first request from a graphical user interface, optionally from at least one submission element of a graphical user interface, optionally at least partially identifying one or more elements of the first possible dataset and/or optionally selecting one or more elements of the first possible dataset. In some embodiments, the one or more elements include, but are not limited to, percent of obfuscation, method of obfuscation, and biological material identifiers for obfuscation. In some embodiments, the biological materials are partially or completely obfuscated. In some embodiments, the percent of obfuscation ranges from an integer percent from 5% to 100%.

In some embodiments, the method of obfuscation includes, but is not limited to, one or more of nucleic acid sequence deposition, protein sequence deposition, nucleic acid sequence degradation, and/or protein degradation. In some embodiments, deposition of one or more nucleic acid sequences includes one or more first carriers, the one or more first carriers optionally including one or more natural carriers (one or more biological materials) and/or one or more non-natural carriers. In some embodiments, deposition of one or more protein sequences includes one or more fourth carriers, the one or more fourth carriers optionally including one or more natural carriers (one or more biological materials) and/or one or more non-natural carriers. In some embodiments, the one or more natural carriers are selected from the group consisting of skin, hair, saliva, semen, urine and feces. In some embodiments, nucleic acid degradation is enzymatic and/or non-enzymatic. In some embodiments, protein degradation is enzymatic and/or non-enzymatic.

At the optional operation 2119, receiving a first input associated with a first possible dataset comprises receiving a first request from at least one submission element of a graphical user interface, the first request providing instructions identifying data representative of one or more of the one or more target biological material identifiers. In some embodiments, one or more of the one or more target biological material identifiers are selected from the group consisting of one or more genetic characteristics, one or more nucleic acid sequences, one or more protein sequences, one or more genomes, one or more demographic groups, one or more ethnic groups, one or more racial groups, one or more populations, one or more clades, one or more nationalities, one or more genders, and one or more geographic regions. In some embodiments, one or more of the one or more genetic characteristics are selected from the group consisting of age, telomere length, physical identifiers, mitochondrial nucleic acid sequences, genetic abnormalities, genetic diseases, and chromosomal abnormalities.

At the optional operation 2120, receiving a first input associated with a first possible dataset comprises receiving a first request from at least one submission element of a graphical user interface, the first request providing instructions identifying data representative of one or more of percent sequence similarity or one or more percent sequence identity with one or more target nucleic acid sequences and/or one or more target protein sequences. In some embodiments, the one or more percent sequence similarity and/or one or more percent sequence identity is one or more integer percent from 5% to 100%.

At the optional operation 2121, receiving a first input associated with a first possible dataset comprises receiving a first request from at least one submission element of a graphical user interface, the first request providing instructions determining one or more of one or more percent sequence similarity or one or more percent sequence identity with one or more target nucleic acid sequences and/or one or more target protein sequences. In some embodiments, the one or more percent sequence similarity and/or one or more percent sequence identity is one or more integer percent from 5% to 100%.

At the optional operation 2122, receiving a first input associated with a first possible dataset comprises accessing the first possible dataset in response to a first request, the first request specifying data representative of one or more of the one or more target biological material identifiers and at least one other instruction.

FIG. 15 and FIG. 16 illustrate optional embodiments of the operational flow 100 of FIG. 11. FIG. 15 and FIG. 16 shows illustrative embodiments of the optional generating operation 310, including operations generating the first possible dataset in response to the first input, and may include at least one additional operation. Generating operations may optionally include, but are not limited to, operation 3100, operation 3101, operation 3102, operation 3103, operation 3104, operation 3105, operation 3106, operation 3107, operation 3108, operation 3109, operation 3110, operation 3111, operation 3112, operation 3113, operation 3114, operation 3115, operation 3116, operation 3117, operation 3118, operation 3119, operation 3120, operation 3121, operation 3122, and/or operation 3123.

At the optional operation 3100, generating the first possible dataset in response to the first input comprises generating the first possible dataset in response to the first input, the first input including data representative of one or more of one or more target biological material identifiers. In some embodiments, one or more of the one or more target biological material identifiers are selected from the group consisting of one or more genetic characteristics, one or more nucleic acid sequences, one or more protein sequences, one or more genomes, one or more demographic groups, one or more ethnic groups, one or more racial groups, one or more populations, one or more clades, one or more nationalities, one or more genders, and one or more geographic regions. In some embodiments, one or more of the one or more genetic characteristics are selected from the group consisting of age, telomere length, physical identifiers, genetic abnormalities, genetic diseases, and chromosomal abnormalities.

At the optional operation 3101, generating the first possible dataset in response to the first input comprises generating the first possible dataset in response to the first input, the first input including data representative of one or more of one or more percent sequence similarity or one or more percent sequence identity with one or more target nucleic acid sequences and/or one or more target protein sequences. In some embodiments, the one or more percent sequence similarity and/or one or more percent sequence identity is one or more integer percent from 5% to 100%.

At the optional operation 3102, generating the first possible dataset in response to the first input comprises generating the first possible dataset by associating data representative of one or more of the one or more target biological material identifiers with one or more elements of the first possible dataset. In some embodiments, one or more of the one or more target biological material identifiers are selected from the group consisting of one or more genetic characteristics, one or more nucleic acid sequences, one or more protein sequences, one or more genomes, one or more demographic groups, one or more ethnic groups, one or more racial groups, one or more populations, one or more clades, one or more nationalities, one or more genders, and one or more geographic regions. In some embodiments, one or more of the one or more genetic characteristics are selected from the group consisting of age, telomere length, physical identifiers, mitochondrial nucleic acid sequences, genetic abnormalities, genetic diseases, and chromosomal abnormalities.

In some embodiments, the one or more elements include, but are not limited to, percent of obfuscation, method of obfuscation, and biological material identifiers for obfuscation. In some embodiments, the biological materials are partially or completely obfuscated. In some embodiments, the percent of obfuscation ranges from an integer percent from 5% to 100%.

In some embodiments, the method of obfuscation includes, but is not limited to, one or more of nucleic acid sequence deposition, protein sequence deposition, nucleic acid sequence degradation, and/or protein degradation. In some embodiments, deposition of one or more nucleic acid sequences includes one or more first carriers, the one or more first carriers optionally including one or more natural carriers (one or more biological materials) and/or one or more non-natural carriers. In some embodiments, deposition of one or more protein sequences includes one or more fourth carriers, the one or more fourth carriers optionally including one or more natural carriers (one or more biological materials) and/or one or more non-natural carriers. In some embodiments, the one or more natural carriers are selected from the group consisting of skin, hair, saliva, semen, urine and feces. In some embodiments, nucleic acid degradation is enzymatic and/or non-enzymatic. In some embodiments, protein degradation is enzymatic and/or non-enzymatic.

At the optional operation 3103, generating the first possible dataset in response to the first input comprises generating the first possible dataset by associating data representative of one or more of one or more percent sequence similarity or one or more percent sequence identity with one or more target nucleic acid sequences and/or one or more target protein sequences with one or more elements of the first possible dataset. In some embodiments, the one or more percent sequence similarity and/or one or more percent sequence identity is one or more integer percent from 5% to 100%.

At the optional operation 3104, generating the first possible dataset in response to the first input comprises generating the first possible dataset using a database management system engine that is configured to query a first database to retrieve the first possible dataset therefrom.

At the optional operation 3105, generating the first possible dataset in response to the first input comprises generating the first possible dataset by corresponding data representative of one or more of the one or more target biological material identifiers with one or more elements of the first possible dataset. In some embodiments, one or more of the one or more target biological material identifiers are selected from the group consisting of one or more genetic characteristics, one or more nucleic acid sequences, one or more protein sequences, one or more genomes, one or more demographic groups, one or more ethnic groups, one or more racial groups, one or more populations, one or more clades, one or more nationalities, one or more genders, and one or more geographic regions. In some embodiments, one or more of the one or more genetic characteristics are selected from the group consisting of age, telomere length, physical identifiers, mitochondrial nucleic acid sequences, genetic abnormalities, genetic diseases, and chromosomal abnormalities.

At the optional operation 3106, generating the first possible dataset in response to the first input comprises generating the first possible dataset by corresponding data representative of one or more of one or more percent sequence similarity or one or more percent sequence identity with one or more target nucleic acid sequences and/or one or more target protein sequences with one or more elements of the first possible dataset. In some embodiments, the one or more percent sequence similarity and/or one or more percent sequence identity is one or more integer percent from 5% to 100%.

At the optional operation 3107, receiving a first input associated with a first possible dataset comprises receiving a first request associated with the first possible dataset, and generating the first possible dataset in response to the first input.

At the optional operation 3108, receiving a first input associated with a first possible dataset comprises receiving a first request associated with the first possible dataset, the first request selecting data representative of one or more of the one or more target biological material identifiers, and generating the first possible dataset in response to the first input. In some embodiments, one or more of the one or more target biological material identifiers are selected from the group consisting of one or more genetic characteristics, one or more nucleic acid sequences, one or more protein sequences, one or more genomes, one or more demographic groups, one or more ethnic groups, one or more racial groups, one or more populations, one or more clades, one or more nationalities, one or more genders, and one or more geographic regions. In some embodiments, one or more of the one or more genetic characteristics are selected from the group consisting of age, telomere length, physical identifiers, mitochondrial nucleic acid sequences, genetic abnormalities, genetic diseases, and chromosomal abnormalities.

At the optional operation 3109, receiving a first input associated with a first possible dataset comprises receiving a first request associated with the first possible dataset, the first request selecting data representative of one or more of one or more percent sequence similarity or one or more percent sequence identity with one or more target nucleic acid sequences and/or one or more target protein sequences, and generating the first possible dataset in response to the first input. In some embodiments, the one or more percent sequence similarity and/or one or more percent sequence identity is one or more integer percent from 5% to 100%.

At the optional operation 3110, receiving a first input associated with a first possible dataset comprises receiving a first request associated with the first possible dataset, the first request determining one or more of percent sequence similarity or percent sequence identity with one or more target nucleic acid sequences and/or one or more target protein sequences, and generating the first possible dataset in response to the first input. In some embodiments, the one or more percent sequence similarity and/or one or more percent sequence identity is one or more integer percent from 5% to 100%.

At the optional operation 3111 and/or 3112 and/or 3113 and/or 3114, receiving a first input associated with a first possible dataset comprises receiving a first request from a graphical user interface, optionally from at least one submission element of a graphical user interface, optionally at least partially identifying one or more elements of the first possible dataset, and optionally selecting one or more elements of the first possible dataset, and generating the first possible dataset in response to the first input. In some embodiments, the one or more elements include, but are not limited to, percent of obfuscation, method of obfuscation, and biological material identifiers for obfuscation. In some embodiments, the biological materials are partially or completely obfuscated. In some embodiments, the percent of obfuscation ranges from an integer percent from 5% to 100%.

In some embodiments, the method of obfuscation includes, but is not limited to, one or more of nucleic acid sequence deposition, protein sequence deposition, nucleic acid sequence degradation, and/or protein degradation. In some embodiments, deposition of one or more nucleic acid sequences includes one or more first carriers, the one or more first carriers optionally including one or more natural carriers (one or more biological materials) and/or one or more non-natural carriers. In some embodiments, deposition of one or more protein sequences includes one or more fourth carriers, the one or more fourth carriers optionally including one or more natural carriers (one or more biological materials) and/or one or more non-natural carriers. In some embodiments, the one or more natural carriers are selected from the group consisting of skin, hair, saliva, semen, urine and feces. In some embodiments, nucleic acid degradation is enzymatic and/or non-enzymatic. In some embodiments, protein degradation is enzymatic and/or non-enzymatic.

At the optional operation 3115, receiving a first input associated with a first possible dataset comprises receiving a first request from at least one submission element of a graphical user interface, the first request providing instructions identifying data representative of one or more of the one or more target biological material identifiers, and generating the first possible dataset in response to the first input. In some embodiments, one or more of the one or more target biological material identifiers are selected from the group consisting of one or more genetic characteristics, one or more nucleic acid sequences, one or more protein sequences, one or more genomes, one or more demographic groups, one or more ethnic groups, one or more racial groups, one or more populations, one or more clades, one or more nationalities, one or more genders, and one or more geographic regions. In some embodiments, one or more of the one or more genetic characteristics are selected from the group consisting of age, telomere length, physical identifiers, mitochondrial nucleic acid sequences, genetic abnormalities, genetic diseases, and chromosomal abnormalities.

At the optional operation 3116, receiving a first input associated with a first possible dataset comprises receiving a first request from at least one submission element of a graphical user interface, the first request providing instructions identifying data representative of one or more of one or more percent sequence similarity or one or more percent sequence identity with one or more target nucleic acid sequences and/or one or more target protein sequences, and generating the first possible dataset in response to the first input. In some embodiments, the one or more percent sequence similarity and/or one or more percent sequence identity is one or more integer percent from 5% to 100%.

At the optional operation 3117, receiving a first input associated with a first possible dataset comprises receiving a first request from at least one submission element of a graphical user interface, the first request providing instructions determining one or more of one or more percent sequence similarity or one or more percent sequence identity with one or more target nucleic acid sequences and/or one or more target protein sequences, and generating the first possible dataset in response to the first input. In some embodiments, the one or more percent sequence similarity and/or one or more percent sequence identity is one or more integer percent from 5% to 100%.

At the optional operations 3118 and 3119, receiving a first input associated with a first possible dataset comprises receiving a first request associated with the first possible dataset 3118; and generating the first possible dataset in response to the first request, the first request specifying data representative of one or more of the one or more target biological material identifiers and at least one other instruction 3119.

At the optional operations 3120 and 3121, receiving a first input associated with a first possible dataset comprises receiving a first request, the first request specifying data representative of one or more of the one or more target biological material identifiers 3120; and generating the first possible dataset in response to the first request at least partially by performing an analysis of data representative of the one or more target biological material identifiers 3121.

At the optional operations 3122 and 3123, receiving a first input associated with a first possible dataset comprises receiving a first request, the first request specifying data representative of one or more of the one or more target biological material identifiers 3122; and generating the first possible dataset in response to the first request at least partially by performing an analysis of data representative of one or more of one or more percent sequence similarity or one or more percent sequence identity with one or more target nucleic acid sequences 3123 and/or one or more target protein sequences.

Figure 17:
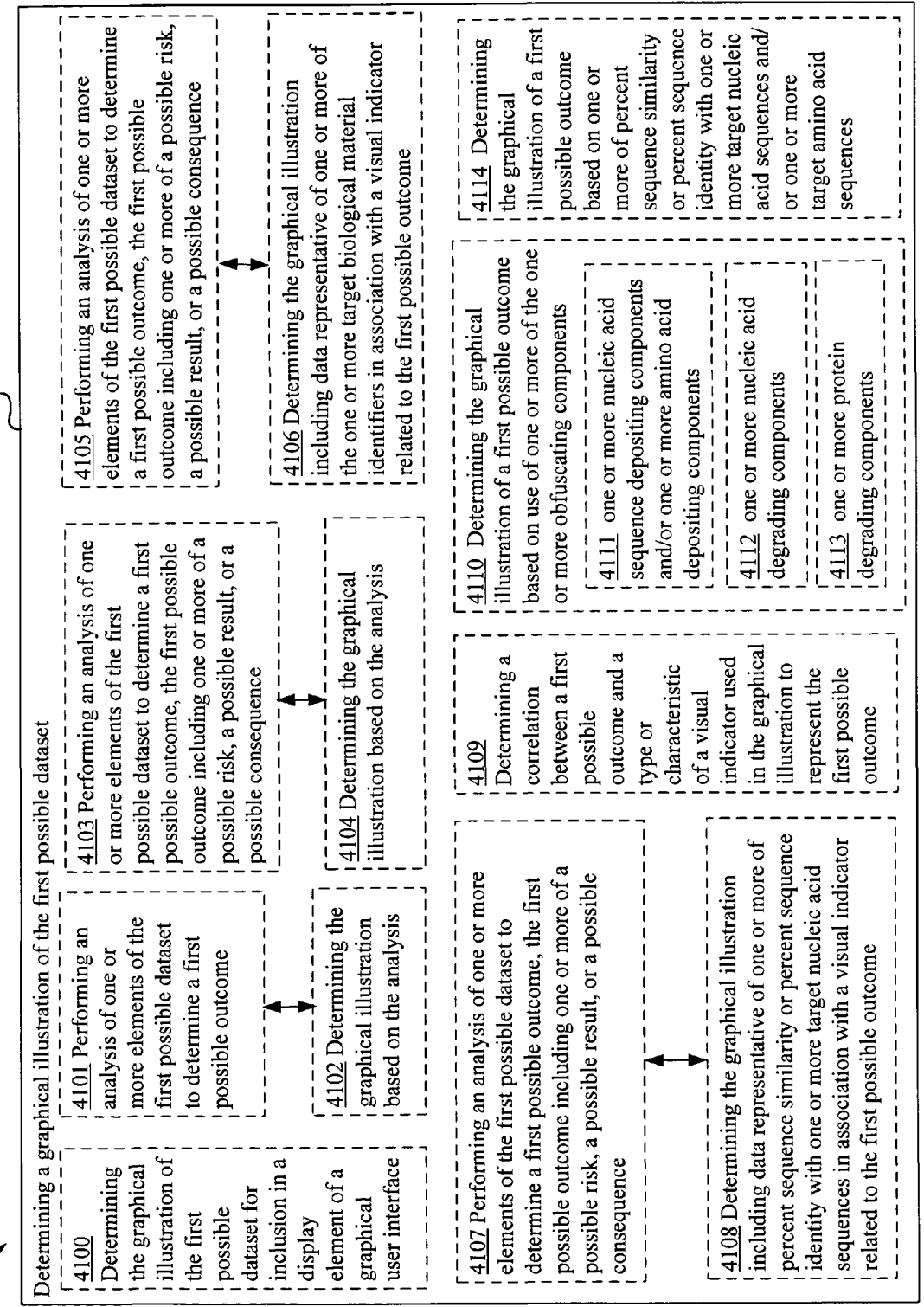
FIG. 17 shows optional embodiments of the operational flow of FIG. 11.

FIG. 17 illustrates optional embodiments of the operational flow 100 of FIG. 11. FIG. 17 shows illustrative embodiments of the optional determining operation 410, including operations determining a graphical illustration of the first possible dataset, and may include at least one additional operation. Determining operations may optionally include, but are not limited to, operation 4100, operation 4101, operation 4102, operation 4103, operation 4104, operation 4105, operation 4106, operation 4107, operation 4108, operation 4109, operation 4110, operation 4111, operation 4112, operation 4113, and/or operation 4114.

At the optional operation 4100, determining a graphical illustration of the first possible dataset comprises determining the graphical illustration of the first possible dataset for inclusion in a display element of a graphical user interface.

At the operations 4101 and 4102, determining a graphical illustration of the first possible dataset comprises performing an analysis of one or more elements of the first possible dataset to determine a first possible outcome 4101; and determining the graphical illustration based on the analysis 4102.

At the optional operations 4103 and 4104, determining a graphical illustration of the first possible dataset comprises performing an analysis of one or more elements of the first possible dataset to determine a first possible outcome, the first possible outcome including one or more of a possible risk, a possible result, or a possible consequence 4103; and determining the graphical illustration based on the analysis 4104.

At the optional operations 4105 and 4106, determining a graphical illustration of the first possible dataset comprises performing an analysis of one or more elements of the first possible dataset to determine a first possible outcome, the first possible outcome including one or more of a possible risk, a possible result, or a possible consequence 4105; and determining the graphical illustration including data representative of one or more of the one or more target biological material identifiers in association with a visual indicator related to the first possible outcome 4106.

At the optional operations 4107 and 4108, determining a graphical illustration of the first possible dataset comprises performing an analysis of one or more elements of the first possible dataset to determine a first possible outcome, the first possible outcome including one or more of a possible risk, a possible result, or a possible consequence 4107; and determining the graphical illustration including data representative of one or more of one or more percent sequence similarity or one or more percent sequence identity with one or more target nucleic acid sequences and/or one or more target protein sequences in association with a visual indicator related to the first possible outcome 4108.

At the optional operation 4109, determining a graphical illustration of the first possible dataset comprises determining a correlation between a first possible outcome and a type or characteristic of a visual indicator used in the graphical illustration to represent the first possible outcome.

At the optional operations 4110, 4111, 4112, and/or 4113, determining a graphical illustration of the first possible dataset comprises determining the graphical illustration of a first possible outcome based on use of one or more of the one or more obfuscating components 4110, the one or more obfuscating components are optionally selected from the group consisting of one or more nucleic acid sequences 4111, one or more protein sequences, one or more nucleic acid degrading components 4112, and one or more protein degrading components 4113. In some embodiments, the one or more nucleic acid sequences are optionally one or more of purified, isolated, natural or recombinant. In some embodiments, the one or more nucleic acid sequences further include one or more first carriers, the one or more first carriers are optionally natural (biological materials) or non-natural carriers. In some embodiments, the one or more protein sequences are optionally one or more of purified, isolated, natural or recombinant. In some embodiments, the one or more protein sequences further include one or more fourth carriers, the one or more fourth carriers are optionally natural (biological materials) or non-natural carriers. In some embodiments, the one or more natural first carriers are optionally selected from the group consisting of skin, hair, semen, urine, feces, and saliva. In some embodiments, the one or more nucleic acid degrading components are one or more enzymatic or non-enzymatic nucleic acid degrading components. In some embodiments, the one or more protein degrading components are one or more enzymatic or one or more non-enzymatic protein degrading components.

At the optional operation 4114, determining a graphical illustration of the first possible dataset comprises determining the graphical illustration of a first possible outcome based on one or more of one or more percent sequence similarity or one or more percent sequence identity with one or more target nucleic acid sequences and/or one or more target protein sequences.

Figure 18:
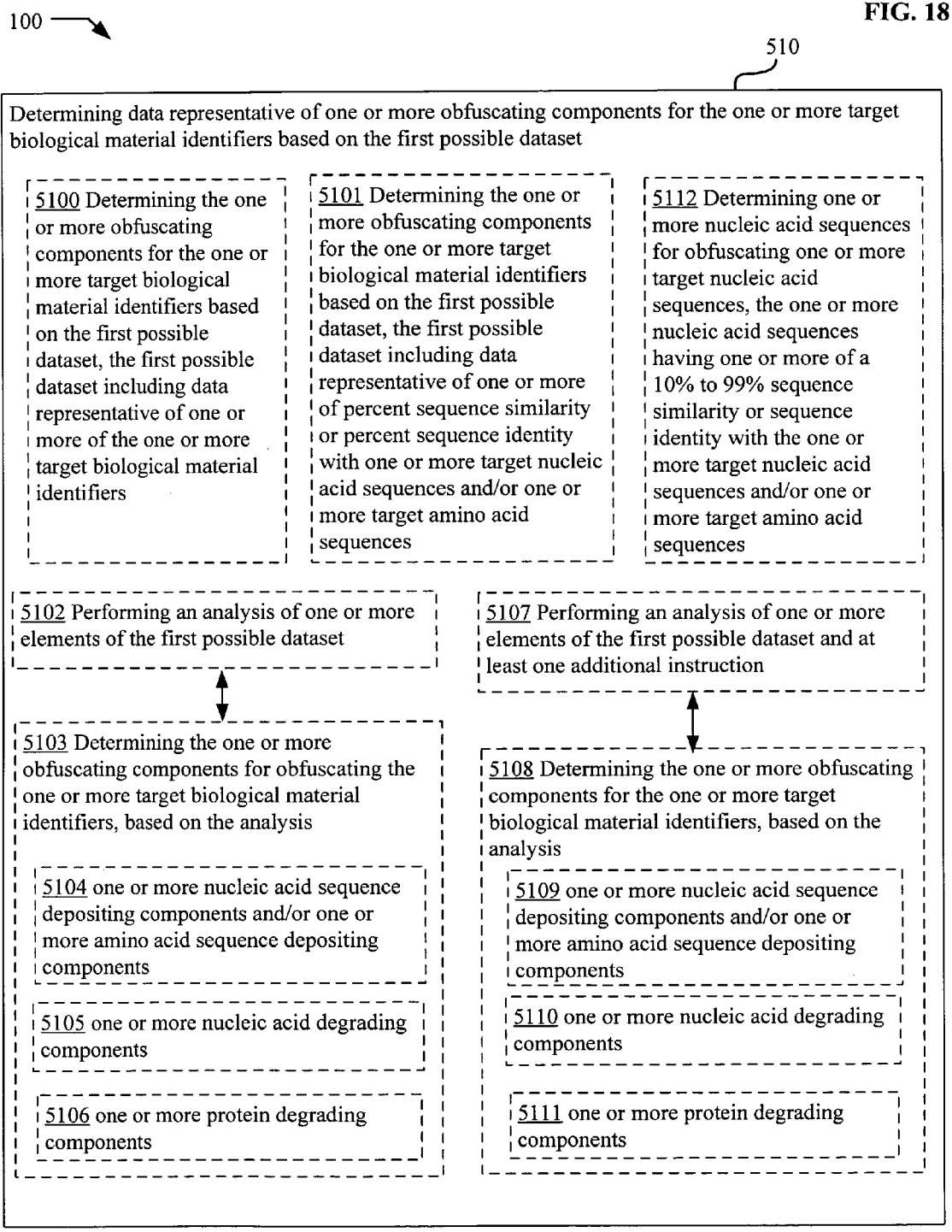
FIG. 18 shows optional embodiments of the operational flow of FIG. 11.

FIG. 18 illustrates optional embodiments of the operational flow 100 of FIG. 11. FIG. 18 shows illustrative embodiments of the determining operation 510, including operations determining data representative of one or more obfuscating components for one or more target biological material identifiers based on the first possible dataset, and may include at least one additional operation. Determining operations may optionally include, but are not limited to, operation 5100, operation 5101, operation 5102, operation 5103, operation 5104, operation 5105, operation 5106, operation 5107, operation 5108, operation 5109, operation 5110, operation 5111 and/or operation 5112.

At the optional operation 5100, determining data representative of one or more obfuscating components for one or more target biological material identifiers based on the first possible dataset comprises determining the one or more obfuscating components for the one or more target biological material identifiers based on the first possible dataset, the first possible dataset including data representative of one or more of the one or more target biological material identifiers. In some embodiments, one or more of the one or more target biological material identifiers are selected from the group consisting of one or more genetic characteristics, one or more nucleic acid sequences, one or more protein sequences, one or more genomes, one or more demographic groups, one or more ethnic groups, one or more racial groups, one or more populations, one or more clades, one or more nationalities, one or more genders, and one or more geographic regions. In some embodiments, one or more of the one or more genetic characteristics are selected from the group consisting of age, telomere length, physical identifiers, mitochondrial nucleic acid sequences, genetic abnormalities, genetic diseases, and chromosomal abnormalities.

At the optional operation 5101, determining one or more obfuscating components for the one or more target biological material identifiers based on the first possible dataset comprises determining the one or more obfuscating components for the one or more target biological material identifiers based on the first possible dataset, the first possible dataset including data representative of one or more of one or more percent sequence similarity or one or more percent sequence identity with one or more target nucleic acid sequences and/or one or more target protein sequences.

At the optional operations 5102, 5103, 5104, 5105, and/or 5106, determining one or more obfuscating components for the one or more target biological material identifiers based on the first possible dataset comprises performing an analysis of one or more elements of the first possible dataset 5102; and determining the one or more obfuscating components for obfuscating the one or more target biological material identifiers, based on the analysis 5103, wherein the one or more obfuscating components are optionally selected from the group consisting of one or more nucleic acid sequences 5104, one or more protein sequences, one or more nucleic acid degrading components 5105, and one or more protein degrading components 5106. In some embodiments, the one or more nucleic acid sequences are one or more of purified, isolated, natural or recombinant. In some embodiments, the one or more nucleic acid sequences further include one or more first carriers, the one or more first carriers being optionally natural or non-natural. In some embodiments, the one or more protein sequences are one or more of purified, isolated, natural or recombinant. In some embodiments, the one or more protein sequences further include one or more fourth carriers, the one or more fourth carriers being optionally natural or non-natural. In some embodiments, the one or more natural first carriers are optionally one or more biological materials that are optionally selected from the group consisting of skin, hair, semen, urine, feces, and saliva. In some embodiments, the one or more nucleic acid degrading components are one or more enzymatic or one or more non-enzymatic nucleic acid degrading components. In some embodiments, the one or more protein degrading components are one or more enzymatic or one or more non-enzymatic protein degrading components.

At the optional operations 5107, 5108, 5109, 5110, and/or 5111, determining one or more obfuscating components for the one or more target biological material identifiers based on the first possible dataset comprises performing an analysis of one or more elements of the first possible dataset and at least one additional instruction 5107; and determining the one or more obfuscating components for the one or more target biological material identifiers, based on the analysis 5108, wherein the one or more obfuscating components are optionally selected from the group consisting of one or more nucleic acid sequences 5109, one or more protein sequences, one or more nucleic acid degrading components 5110, and one or more protein degrading components 5111. In some embodiments, the one or more nucleic acid sequences are one or more of purified, isolated, natural or recombinant. In some embodiments, the one or more nucleic acid sequences further include one or more first carriers, the one or more first carriers being optionally natural or non-natural. In some embodiments, the one or more protein sequences are one or more of purified, isolated, natural or recombinant. In some embodiments, the one or more protein sequences further include one or more fourth carriers, the one or more fourth carriers being optionally natural or non-natural. In some embodiments, the one or more natural first carriers are optionally one or more biological materials that are optionally selected from the group consisting of skin, hair, semen, urine, feces, and saliva. In some embodiments, the one or more nucleic acid degrading components are one or more enzymatic or one or more non-enzymatic nucleic acid degrading components. In some embodiments, the one or more protein degrading components are one or more enzymatic or one or more non-enzymatic protein degrading components.

At the optional operation 5112, determining one or more obfuscating components for the one or more target biological material identifiers based on the first possible dataset comprises determining one or more nucleic acid sequences for obfuscating the one or more target nucleic acid sequences, the one or more nucleic acid sequences having one or more of a 10% to 99% sequence similarity or sequence identity with the one or more target nucleic acid sequences. At an optional operation, determining one or more obfuscating components for the one or more target biological material identifiers based on the first possible dataset comprises determining one or more protein sequences for obfuscating the one or more target protein sequences, the one or more protein sequences having one or more of a 10% to 99% sequence similarity or sequence identity with the one or more target protein sequences.

Figure 19:
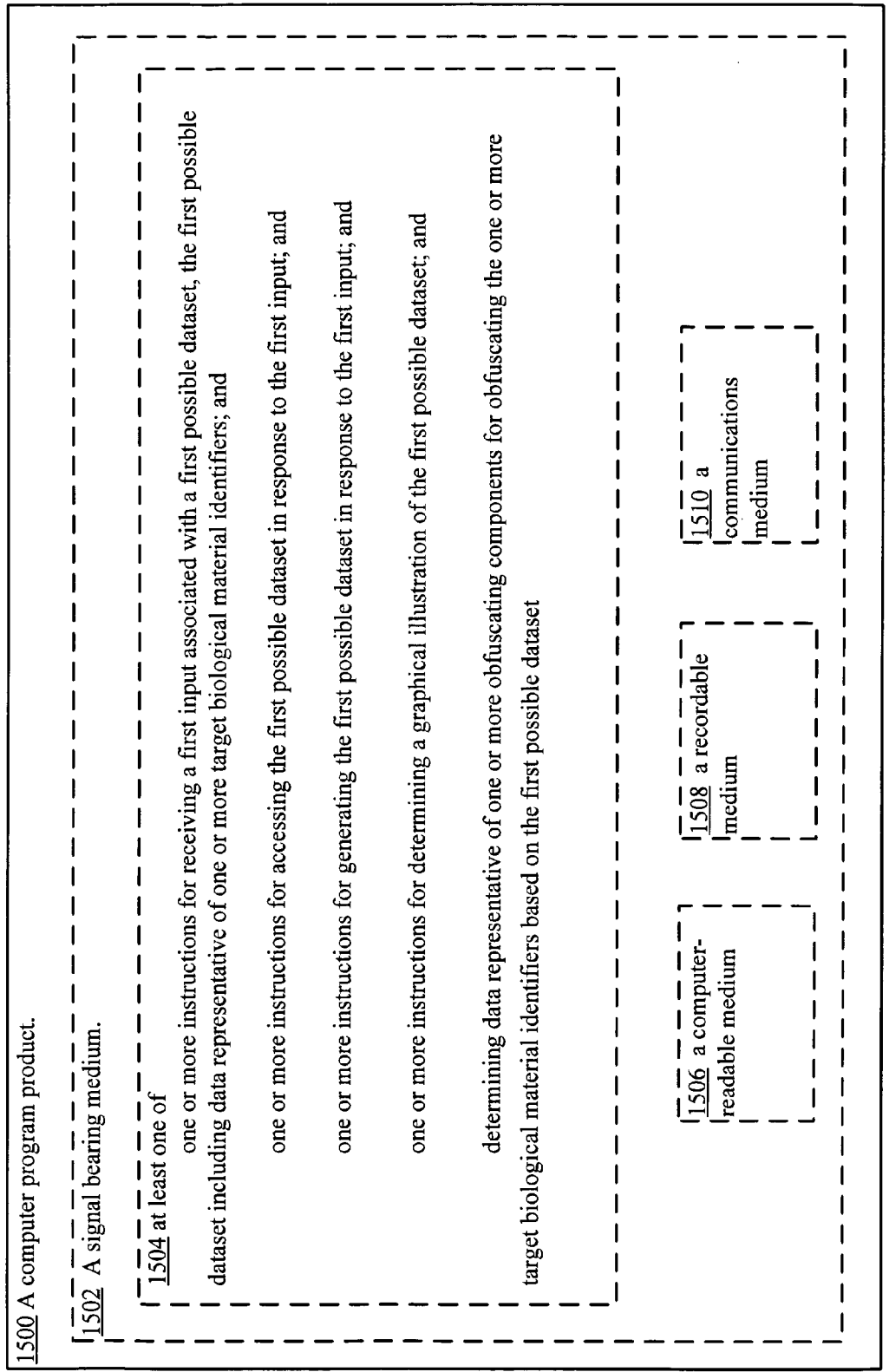
FIG. 19 shows a partial view of an illustrative embodiment of a computer program product that includes a computer program for executing a computer process on a computing device.

FIG. 19 shows a schematic of a partial view of an illustrative computer program product 1500 that includes a computer program for executing a computer process on a computing device. An illustrative embodiment of the example computer program product is provided using a signal bearing medium 1502, and may include at least one instruction of 1504: one or more instructions for receiving a first input associated with a first possible dataset, the first possible dataset including data representative of one or more target biological material identifiers; one or more instructions for accessing the first possible dataset in response to the first input; one or more instructions for generating the first possible dataset in response to the first input; one or more instructions for determining a graphical illustration of the first possible dataset; or one or more instructions for determining data representative of one or more obfuscating components for obfuscating the one or more target biological material identifiers based on the first possible dataset. The one or more instructions may be, for example, computer executable and/or logic implemented instructions. In some embodiments, the signal bearing medium 1502 of the one or more computer program 1500 products include a computer readable medium 1506, a recordable medium 1508, and/or a communications medium 1510.

Figure 20:
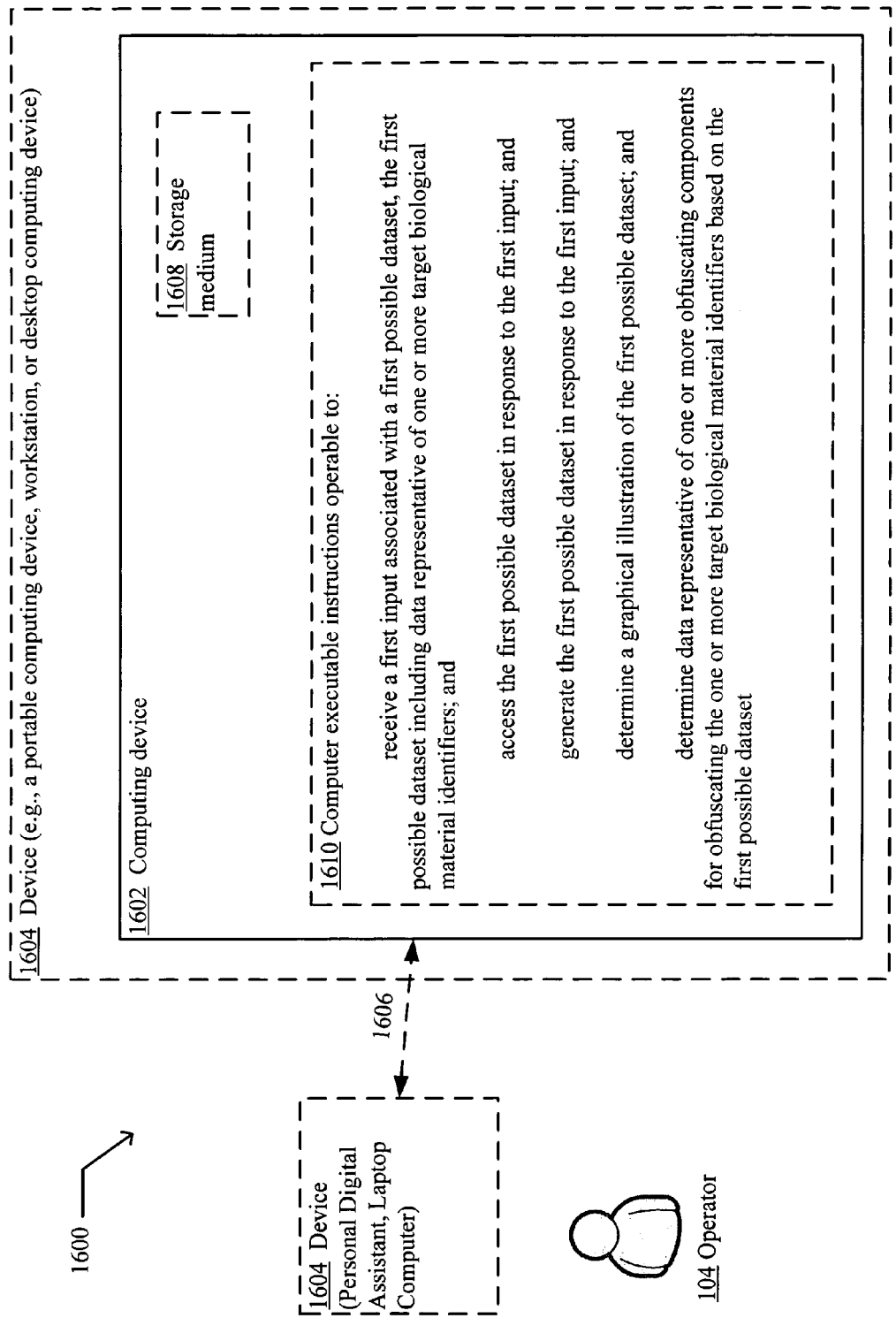
FIG. 20 shows an illustrative embodiment of a system in which embodiments may be implemented.

FIG. 20 shows a schematic of an illustrative system 1600 in which embodiments may be implemented. The system 1600 may include a computing system environment. The system 1600 also illustrates an operator 104 using a device 1604, that is optionally shown as being in communication with a computing device 1602 by way of an optional coupling 1606. The optional coupling may represent a local, wide area, or peer-to-peer network, or may represent a bus that is internal to a computing device (e.g. in illustrative embodiments the computing device 1602 is contained in whole or in part within the device 1604 or within one or more apparatus 11, or one or more computing units 81, or one or more controller units 71, or one or more monitoring units 51). An optional storage medium 1608 may be any computer storage medium.

The computing device 1602 includes one or more computer executable instructions 1610 that when executed on the computing device 1602 cause the computing device 1602 to receive the first input associated with the first possible dataset, the first possible dataset including data representative of one or more target biological material identifiers; optionally access the first possible dataset in response to the first input; optionally generate the first possible dataset in response to the first input; optionally determine a graphical illustration of the first possible dataset; and determine data representative of one or more obfuscating components for obfuscating the one or more target biological material identifiers at least partially based on a first possible dataset. In some illustrative embodiments, the computing device 1602 may optionally be contained in whole or in part within one or more units of an apparatus 11 of FIG. 5 (e.g. one or more computing units 81 and/or one or more controller units 71 and/or one or more monitoring units 51), or may optionally be contained in whole or in part within the operator device 1604.

The system 1600 includes at least one computing device (e.g. 1604 and/or 1602 and/or one or more computing units 81 of FIG. 5) on which the computer-executable instructions 1610 may be executed. For example, one or more of the computing devices (e.g. 1602, 1604, 81) may execute the one or more computer executable instructions 1610 and output a result and/or receive information from the operator 104 (optionally from one or more monitoring unit 51) on the same or a different computing device (e.g. 1602, 1604, 81) and/or output a result and/or receive information from an apparatus 11, one or more dispensing units 15, one or more sourcing units 31, one or more controller units 71, and/or one or more monitoring units 41 in order to perform and/or implement one or more of the techniques, processes, or methods described herein, or other techniques.

The computing device (e.g. 1602 and/or 1604 and/or 81) may include one or more of a desktop computer, a workstation computer, a computing system comprised a cluster of processors, a networked computer, a tablet personal computer, a laptop computer, or a personal digital assistant, or any other suitable computing unit. In some embodiments, any one of the one or more computing devices (e.g. 1602 and/or 1604 and/or 81) may be operable to communicate with a database to access the first possible dataset and/or subsequent datasets. In some embodiments, the computing device (e.g. 1602 and/or 1604 and/or 81) is operable to communicate with the apparatus 11.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.;

and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All references, including but not limited to patents, patent applications, and non-patent literature are hereby incorporated by reference herein in their entirety.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An apparatus, comprising:
   one or more sourcing units containing one or more compositions, wherein the one or more compositions are configured to obfuscate one or more biological materials, the one or more compositions including one or more of one or more nucleic acid depositing components or one or more protein depositing components and one or more carrier components; and a wide-area dispersing device positioned and operable to provide the one or more compositions to a human occupiable structure;

one or more sensors or detectors operable to detect the changes in one or more of light, motion, or noise within the human occupiable structure indicative of departure of a person; and one or more controllers operably coupled to the one or more sourcing units, the one or more sensors or detectors, and the wide-area dispersing device, the one or more controllers operable to control positioning of the wide-area dispersing device for targeting one or more areas of interest within the human occupiable structure, and the one or more controllers being configured to automatically operate the wide-area dispersing device and provide the one or more compositions to the human occupiable structure responsive to changes in the one or more of the light, motion, or noise within the human occupiable structure detected by the one or more sensors or detectors indicative of the departure of the person.

2. The apparatus of claim 1, wherein the wide-area dispersing device is selected from the group consisting of a fogger, a sprinkler, a grenade, and a mister.

3. The apparatus of claim 1, wherein the wide-area dispersing device is operable to automatically provide the one or more compositions to the human occupiable structure at least partially based on one or more timers.

4. The apparatus of claim 1, wherein the wide-area dispersing device is operable to remotely provide the one or more compositions to the human occupiable structure.

5. The apparatus of claim 4, wherein the wide-area dispersing device is operable by wireless remote control to provide the one or more compositions to the human occupiable structure.

6. The apparatus of claim 4, wherein the wide-area dispersing device is remotely actuated to provide the one or more compositions to the human occupiable structure.

7. The apparatus of claim 1, wherein the one or more nucleic acid depositing components is purified, isolated or recombinant.

8. The apparatus of claim 1, wherein the one or more protein depositing components is purified, isolated or recombinant.

9. The apparatus of claim 1, wherein one or more of the one or more carrier components performs one or more functions selected from the group consisting of: maintains one or more of the one or more nucleic acid depositing components or the one or more protein depositing components in an active form; maintains one or more of the one or more nucleic acid depositing components or the one or more protein depositing components in an inactive form; activates one or more of the one or more nucleic acid depositing components or the one or more protein depositing components; reduces inactivation of one or more of the one or more nucleic acid depositing components or the one or more protein depositing components; reduces degradation of one or more of the one or more nucleic acid depositing components or the one or more protein depositing components; increases availability of one or more of the one or more nucleic acid depositing components or the one or more protein depositing components; and increases effectiveness of one or more of the one or more nucleic acid depositing components or the one or more protein depositing components.

10. The apparatus of claim 1, wherein one or more of the one or more carrier components is pharmaceutical grade, cosmetic grade, or house-hold grade.

11. The apparatus of claim 1, wherein one or more of the one or more carrier components is co-localized with one or more of the one or more nucleic acid depositing components or the one or more protein depositing components before providing the one or more nucleic acid depositing components or the one or more protein depositing components to the human occupiable structure, and the one or more carrier components activates the one or more nucleic acid depositing components or the one or more protein depositing components.

12. The apparatus of claim 1, wherein one or more of the one or more compositions is in a form selected from the group consisting of a gel, a cream, an aerosol, a liquid, a powder, and a solid.

13. The apparatus of claim 1, wherein the one or more compositions further include one or more of one or more nucleic acid degrading components or one or more protein degrading components and one or more second carrier components.

14. The apparatus of claim 13, wherein the one or more nucleic acid degrading components are released from the wide-area dispersing device separately from the one or more protein degrading components.

15. The apparatus of claim 13, wherein the one or more protein degrading components and the one or more nucleic acid degrading components are released sequentially from the wide-area dispersing device.

16. The apparatus of claim 1, wherein the one or more controllers are operable to control automatically providing the one or more compositions to the human occupiable structure.

17. The apparatus of claim 1, wherein the one or more controllers are operable to control automatically providing the one or more compositions to the human occupiable structure at least partially based on readings from one or more of one or more sensors or one or more detectors.

18. The apparatus of claim 1, wherein the one or more controllers are operable to control one or more of activation or inactivation of one or more of the one or more nucleic acid depositing components or the one or more protein depositing components.

19. The apparatus of claim 1, wherein the one or more controllers are operable to separately release one or more of the one or more compositions.

20. The apparatus of claim 1, wherein the one or more controllers are operable to sequentially release one or more of the one or more compositions.

21. The apparatus of claim 1, wherein the wide-area dispersing device includes a grenade.

22. The apparatus of claim 1, wherein the wide-area dispersing device includes a bomb.

23. The apparatus of claim 1, wherein the wide-area dispersing device includes a fogger.

24. The apparatus of claim 1, wherein the wide-area dispersing device is configured as a portable device.

25. The apparatus of claim 1, wherein the wide-area dispersing device and the one or more sourcing units are disposed in a building.

26. The apparatus of claim 1, wherein the human occupiable structure includes at least one of a building, a room, a plane, or a boat.

27. An apparatus comprising:
a wide area dispersing device operable to provide one or more protein degrading components to a human occupiable structure;
one or more sourcing units containing the one or more protein degrading components and one or more carrier components;
one or more sensors or detectors operable to detect the changes in one or more of light, motion, or noise within the human occupiable structure indicative of presence or arrival of a person; and
one or more controllers operably coupled to the wide area dispersing device, the one or more sensors or detectors, and the one or more sourcing units, the one or more controllers operable to control positioning of the wide area dispersing device for targeting an area of interest within the human occupiable structure, and the one or more controllers being configured to automatically operate the wide-area dispersing device and provide the one or more protein degrading components to the human occupiable structure responsive to detection of motion or noise within the human occupiable structure detected by the one or more sensors or detectors indicative of the presence or arrival of the person.

28. The apparatus of claim 27, wherein the wide-area dispersing device is operable to remotely provide the one or more protein degrading components to the human occupiable structure.

29. The apparatus of claim 27, wherein at least one of the one or more protein degrading components is one or more enzymatic protein degrading components.

30. The apparatus of claim 27, wherein at least one of the one or more protein degrading components is one or more non-enzymatic protein degrading components.

31. The apparatus of claim 27, wherein one or more of the one or more carrier components performs one or more functions selected from the group consisting of: maintains one or more of the one or more protein degrading components in an active form; maintains one or more of the one or more protein degrading components in an inactive form; activates one or more of the one or more protein degrading components; reduces inactivation one or more of the one or more protein degrading components; reduces degradation one or more of the one or more protein degrading components; increases availability of one or more of the one or more protein degrading components; and increases effectiveness of one or more of the one or more protein degrading components.

32. A method comprising:
dispersing over a wide area one or more compositions including one or more nucleic acid degrading components and one or more carrier components to one or more locations in a human occupiable structure via a wide-area dispersing device responsive to detection of at least one of light, motion, noise, or temperature within the human occupiable structure indicative of presence or arrival of a person; and
controlling a position of the wide-area dispersing device within the human occupiable structure by one or more controllers operably coupled to the wide-area dispersing device.

33. The method of claim 32, wherein dispersing over the wide area one or more compositions including one or more nucleic acid degrading components and one or more carrier components to one or more locations comprises:
dispersing over the wide area the one or more compositions including the one or more nucleic acid degrading components and the one or more carrier components to the one or more locations using one or more of one or more foggers, one or more sprinklers, or one or more misters.

34. The method of claim 32, wherein dispersing over the wide area one or more compositions including one or more nucleic acid degrading components and one or more carrier components to one or more locations comprises:
remote-controlled dispersing over the wide area the one or more compositions including the one or more nucleic acid degrading components and the one or more carrier components to the one or more locations.

35. The method of claim 32, further comprising:
activating one or more of the one or more nucleic acid degrading components.

36. The method of claim 32, further comprising:
inactivating one or more of the one or more nucleic acid degrading components.

37. The method of claim 32, further comprising:
dispersing over a wide area the one or more compositions including one or more protein degrading components and one or more second carrier components to the one or more locations.

38. The method of claim 37, wherein dispersing over the wide area the one or more nucleic acid degrading components occurs separately from dispersing of the one or more protein degrading components.

39. A method comprising:
selecting a method of obfuscation from a plurality of methods of obfuscation based on readings from one or more sensors or one or more detectors;
assembling a composition based on the selected method of obfuscation, the composition including one or more of one or more nucleic acid depositing components or one or more protein depositing components;
supplying the composition to a wide-area dispersing apparatus from one or more sourcing units containing the composition;
positioning the wide-area dispersing apparatus within a human occupiable structure via one or more controllers operably coupled to the wide-area dispersing apparatus; and
automatically dispensing the composition from the wide-area dispersing apparatus to the human occupiable structure responsive to changes in one or more of a light, motion, or noise within the human occupiable structure indicative of departure of a person.

40. The method of claim 39, further comprising:
pressurizing the composition in the wide-area dispersing apparatus.

41. The method of claim 39, further comprising:
formulating the composition as a gel, a cream, an aerosol, a liquid, a powder, or a solid.

42. The method of claim 39, wherein the wide-area dispersing apparatus is selected from the group consisting of a fogger, a mister, a grenade, and a sprinkler.

43. The method of claim 39, wherein the composition includes one or more enzymes.

44. The method of claim 43, wherein one or more of the one or more enzymes are purified, isolated or recombinant.

45. The method of claim 39, further comprising:
assembling a second composition including one or more of one or more nucleic acid degrading components or one or more protein degrading components and one or more carrier components; and
providing the second composition to the wide-area dispersing apparatus.

46. An apparatus, comprising:
one or more sourcing units containing one or more compositions, wherein the one or more compositions include one or more nucleic acid depositing components configured to obfuscate one or more biological materials and one or more carrier components; and
a wide-area dispersing device positionable by one or more controllers coupled thereto and operable to automatically provide the one or more compositions to a human occupiable structure responsive to changes in one or more of a light, motion, or noise within the human occupiable structure indicative of departure of a person;
the one or more controllers operable to position the wide-area dispersing device responsive to the changes in the one or more of the light, motion, or noise.

47. The apparatus of claim 46, wherein the wide-area dispersing device is configured to access one or more targeted areas of interest within the human occupiable structure, and wherein the targeted areas of interest include crevices, nooks, or hard to reach areas within the human occupiable structure.

* * * * *